United States Patent [19]

Pasternack

[11] Patent Number: 5,726,018
[45] Date of Patent: Mar. 10, 1998

[54] NUCLEIC ACID BASED ASSAYS TO DETECT A NOVEL MAMMALIAN PROTEIN ASSOCIATED WITH UNCONTROLLED CELL DIVISION

[75] Inventor: Gary R. Pasternack, Baltimore, Md.

[73] Assignee: Johns Hopkins University, Baltimore, Md.

[21] Appl. No.: 466,603

[22] Filed: Jun. 6, 1995

Related U.S. Application Data

[63] Continuation of Ser. No. 314,503, Sep. 28, 1994, and a division of Ser. No. 995,930, Dec. 24, 1992, abandoned, which is a continuation of Ser. No. 561,989, Aug. 1, 1990, abandoned.

[51] Int. Cl.$^6$ .............................. C12Q 1/68; C07H 21/04
[52] U.S. Cl. .......................... 435/6; 536/23.5; 536/24.31
[58] Field of Search .................. 530/387.1, 388.73, 530/388.8, 389.1, 352, 358, 828; 435/737, 6; 536/23.5, 24.31

[56] References Cited

PUBLICATIONS

M. Vaesen, et al., "Purification and Characterization of Two Putative HLA Class II Associated Proteins: PHAPI and PHAPII", Jan. 1994, Biol. Chem. Hoppe–Seyler, vol. 375, pp. 113–126.
Chen, et al., 1989, "Phosphorylation of Retinoblastoma Gene Product is Modulated During the Cell Cycle and Cellular Differentiation," Cell, 58:1193–1198.
Cooper, et al., "RB and the Cell Cycle: Entrance or Exit?" 1989, Cell, 58:1009–1011.
Feuerstein, et al., 1988, "The Nuclear Matrix Protein, Numatrin (B23), Is Associated With Growth Factor–Induced Mitogenesis in Swiss 3T3 Fibroblasts and with T Lymphocyte Proliferation Stimulated by Lectins and Anti–T Cell Antigen Receptor Antibody," J. Cell Biol., 107:1629–1642.
Gerdes, et al., 1984, "Cell Cycle Analysis of a Cell Proliferation–Associated Human Nuclear Antigen Defined by the Monoclonal Antibody Ki–67," J. Immunol., 133:1710–1715.
Gomez–Marquez, et al., 1989, "The Expression of Prothymosin_Gene in T Lymphocytes and Leukemic Lymphoid Cells Is Tied to Lymphocyte Proliferation," J. Biol. Chem., 264:8451–8454.
Jaskulski, et al., 1988, "Regulation of the Proliferating Cell Nuclear Antigen Cyclin and Thymidine Kinase mRNA Levels by Growth Factors," J. Biol. Chem., 263:10175–10179.
Morla, et al., 1989, "Reversible Tyrosine Phosphorylation of cdc2: Dephosphorylation Accompanies Activation During Entry into Mitosis," Cell, 58:193–203.
Shawver, et al., 1989, "Platelet–Derived Growth Factor Induces Phosphorylation of a 64–kDA Nuclear Protein," J. Biol. Chem., 264:1046–1050.
Tan, et al., 1987, "Autoantibody to the Proliferating Cell Nuclear Antigen Neutralizes the Activity of the Auxiliary Protein for DNA Polymerase Delta," Nucleic Acids Res., 15:9299–9308.

Whelly, et al., 1977, "Relationship Between Cell Proliferation, Chromatin Template Activity And Accumulation of Nuclear Proteins," Cell Biol. Int. Rep., 1:13–21.
Ackerman, et al., 1985, "Phosphorylation of DNA Topoisomerase II by Casein Kinase II: Modulation of Eukaryotic Topoisomerase IIActivity in vitro," Proc. Natl. Acad. Sci., USA, 82:3164–3168.
Ackerman, et al., 1989, "Regulation of Casein Kinase IIActivity by Epidermal Growth Factor in Human A–431 Carcinoma Cells," J. Biol. Chem., 264:11958–11965.
Duceman, et al., 1981, "Activation of Purified Hepatoma RNA Polymerase I by Homologous Protein Kinase NII," J. Biol. Chem., 256:10755–10758.
Durban, et al., 1985, "Topoisomerase I Phosphorylation in vitro and in Rapidly Growing Novikoff Hepatoma Cells," EMBO J., 4:2921–2926.
Friedman, et al., 1985, "Nuclear Protein Phosphorylation in Isolated Nuclei from HeLa Cells. Evidence that $^{32}$P Incorporation from [γ–$^{32}$P]GTP is Catalyzed by Nuclear Kinase II," Biochem. Biophys. Acta, 847:165–176.
Holcomb, et al., 1984, "Phosphorylation of the C–Proteins of HeLa Cell hnRNP Particles," J. Biol. Chem., 259:31–40.
Klarlund, et al., 1988, "Insulin–Like Growth Factor I and Insulin Rapidly Increase Casein Kinase II Activity in BALB/c 3T3 Fibroblasts," J. Biol. Chem., 263:15872–15875.
Matthews, et al., 1984, "Nuclear Protein Kinases," Mol. Cell Biochem., 59:81–99.
Pfaff, et al., 1988, "Casein Kinase II Accumulation in the Nucleolus and Its Role in Nucleolar Phosphorylation," Biochem. Biophys. Acta, 969:100–109.
Sommercorn, et al., 1987, 1 "Activation of Casein Kinase II in Response to Insulin and to Epidermal Growth Factor," Proc. Natl. Acad. Sci., USA, 84:8834–88389.
Stetler, et al, 1982, "Phosphorylation of Deoxyribonucleic Acid Dependent RNA Polymerase II by Nuclear Protein Kinase NII: Mechanism of Enhanced Ribonucleic Acid Synthesis," Biochemistry, 21:3721–3728.
Walton, et al., 1985, "Phosphorylation of High Mobility Group Protein 14 by Casein Kinase II," J. Biol. Chem., 260:4745–4750.

(List continued on next page.)

*Primary Examiner*—Michael P. Woodward
*Attorney, Agent, or Firm*—Baker & Botts, L.L.P.

[57] ABSTRACT

Three mammalian proteins are disclosed which are useful in the diagnosis and prognosis of tumors of lymphoid and epithelial origin. The three proteins are immunologically related to each other. The level of expression of the proteins correlates with the malignant potential of lymphoid and epithelial tumors. In addition, in some cases the subcellular location of the proteins is indicative of malignant potential. Antibodies reactive with the proteins are disclosed as diagnostic tools, as are nucleic acid probes and primers for quantitating the messenger RNAs encoding the proteins. Methods for preparing and purifying the proteins are also taught.

11 Claims, 23 Drawing Sheets

OTHER PUBLICATIONS

Eliyahu, et al., 1989, "Wild–Type p53 Can Inhibit Oncogene–Mediated Focus Formation," Proc. Natl. Acad. Sci., USA, 86:8763–8767.

Ginsberg, et al., 1991, "Transfected Mouse c–jun Can Inhibit Transformation of Primary Rat Embryo Fibroblasts," Oncogene, 6:669–672.

Land, et al., 1983, "Tumorigenic Conversion of Primary Embryo Fibroblasts Requires At Least Two Cooperating Oncogenes," Nature, 304:596–602.

Makela, et al., 1992, "Alternative Forms of Max as Enhancers or Suppressors of MycRas Cotransformation," Science, 256:373–377.

Resar, et al., 1993, "B–Myc Inhibits Neoplastic Transformation and Transcriptional Activation by c–Myc," Mol. Cell. Biol., 13:1130–1136.

van den Heuvel, et al., 1993, "Large E1B Proteins of Adenovirus Types 5 and 12 Have Different Effects on p53 and Distinct Roles in Cell Transformation," J. Virol., 67:5226–5234.

Yehiely, et al., 1992, "The Gene for the Rat Heat–Shock Cognate, hsc70, Can Suppress Oncogene–Mediated Transformation," Cell. Growth Diff., 3:803–809.

Alnemri, et al., 1992, "Overexpressed Full–Length Human BCL2 Extends the Survival of Baculovirus–Infected Sf9 Insect Cells," Proc. Natl. Acad. Sci., USA, 897295–7299.

Buttyan, R., 1991, "Genetic Response of Prostate Cells to Androgen Deprivation: Insights Into the Cellular Mechanism of Apoptosis," in *Apoptosis: The Molecular Basis of Cell Death*, J. Inglis, et al, eds., Cold Spring Harbor, NY: Cold Spring Habor Laboratory Press, pp. 157–173.

de Jong, et al., 1994, "Subcellular Localization of the bcl–2 Protein in Malignant and Normal Lymphoid Cells," Cancer Res., 54:256–260.

Gerschenson, et al., 1991, "Apoptosis and Cell Proliferation are Terms of the Growth Equation," in *Apoptosis: The Molecular Basis of Cell Death*, J. Inglis, et al, eds., Cold Spring Harbor, NY: Cold Spring Harbor Laboratory Press, pp. 175–192.

Hockenbery, et al., 1991, "BCL2 Protein is Topographically Restricted in Tissues Characterized by Apoptotic Cell Death," Proc. Natl. Acad. Sci., USA, 88:6961–6965.

Kerr, et al., 1991, "Definition and Incidence of Apoptosis: An Historical Perspective," in *Apoptosis: The Molecular Basis of Cell Death*, J. Inglis, et al, eds., Cold Spring Harbor, NY: Cold Spring Habor Laboratory Press, pp. 5–29.

Martin, et al., 1994, "Dicing With Death: Dissecting the Components of the Apoptosis Machinery," Trends Biochem. Sci., 19:26–30.

Wagner, et al., 1993, "Myc–Mediated Apoptosis is Blocked By Ectopic Expression of Bcl–2," Mol. Cell. Biol., 13:2432–2440).

Briggs, et al., 1992, "Nuclear Morphometry for Prediction of Metastatic Potential in Early Squamous Cell Carcinoma of the Floor of the Mouth," Arch. Otolaryngol Head. Neck. Surg., 118:531–533.

Dawson, et al., 1991, "Nuclear Grading of Breast Carcinoma by Image Analysis. Classification by Multivariate and Neural Network Analysis," Am. J. Clin. Pathol., 95:S29–S37.

Diamond, et al., 1982, "A New Method To Assess Metastic Potential of Human Prostate Cancer: Relative Nuclear Roundness," J. Urol., 128:729–734.

Diamond, et al., 1982, "Computerized Image Analysis of Nuclear Shape As a Prognostic Factor for Prostatic Cancer," The Prostate, 3:321–332.

Drescher, et al., 1993, "Prognostic Significance of DNA Content and Nuclear Morphology in Borderline Ovarian Tumors," Gynecol. Oncol., 48:242–246.

Epstein, et al., 1984, "Nuclear Roundness Factor. A Predictor of Progression in Untreated State A2 Prostate Cancer," Cancer, 54:1666–1671.

Fleming, et al., 1990, "Image Analysis Cytometry of Dysplastic Nevi," J. Invest. Dermatol., 95:287–291.

Galera–Davidson, et al., 1990, "Cytophotometric DNA Measurements in Medullary Thyroid Carcinoma," Cancer, 65:2255–2260.

Hill, et al., 1989, "The Proportion of Stem Cells in Murine Tumors," Int. J. Radiat. Oncol. Biol. Phys., 16:513–518.

Murphy, et al., 1990, "Nuclear Shape Analysis for Assessment of Prognosis in Renal Cell Carcinoma," J. Urol., 143:1103–1107.

Pantin, et al., 1990, "Nuclear Morphometry as a Predictor of Response to Therapy in Wilms Tumor: A Preliminary Report," J. Urol., 144:952–954.

Pienta, et al., 1991, "Correlation of Nuclear Morphometry with Progression of Breast Cancer," Cancer, 68:2012–2016.

Riekaert, et al., 1992, "Computerized Morphonuclear Characteristics and DNA Content of Adenocarcinoma of the Pancreas, Chronic Pancreatitis, and Normal Tissues: Relationship with Histopathologic Grading," Hum. Pathol., 23:1210–1215.

Van Etten, et al., 1989, "The Mouse Type IV c–abl Gene Product Is a Nuclear Protein, and Activation of Transforming Ability is Associated with Cytoplasmic Localization," Cell, 58:669–678.

Weger, et al., 1992, "Morphometry and Prognosis in Cancer of the Pancreatic Head," Pathol. Res. Pract., 188:764–769.

Anderson, et al., 1986, "Tissue Specific Isoforms of Erythroid Protein 4.1 ," J. Cell Biol., 103:542a.

Anderson, et al., 1988, "Tissue–Specific Analogues of Erythrocyte Protein 4.1 Retain Functional Domains," J. Cell. Biochem., 37:269–284.

Aster, et al., 1984, "Identification of Spectrin and Protein 4.1–Like Proteins In Mammalian Lens," Biochem. Biophys. Res. Comm., 119:726–734.

Aster, et al., 1986, "The 4.1–Like Proteins of the Bovine Lens: Spectrin–binding Proteins Closely Related in Structure to Red Blood Cell Protein 4.1" J. Cell Biol., 103:115–122.

Bourguignon, et al., 1986, "Lymphoma Thy–1 Glycoprotein Is Linked to the Cytoskeleton via a 4.1–Like Protein," J. Cell Biol., 103:2529–2540.

Cho, et al., 1988, "Antibodies to Cytoskeletal Erythrocyte Protein 4.1 Recognizes Domain Specific Proteins of the Hepatocyte Plasma Membrane in Isolated Hepatocyte Couplets," Gastroenterology, 94:A529.

Cohen, et al., 1982, "A Protein Immunologically Related To Erythrocyte Band 4.1 is Found On Stress Fibres of Non–Erythroid Cells," Nature, 299:648–650.

Constantinescu, et al., 1986, "Immunological Detection of An Analogue of the Erythroid Protein 4.1 In Endothelial Cells," Cell Biol. Intl. Rept., 10:861–868.

Correas, Isabel, 1991, "Characterization of Isoforms of Protein 4.1 Present in the Nucleus," Biochem. J., 279:581–585.

Davies, et al., 1985, "Platelets Contain Proteins Immunologically Related to Red Cell Spectrin and Protein 4.1," Blood, 65:52–59.

De Cesaris, et al., 1989, "Spectrin, Fodrin and Protein 4.1–Like Proteins In Differentiating Rat Germ Cells," Differentiation, 41:216–222.

Goodman, et al. 1984, "Identification and Location of Brain Protein 4.1," Science, 224:1433–1436.

Spencer, et al., 1990, "Membrane Skeleton Protein 4.1 in Developing Xenopus: Expression In Postmitotic Cells of the Retina," Developmental Biology, 139:279–291.

Spiegel, et al., 1984, "An Analogue of the Erythroid Membrane Skeletal Protein 4.1 In Nonerythroid Cells," J. Cell Biol., 99:886–893.

Stevenson, et al., 1989, "Fodrin and Band 4.1 in a plasma Membrane–Associated Fraction of Human Neutrophils," Blood, 74:2136–2143.

Tang, et al., 1988, "Translation of an mRNA Species Encoding Non–Erythroid Protein 4.1 Generates Two Proteins One of Which May Be Localized In The Nucleus," Clin. Res., 36:405a.

Tang, et al., 1988, "Expression of Specific Isoforms of Protein 4.1 in Erythroid and Non–Erythroid Tissues," Adv. Exp. Med. Biol., 241:81–95.

Tang, et al., 1988, "Selective Expression of an Erythroid–Specific Isoform of Protein 4.1 ," Proc. Natl. Acad. Sci., USA, 85:3713–3717.

Tang, et al., 1990, "Membrane Skeletal Protein 4.1 Of Human Erythroid and Non–Erythroid Cells Is Composed Of Multiple Isoforms With Novel Sizes, Functions and Tissue Specific Expression," Cell. Molec. Biol. of Normal and Abnormal Erythroid Membranes, Alan R. Liss, Inc., New York, pp. 43–59.

Tang, et al., 1990, "Heterogeneity of mRNA and Protein Products Arising From the Protein 4.1 Gene in Erythroid and Nonerythroid Tissues," J. Cell Biol., 110:617–624.

Ziparo, et al., 1986, "Proteins of the Membrane Skeleton In Rat Sertoli Cells," J. Cell Sci., 86:145–154.

Malek, et al., 1990, "Identification and Preliminary Characterization of Two Related Proliferation–associated Nuclear Phosphoproteins," J. Biol. Chem., 265:13400–13409.

Pasternack, et al., 1986, "Murine Lymphocytes Express a Novel Form of Protein 4.1 ," J. Cell Biol., 103:543a.

Pasternack, et al., 1986, "Characterization of a Protein 4.1 Analog from Murine B Lymphocytes," J . Cell Biochem., Suppl. 10, Part B, 97.

Pasternak, et al., 1987, "Cycle–Dependant Variation in the Localization of a Protein Related to Protein 4.1," J. Cell Biol., 105:71a.

Pasternak, et al., 1989, "Protein 4.1 as Myosin Binding and Modulating Protein: Insights Into a New Functional Class of Proteins," J. Cell Biochem., Suppl. 13, Part B, 209.

Walensky, et al., 1993, "A Novel $M_r$ 32,000 Nuclear Posphoprotein Is Selectively Expressed in Cells Competent for Self–Renewal," Cancer Research, 53.4720–4726.

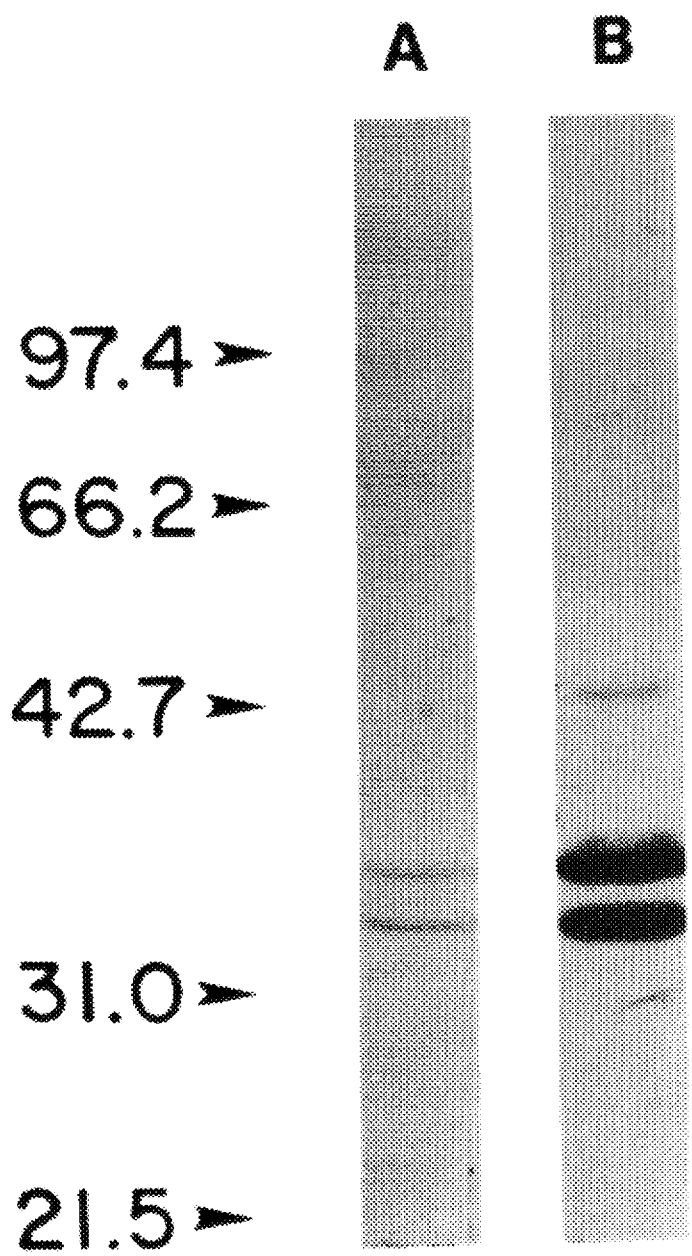

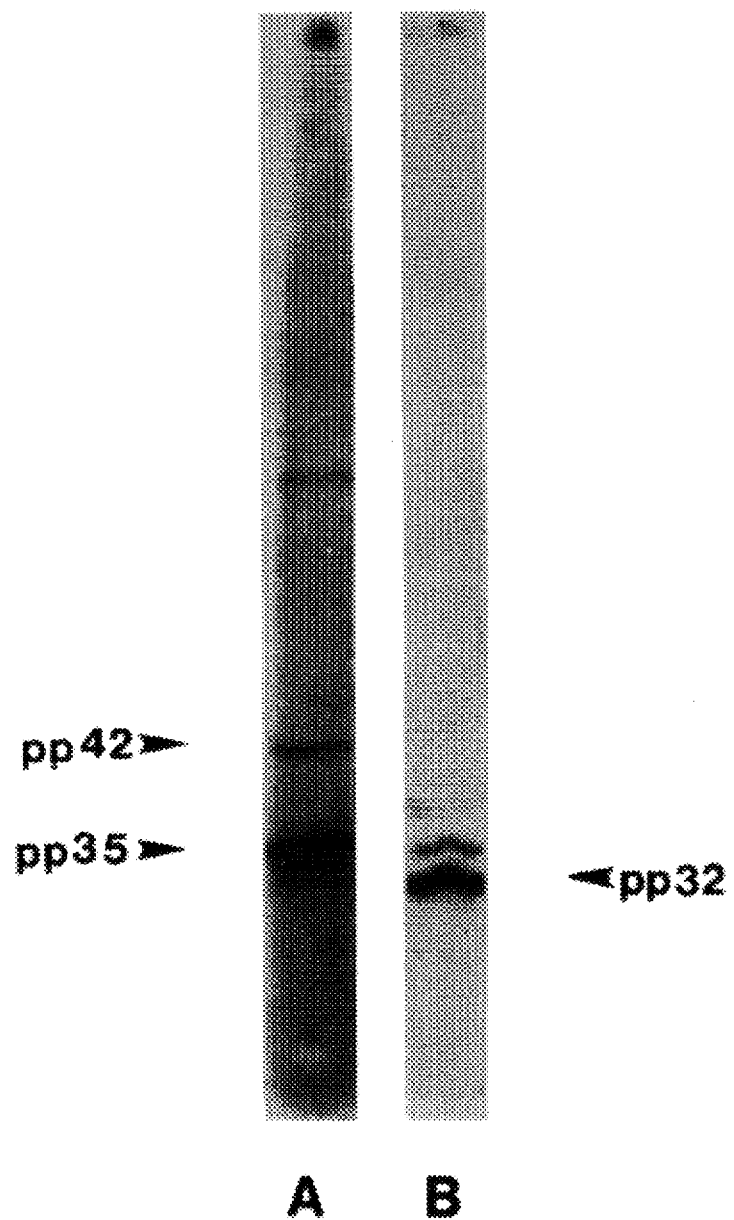

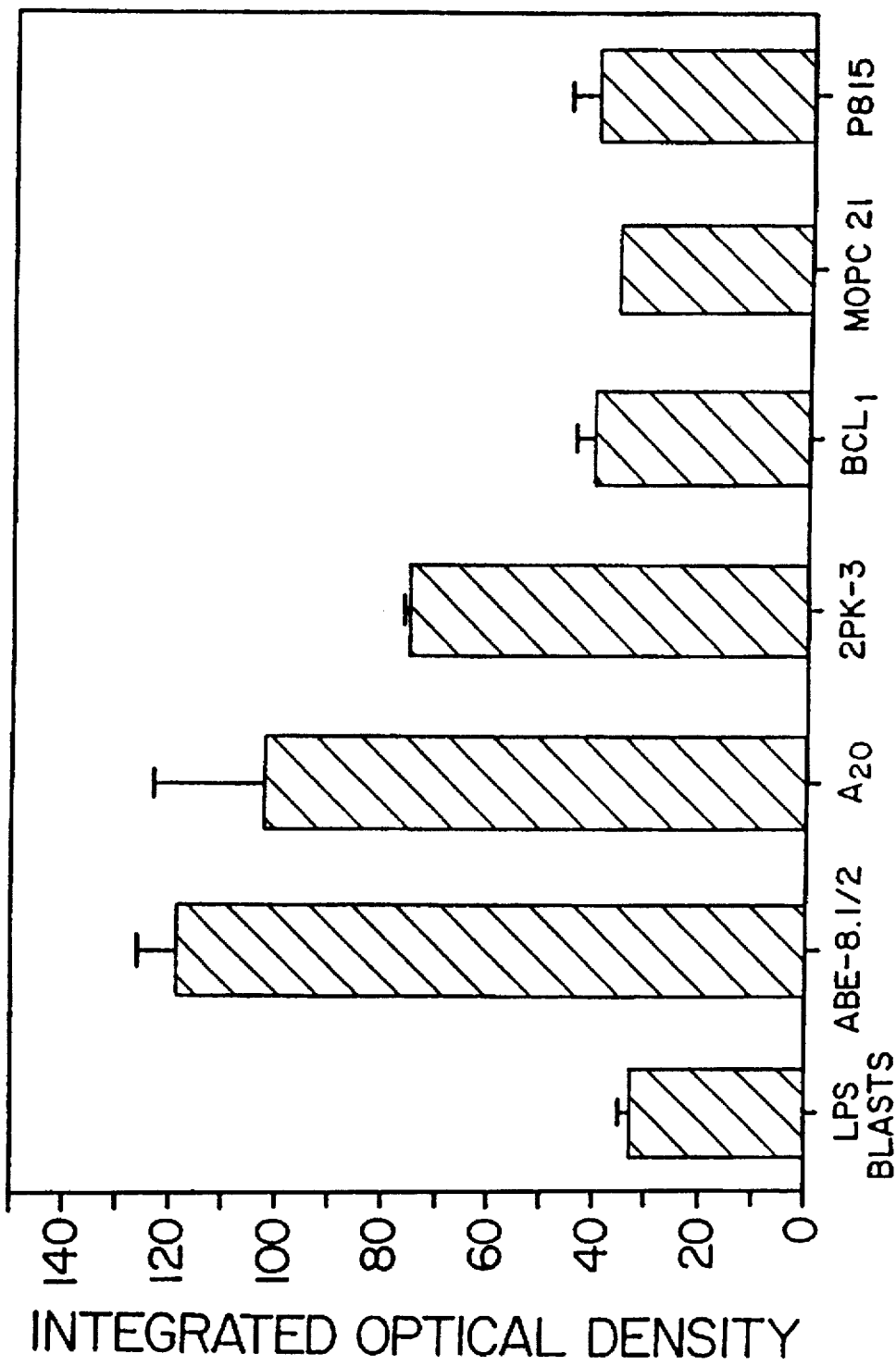

FIG. 9

```
    cggtcaagaagcttgaattaagcgaaaacagaatctcaggggacctggaagtattggcag
1   ------------+---------+---------+---------+---------+---------+ 60
     V  K  K  L  E  L  S  E  N  R  I  S  G  D  L  E  V  L  A  E - agaaatgtccgaaccttaagcatctaaatttaagtggcaacaaaataaaagatctcagca
61  ------------+---------+---------+---------+---------+---------+ 120
     K  C  P  N  L  K  H  L  N  L  S  G  N  K  I  K  D  L  S  T - caatagagccgctgaagaagttagagaatctcaagagcctagacctgtttaactgtgagg
121 ------------+---------+---------+---------+---------+---------+ 180
     I  E  P  L  K  K  L  E  N  L  K  S  L  D  L  F  N  C  E  V - tgaccaacctgaatgcctaccgagaaaacgtgttcaagctcctgccccaggtcatgtacc
181 ------------+---------+---------+---------+---------+---------+ 240
     T  N  L  N  A  Y  R  E  N  V  F  K  L  L  P  Q  V  M  Y  L - tcgatggctatgacagggacaacaaggaggcccccgactccgatgttgagggctacgtgg
241 ------------+---------+---------+---------+---------+---------+ 300
     D  G  Y  D  R  D  N  K  E  A  P  D  S  D  V  E  G  Y  V  E - aggatgacgacgaggaagatgaggatgaggaggagtatgatgaatatgcccagctagtgg
301 ------------+---------+---------+---------+---------+---------+ 360
     D  D  D  E  E  D  E  D  E  E  E  Y  D  E  Y  A  Q  L  V  E - aagatgaagaggaagaggttgaggaggaagaaggggaggaagaggatgtgagtggagagg
361 ------------+---------+---------+---------+---------+---------+ 420
     D  E  E  E  E  V  E  E  E  E  G  E  E  E  D  V  S  G  E  E - aggaggaggatgaggaaggttacaatgacggggaagtggatgacgaggaagacgaagaag
421 ------------+---------+---------+---------+---------+---------+ 480
     E  E  D  E  E  G  Y  N  D  G  E  V  D  D  E  E  D  E  E  E - aagctggtgaagaagaagggagtcagaagcgaaaacgagaaccggacgatgagggcgaag
481 ------------+---------+---------+---------+---------+---------+ 540
     A  G  E  E  E  G  S  Q  K  R  K  R  E  P  D  D  E  G  E  E - aggatgactaaggaatgaacctgtttggggaaattcctattgtgatttgactgttttac
541 ------------+---------+---------+---------+---------+---------+ 600
     D  D ccatatcccctcccccctcctattcctgcccccgaaacttatttttttctgattgtagca
601 ------------+---------+---------+---------+---------+---------+ 660 ttgctgtgggaaggagaggggaaaagtgtactgggggttgatgggggtgggggtggggg
661 ------------+---------+---------+---------+---------+---------+ 720 ggaggnnnggaataaaatactatttttactgccacactttac
721 ------------+---------+---------+--- 762
```

FIG. 10A

```
   1  gaattcccaaagtcctaaaacgcgcggccgtgggttcggggtttattgattgaattccgc   60

61  cggcgcgggagcctctgcagagagagagcgcgagagatggagatgggcagacggattcat  120
                                         M  E  M  G  R  R  I  H    8
                                               D  K        Y 121  ttagagctgcggaacaggacgccctctgatgtgaaagaacttgtcctggacaacagtcgg  180
   9  L  E  L  R  N  R  T  P  S  D  V  K  E  L  V  L  D  N  S  R   28
                                                              C  K 181  tcgaatgaaggcaaactcgaaggcctcacagatgaatttgaagaactggaattcttaagt  240
  29  S  N  E  G  K  L  E  G  L  T  D  E  F  E  E  L  E  F  L  S   48
         I        I 241  acaatcaacgtaggcctcacctcaatcgcaaacttaccaaagttaaacaaacttaagaag  300
  49  T  I  N  V  G  L  T  S  I  A  N  L  P  K  L  N  K  L  K  K   68
                           S 301  cttgaactaagcgataacagagtctcagggggcctagaagtattggcagaaaagtgtccg  360
  69  L  E  L  S  D  N  R  V  S  G  G  L  E  V  L  A  E  K  C  P   88
                           E        I        D 361  aacctcacgcatctaaatttaagtggcaacaaaattaaagacctcagcacaatagagcca  420
  89  N  L  T  H  L  N  L  S  G  N  K  I  K  D  L  S  T  I  E  P  108
         K 421  ctgaaaaagttagaaaacctcaagagcttagacctttcaattgcgaggtaaccaacctg  480
 109  L  K  K  L  E  N  L  K  S  L  D  L  F  N  C  E  V  T  N  L  128

481  aacgactaccgagaaaatgtgttcaagctcctcccgcaactcacatatctcgacggctat  540
 129  N  D  Y  R  E  N  V  F  K  L  L  P  Q  L  T  Y  L  D  G  Y  148
         A                                   V  M 541  gaccgggacgacaaggaggcccctgactcggatgctgagggctacgtggagggcctggat  600
 149  D  R  D  D  K  E  A  P  D  S  D  A  E  G  Y  V  E  G  L  D  168
               N                        V              *  *

601  gatgaggaggaggatgaggatgaggaggagtatgatgaagatgctcaggtagtggaagac  660
 169  D  E  E  D  E  D  E  E  E  Y  D  E  D  A  Q  V  V  E  D  188
         D                                Y        L 661  gaggaggacgaggatgaggaggaggaaggtgaagaggaggacgtgagtggagaggaggag  720
 189  E  E  D  E  D  E  E  E  G  E  E  D  V  S  G  E  E  E  208
         E                 V 721  gaggatgaagaaggttataacgatggagaggtagatgacgaggaagatgaagaagagctt  780
 209  E  D  E  E  G  Y  N  D  G  E  V  D  D  E  E  D  E  E  E  L  228
                                                               A 781  ggtgaagaagaaagggggtcagaagcgaaaacgagaacctgaagatgagggagaagatgat  840
 229  G  E  E  E  R  G  Q  K  R  K  R  E  P  E  D  E  G  E  D  D  248
                     G  S                          D        E 841  gactaagtggaataacctatttgaaaaattcctattgtgatttgactgtttttacccat  900
 249  D 901  atcccctctccccccccctctaatcctgccccctgaaacttattttttctgattgtaa  960

961  cgttgctgtgggaacgagaggggaagagtgtactgggggttgcggggggaggatggcggg 1020

1021  tgggggtggaataaaatactattttttactgcc                            1052
```

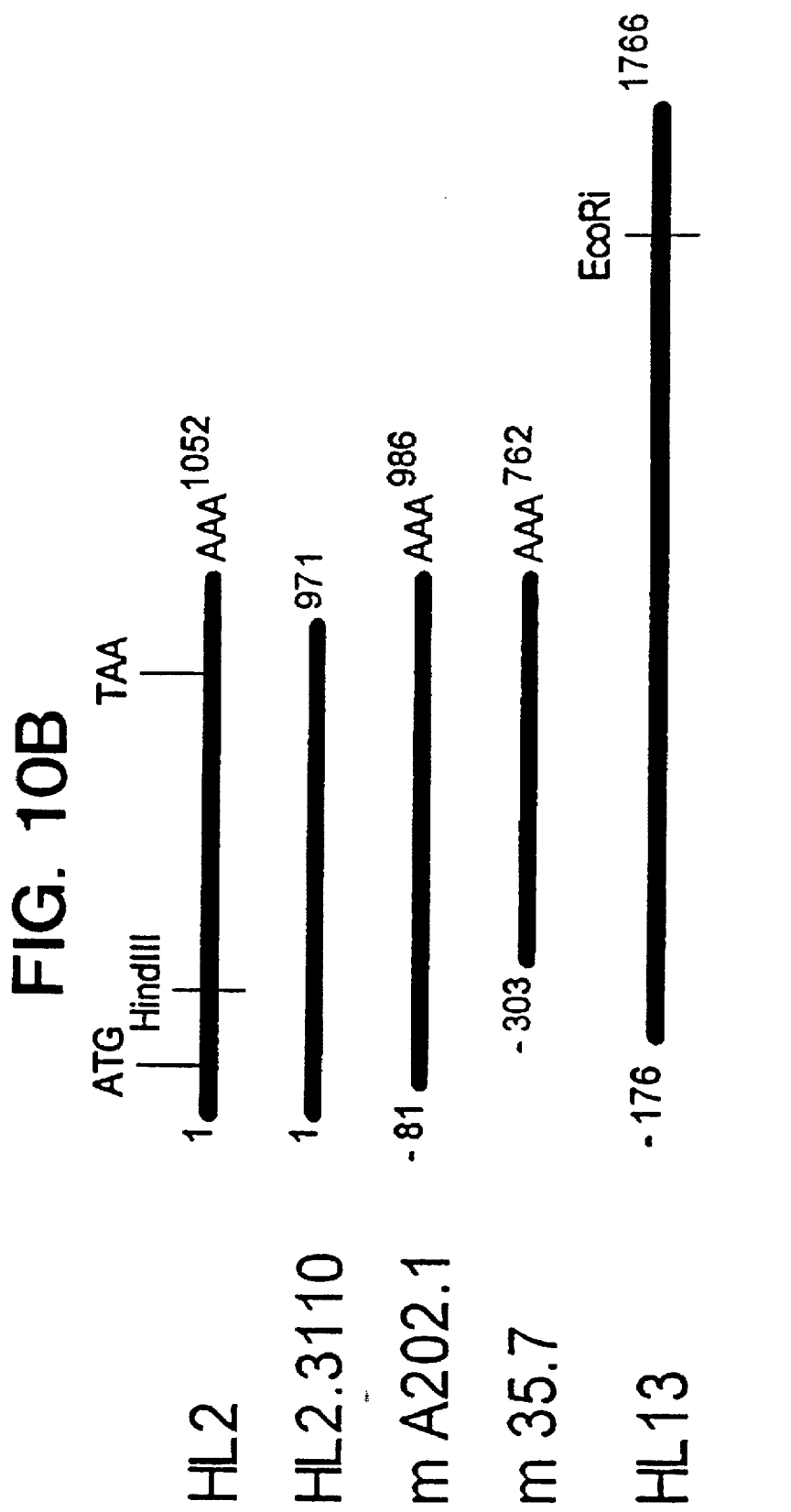

FIG. 10C

```
  1  ggcacgagaa gagagagcgc gagagatgga gatggacaaa cggatttatt
 51  tagagctgcg gaacaggacg ccctctgatg tgaaagagct ggtcctggat
101  aactgtaagt caattgaagg caaaatcgaa ggcctcacgg atgagtttga
151  agaactggaa ttcctaagta caatcaacgt aggcctcacc tccattcca
201  acttaccaaa gttaaacaaa ctcaagaagc ttgaattaag cgaaaacaga
251  atctcagggg acctggaagt attggcagag aaatgtccga acccttaagca
301  tctaaattta agtggcaaca aaataaaaga tctcagcaca atagagccgc
351  tgaagaagtt agagaatctc aagagcctag acctgtttaa ctgtgaggtg
401  accaacctga atgcctaccg agaaaacgtg ttcaagctcc tgccccaggt
451  catgtacctc gatggctatg acagggacaa caaggaggcc ccgactccg
501  atgttgaggg ctacgtggag gatgacgacg aggaagatga ggatgaggag
551  gagtatgatg aatatgccca gctagtggaa gatgaagagg aagaggttga
601  ggaggaagaa ggggaggaag aggatgtgag tggagaggag gaggaggatg
651  aggaaggtta caatgacggg gaagtggatg acgaggaaga cgaagaagaa
701  gctggtgaag aagaagggag tcagaagcga aaacgagaac cggacgatga
751  gggcgaagag gatgactaag gaatgaacct gtttggggaa atcctattg
801  tgatttgact gttttaccc atatccctc cccctcctat tcctgccccc
851  cgaaacttat tttttctga ttgtagcatt gctgtgggaa ggagagggga
901  aaagtgtact gggggttgat ggggggtggg ggtgggggggg aggggtggaa
951  taaaatacta ttttactgc cacactttac
```

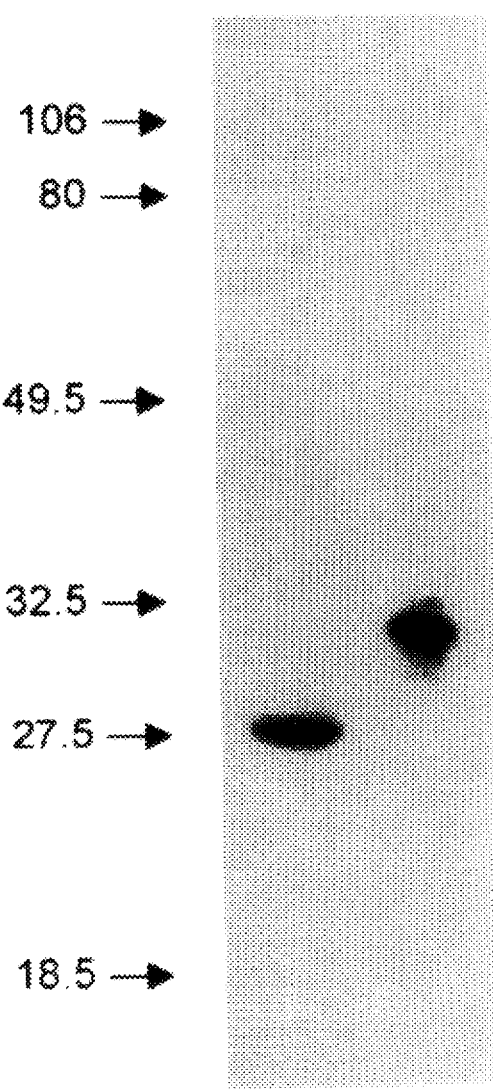

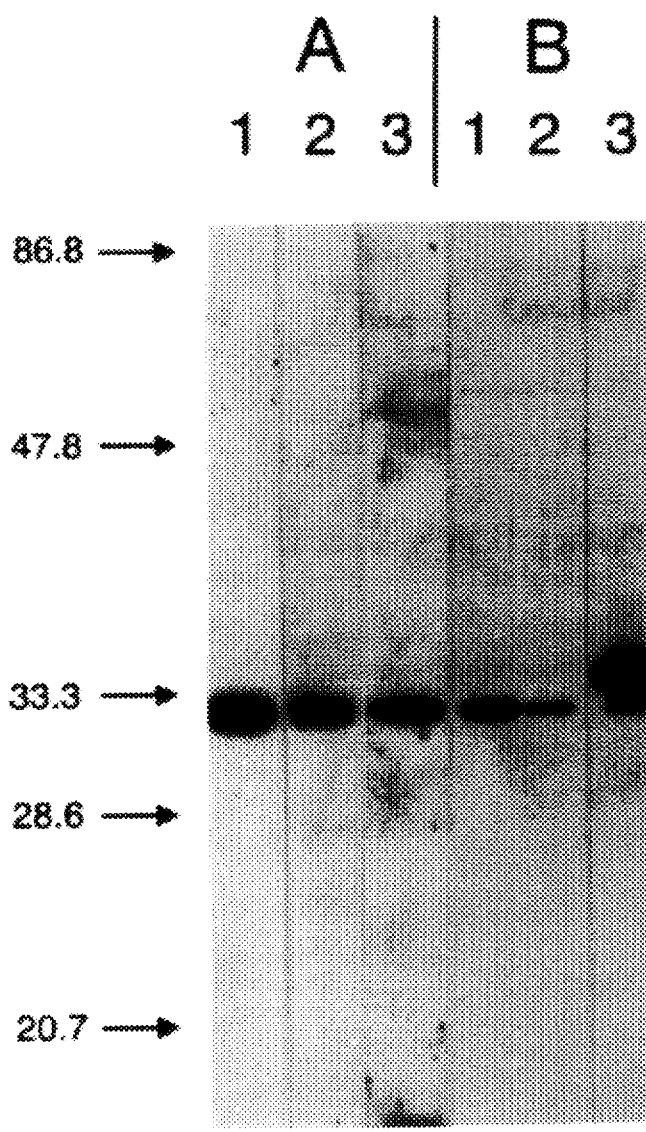

FIG. 13
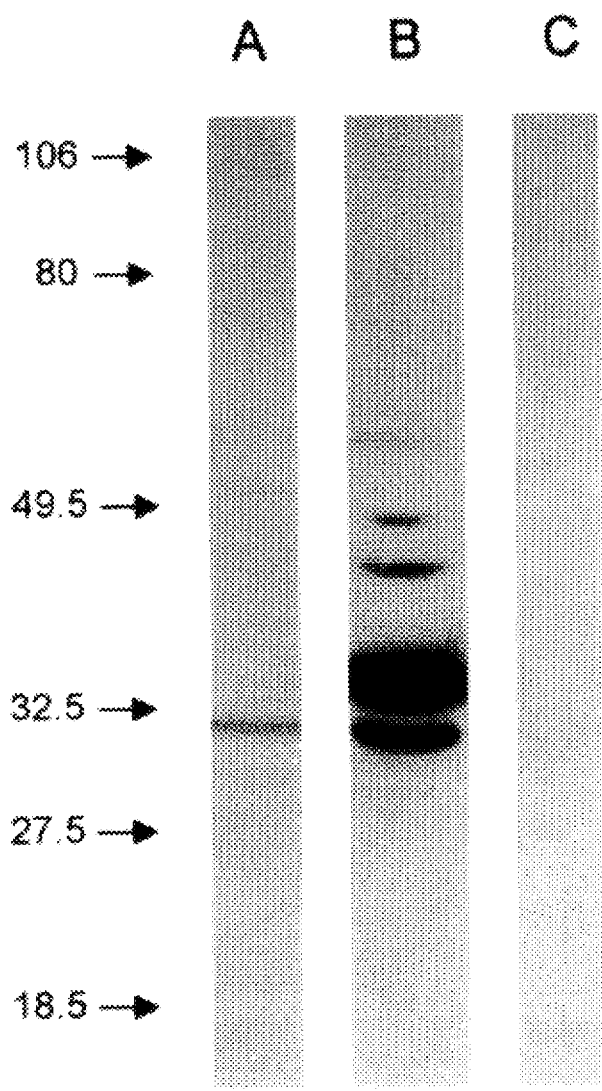
FIG. 14
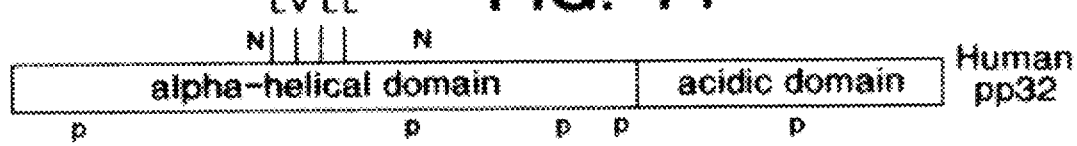
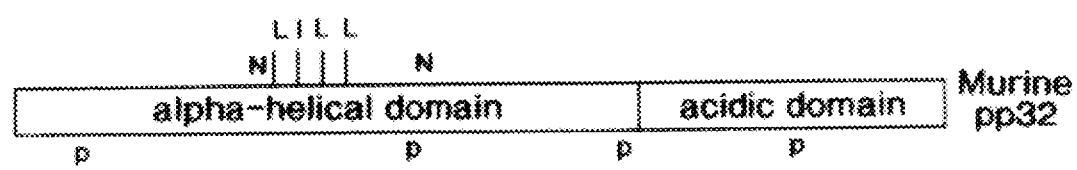

FIG. 15
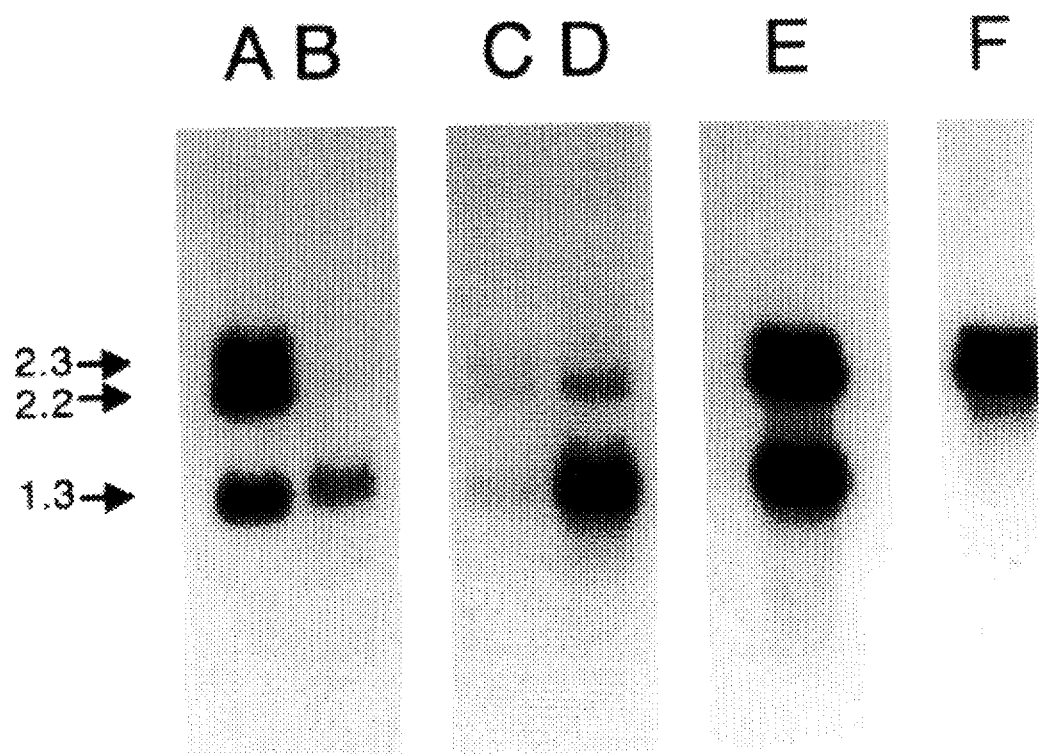
FIG. 16
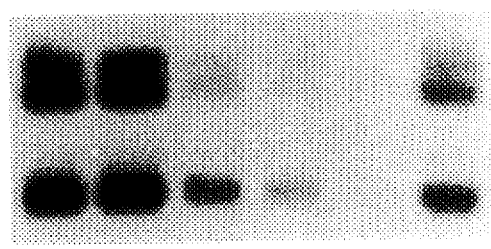
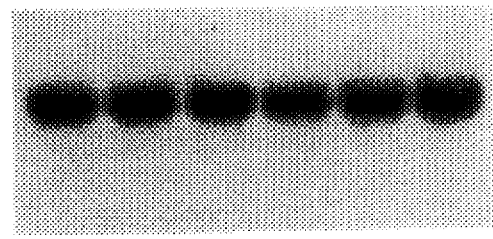

NUCLEIC ACID BASED ASSAYS TO DETECT A NOVEL MAMMALIAN PROTEIN ASSOCIATED WITH UNCONTROLLED CELL DIVISION

This application is a division of U.S. Ser. No. 07/995,930, filed Dec. 24, 1992 abandoned, and containing additional disclosure, which is a continuation of U.S. Ser. No. 07/561,989, filed Aug. 1, 1990 now abandoned, and a continuation of U.S. Ser. No. 08/314,503, filed Sep. 28, 1994.

The work leading to this invention was supported in part by Grant No. RO1CA54404 from the National Institutes of Health. The U.S. Government retains certain rights in this invention.

BACKGROUND OF THE INVENTION

A number of proliferation-associated nuclear proteins have been described (Wheely and Baserga, 1977, Cell Biol. Int. Rep., vol. 1, p. 13–21; Tan et al., 1987, Nucleic Acids Res., vol. 15, pp. 9299–9308; Gomez-Marquez et al., 1989, J. Biol. Chem., vol. 264 pp. 8451–8454; Feuerstein et al., 1988, J. Cell Biol., vol. 107, pp. 1629–1642; Shawyer et al., 1989, J. Biol. Chem., vol. 264, pp. 1046–1050; Jaskulski et al., 1988, J. Biol. Chem., vol. 263, pp. 10175–10179). Some, such as proliferating cell nuclear antigen (Tan et al., 1987, Nucleic Acids Res., vol. 15, pp. 9299–9308; Jaskulski et al., 1988, J. Biol. Chem., vol. 263, pp. 10175–10179), a co-factor of DNA polymerase delta, participate directly in proliferation. Still others, such as KI-67, are of unknown function (Gerdes et al., 1984, J. Immunol. vol. 133, pp. 1710–1715). In cases involving nuclear phosphoproteins, phosphorylation and dephosphorylation through systems of kinases and phosphatases may be important in coordinating molecular functions (Morla et al., 1989, Cell, vol. 58, pp. 193–203; Chen et al., 1989, Cell, vol. 58, pp. 1193–1198; Cooper and Whyte, 1989, Cell, vol. 58, pp. 1009–1011). While these proteins are expressed under normal physiological conditions, there is the possibility that derangement of the expression of one or more of these proteins could be involved in the growth and development of malignancies.

There is a continuing need in the medical arts for new means to diagnose and prognose cancers. Quick and simple methods can lead to more widespread cancer testing and earlier diagnoses, which can save lives by allowing therapy at earlier stages of the disease process.

SUMMARY OF THE INVENTION

It is an object of the invention to provide substantially purified preparations of mammalian proteins which are diagnostic and prognostic of human cancers.

It is another object of the invention to provide preparations of antibodies which are immunoreactive with mammalian proteins and which are useful in the diagnosis and prognosis of human cancers.

It is yet another object of the invention to provide methods of producing and purifying mammalian proteins which are diagnostic and prognostic of human cancers.

It is an object of the invention to provide diagnostic methods for predicting malignant potential of lymphoid and epithelial tumors.

These and other objects of the invention are provided by one or more of the embodiments which are described below. In one embodiment a substantially purified preparation of mammalian protein is provided which: has a molecular weight of about 35 kD; binds to myosin filaments; and is a substrate for casein kinase II in vitro.

In another embodiment of the invention substantially purified preparations of a mammalian protein are provided which protein has a molecular weight of about 32 kD and is immunoreactive with antibodies directed against pp35; and is a substrate for casein kinase II in vitro.

In still another embodiment of the invention substantially purified preparations of a mammalian protein are provided which protein has a molecular weight of about 42 kD and is immunoreactive with antibodies directed against pp35.

In another embodiment of the invention a preparation of antibodies is provided which is immunoreactive with a native mammalian protein which: has a molecular weight of about 35 kD; binds to myosin filaments; and is a substrate for casein kinase II in vitro.

In still another embodiment of the invention a preparation of antibodies is provided which is immunoreactive with a mammalian protein which: has a molecular weight of about 32 kD; is immunoreactive with antibodies directed against pp35; and is a substrate for casein kinase II in vitro.

In still another embodiment of the invention a preparation of antibodies is provided which is immunoreactive with a mammalian protein which: has a molecular weight of about 42 kD; and is immunoreactive with antibodies directed against pp35.

In yet another embodiment a preparation of antibodies is provided which is immunoreactive with a polypeptide comprising amino acid sequences as shown in FIG. 9.

In still another embodiment of the invention a preparation of antibodies is provided which is produced by immunizing animals with an immunogen comprising a polypeptide comprising amino acid sequences as shown in FIG. 9.

In another embodiment a method is provided of purifying mammalian proteins pp35 and pp32 comprising: lysing cells in a detergent and low-ionic strength buffer to form a cell lysate; separating components of the cell lysate by DEAE-cellulose chromatography and selecting desired components; separating the desired components into fractions by HPLC anion-exchange chromatography and selecting desired fractions; separating the desired fractions into constituents by HPLC hydroxylapatite chromatography and selecting desired constituents, desired constituents having a molecular weight of about 35 or about 32 kD.

In still another embodiment of the invention, nucleic acid primers are provided for amplifying sequences encoding pp32, pp35 or pp42.

In another embodiment of the invention a nucleic acid probe is provided which is complementary to mRNA encoding pp32, pp35 or pp42.

In still another embodiment of the invention diagnostic methods are provided for predicting malignant potential of lymphoid and epithelial tissues comprising: providing a section of human lymphoid or epithelial tissue; determining levels of or intracellular sites of expression of a gene product expressed from a gene selected from the group consisting of: pp32, pp35, and pp42.

In yet another embodiment of the invention a method of producing a preparation of a mammalian protein selected from the group consisting of pp32, pp35, and pp42 is provided comprising: culturing a mammalian lymphoblastoid cell line; collecting the mammalian protein from the nucleus of cells of the cell line.

In still another embodiment of the invention, a method is provided for treating tumors characterized by increased expression of pp32, by ablation of pp32 which will either directly result in cell death or will potentiate the effects of chemotherapeutic agents that ultimately kill cells through programmed cell death. In particular, the invention provides a method for inhibiting proliferation of cells having potential for continuous increase in cell number (e.g., stem cells or neoplastic cells) by obtaining a DNA molecule comprising a cDNA sequence operably linked to a promoter such that it will be expressed in antisense orientation, the cDNA having all or part of the sequence of pp32, and transfecting, with the DNA molecule, the cells with potential for uncontrolled proliferation.

In yet another embodiment of the invention, a method is provided for screening candidate drugs to detect drugs with potential for decreasing the rate of accumulation of tumor cells by incubating the candidate drug with cells transfected with DNA encoding pp32 and monitoring one or more biological activities of pp32 in the transfected cells. Particularly preferred activities of pp32 for monitoring in such a screening assay include inhibition of programmed cell death, inhibition of co-transformation by two oncogenes, such as ras and myc, or induction of malignant nuclear morphology in the transformed cell. These and other embodiments of the invention will be described in more detail below.

The present invention thus provides the arts of oncology and pathology with entirely new diagnostic tools for determining the malignant potential of lymphoid and epithelial tumors. Further, by disclosing the discovery of a protein (pp32) that functions in the pathway by which control of proliferation is released, the invention provides a new therapeutic target for tumor therapy as well as methods to aid in selecting drugs specific for cells characterized by uncontrolled proliferation (i.e., neoplastic cells). The human nucleic acid sequence encoding pp32 provided herein may be used for more specific diagnostic assays of tumor tissue or in the creation of antisense expression vectors to inhibit the expression of pp32 by tumor cells.

BRIEF DESCRIPTION OF THE DRAWINGS

FIG. 4B shows immunoreactivity of partially-purified pp35, pp32, and pp42. Panel B illustrates a Western blot of an HPLC anion exchange fraction similar to those shown in FIG. 4A. Antibody to denatured pp35 identifies three species, pp42, pp35, and pp32. Panel A is a Coomassie-stained gel lane showing purified pp35 and pp32, and is included as a standard. The numbered arrows indicate the positions of molecular weight standards in kDa.

FIG. 5 shows specificity of antibodies to native pp35 and pp32. The figure represents a Western blot of $A_{20}$ lysate using affinity-purified antibody to native pp32 (anti-pp32n) in lane B. Anti-pp35n reacts primarily with pp35, but also slightly with pp32, pp42, and an unidentified band of approximately 68 kDa. Anti-pp32n reacts principally with pp32, but cross-reacts slightly with pp35.

FIG. 6A shows the results for pp35 normalized to total cell protein (Panel A) and to cell number (Panel C), and for pp32 (Panels B and D). FIG. 6B shows the autoradiographs from which the data in FIG. 6A was obtained. Panel A represents the standard curve. Beginning at the left, the first pair of lanes illustrates the duplicate determinations for 31 ng each of pp35 and pp32. Each successive pair of lanes represents 62.5, 125, 250, and 500 ng. Panel B show the experimental autoradiographs. Beginning at the left, the first pair of lanes represents duplicate determinations for the 72 h time point. Each successive pair of lanes represents duplicate determinations for the 48 h, 24 h, 1 h, and 0 h time points.

FIGS. 7A and 7B show expression of pp35 and pp32 in cell lines. Cells from the indicated lines were processed for quantitative immunoblotting as described in the description of FIG. 6. Equal amounts of cellular protein from each line were analyzed. The figures show the mean of duplicate determinations, and the error bars indicate the range; only a single determination was available for the MOPC 21 subclone (P3.6.2.8.1). Panels A and B show the results respectively for pp35 and pp32. ABE-8.½ is a pre-B cell line. $A_{20}$, 2PK-3, and $BCL_1$ are all B cell lines. MOPC 21 is a plasmacytoma.

FIG. 9 shows pp32-related cDNA sequences (SEQ ID No:4). Three hundred bases of sequence from the open reading frame of cloned pp32 cDNA are shown together with the predicted amino acid sequence. The approximately 1 kb cDNA was subcloned into Bluescript and sequenced by the dideoxynucleotide method; approximately two-thirds of the insert has been sequenced to date. The underlined sequence exactly matches sequence obtained independently from a pp35 tryptic peptide isolated by reverse phase chromatography.

FIGS. 10A and C show the cDNA sequences of human and murine pp32 SEQ ID No:1 and SEQ ID No:3 respectively; the clones used to derive those sequences are diagrammed in FIG. 10B.

FIG. 11 shows that recombinant murine pp32 fragment is recognized by antibody to native murine pp32 on Western blot.

FIG. 12 depicts a Western blot on which native human pp32, recombinant human pp32, and murine pp32 co-migrate and react with anti-pp32 antibodies.

FIG. 13 shows that the in vitro translation product of human pp32 cDNA co-migrates with murine pp32 on SDS-PAGE.

FIG. 14 is a cartoon showing the structure of human and murine pp32.

FIG. 15 shows expression of human and murine pp32 RNA analyzed by Northern blot.

FIG. 16 shows Northern blots demonstrating the time course of pp32 RNA levels during induced differentiation of HL-60 cells.

DETAILED DESCRIPTION OF THE PREFERRED EMBODIMENTS

Figure 1:
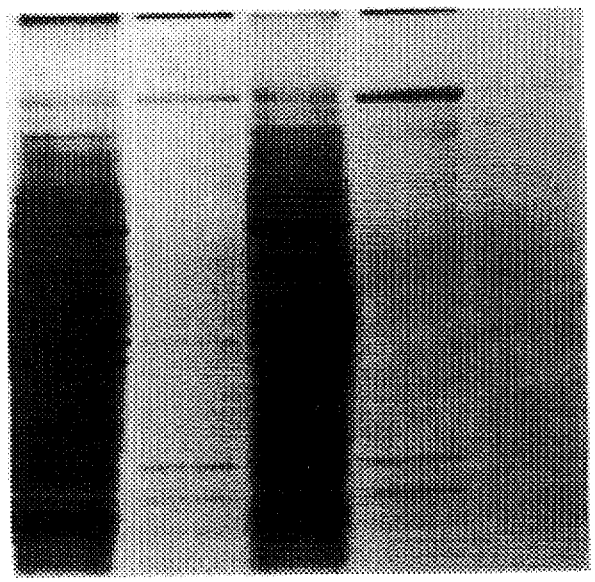
FIG. 1 shows myosin-affinity separation of pp35. A lysate prepared from $A_{20}$ cells (8 mg total protein) was incubated with 1 mg of cross-linked myosin for 30 min at 4°. The myosin was pelleted at 16,000×g for 10 min., the supernatant removed, and the pellet washed three times in lysis buffer. The pellet was then resuspended in lysis buffer containing 1M KCl and incubated at 4° for 15 min. After incubation, the myosin was again pelleted. The figure represents total $A_{20}$ lysate, lane A; myosin precipitate, lane B; myosin supernatant, lane C; KCl myosin precipitate, lane D; and KCl myosin extract, lane E. The figure shows a Coomassie-stained 7–15% gel. Myosin pellets were prepared for electrophoresis using Laemmli solubilizing buffer without β-mercaptoethanol to avoid solubilizing the disulfide cross-linked myosin; β-mercaptoethanol was added after re-centrifugation and prior to electrophoresis.

It is a finding of the present invention that the expression of certain related mammalian nuclear proteins can be used to predict the malignant potential of lymphoid and epithelial tumors. Antibodies have been raised against the native forms of these proteins and they have been used as immunohistochemical reagents. The percentage of cells which stain positive with the reagents, the intensity of staining, and in some cases the location of the staining, correlates with the malignant potential of the lymphoid or epithelial tumors.

DEFINITIONS

In describing the present invention, the following terminology is used in accordance with the definitions set out below.

Nucleic Acids

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed stand of DNA (i.e., the strand having a sequence homologous to the mRNA).

A DNA sequence "corresponds" to an amino acid sequence if translation of the DNA sequence in accordance with the genetic code yields the amino acid sequence (i.e., the DNA sequence "encodes" the amino acid sequence).

One DNA sequence "corresponds" to another DNA sequence if the two sequences encode the same amino acid sequence.

Two DNA sequences are "substantially homologous" when at least about 85%: (preferably at least about 90%:, and most preferably at least about 95%:) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art. See e.g., Maniatis et al., supra; DNA Cloning, vols. 1 and II supra; Nucleic Acid Hybridization, supra.

"Recombinant DNA" is a DNA molecule which includes DNA sequences obtained from two or more species.

A coding sequence is an in-frame sequence of codons that (in view of the genetic code) correspond to or encode a protein or peptide sequence. Two coding sequences correspond to each other if the sequences or their complementary sequences encode the same amino acid sequences. A "coding sequence" in association with appropriate regulatory sequences may be transcribed and translated into a polypeptide in vivo. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. A coding sequence is "under the control" of the promoter sequence in a cell when RNA polymerase which binds the promoter sequence transcribes the coding sequence into mRNA which is then in turn translated into the protein encoded by the coding sequence.

For purposes of this invention, a cell has been "transfected" by exogenous DNA when such exogenous DNA has been introduced inside the cell membrane. Exogenous DNA may or may not be integrated (covalently linked) to chromosomal DNA making up the genome of the cell. In procaryotes and yeast, for example, the exogenous DNA may be maintained on an episomal element such as a plasmid. With respect to eucaryotic cells, a stably transfected cell is one in which the exogenous DNA has become integrated into a chromosome so that it is inherited by daughter cells through chromosome replication. This stability is demonstrated by the ability of the eukaryotic cell to establish cell lines or clones comprised of a population of daughter cells containing the exogenous DNA.

A "clone" is a population of cells derived from a single cell or common ancestor by mitosis.

A "cell line" is a clone of a primary cell that is capable of stable growth in vitro for many generations.

A "replicon" is any genetic element (e.g., plasmid, chromosome, virus) that functions as an autonomous unit of DNA replication in vivo; i.e., capable of replication under its own control.

Vectors are used to introduce a foreign substance, such as DNA, RNA or protein, into an organism. Typical vectors include recombinant viruses (for DNA) and liposomes (for protein). A "DNA vector" is a replicon, such as plasmid, phage or cosmid, to which another DNA segment may be attached so as to bring about the replication of the attached segment.

An "expression vector" is a DNA vector which contains regulatory sequences which will direct protein synthesis by an appropriate host cell. This usually means a promoter to bind RNA polymerase and initiate transcription of mRNA, as well as ribosome binding sites and initiation signals to direct translation of the mRNA into a polypeptide. Incorporation of a DNA sequence into an expression vector at the proper site and in correct reading frame, followed by transfection of an appropriate host cell by the vector, enables the production of a protein encoded by said DNA sequence.

An expression vector may alternatively contain an antisense sequence, where a small DNA fragment, corresponding to all or part of an mRNA sequence, is inserted in opposite orientation into the vector after a promoter. As a result, the inserted DNA will be transcribed to produce an RNA which is complementary to and capable of binding or hybridizing to the mRNA. Upon binding to the mRNA, translation of the mRNA is prevented, and consequently the protein coded for by the mRNA is not produced. Production and use of antisense expression vectors is described in more detail in U.S. Pat. No. 5,107,065 and U.S. Pat. No. 5,190,931, both of which are incorporated herein by reference.

A "DNA library" is a population of vectors which each contain a DNA coding sequence for some protein. The population as a whole encodes a large number of peptides, and the sequence for a particular one of the peptides can be recovered from the library using an appropriate screening procedure.

"Amplification" of nucleic acid sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8:291–294).

Polypeptides

Polypeptides are polymers made up of a sequence of amino acids linked by peptide bonds, containing at least 10 and usually 50 or more amino acids in the sequence. Proteins are polypeptides which usually have 35 or more amino acids and form a characteristic three dimensional structure (tertiary structure).

Two amino acid sequences are "substantially homologous" when at least about 90% of the amino acids match over the defined length of the amino acid sequences, preferably a match of at least about 92%, more preferably a match of at least about 95%.

One amino acid sequence "corresponds" to another amino acid sequence if at least 75% of the amino acid positions in the first sequence are occupied by the same amino acid residues in the second sequence. Preferably 90% of the amino acid positions are identical, and most preferably 95% of the amino acid positions are identical. Alternatively, two amino acid sequences are considered to correspond to each other if the differences between the two sequences involve only conservative substitutions.

"Conservative amino acid substitutions" are the substitution of one amino acid residue in a sequence by another residue of similar properties, such that the secondary and tertiary structure of the resultant peptides are substantially the same. Conservative amino acid substitutions occur when an amino acid has substantially the same charge as the amino acid for which it is substituted and the substitution has no significant effect on the local conformation of the protein. Amino acid pairs which may be conservatively substituted for one another are well-known to those of ordinary skill in the art.

For the purposes of defining the present invention, two proteins are homologous if 70% of the amino acids in their respective sequences are the same; usually the amino acid sequences of homologous proteins are 80% identical. The sequences of substantially homologous proteins will be 85% identical, preferably the identity will be 90%, most preferably 95%. Two proteins are similar if the majority of the differences between their respective amino acid sequences involve conservative substitutions.

The polypeptides of this invention encompass pp32 and pp32 analogs. pp32 is a naturally occurring, mature protein from mammals, especially mice and humans, and further encompasses all precursors and allelic variations of pp32, as well as including forms of heterogeneous molecular weight that may result from inconsistent processing in vivo. An example of the pp32 sequence is shown in FIG. 10A and SEQ ID No:2 "pp32 analogs" are a class of peptides which includes:

1) "pp32 muteins," which are polypeptides which are substantially homologous to pp32. It is sometimes preferred that any differences in the amino acid sequences of the two proteins involve only conservative amino acid substitutions. Alternatively, changes such as the elimination of cysteine which alter the activity or stability of the protein may be preferred.

2) "Truncated pp32 peptides," which include fragments of either "pp32" or "pp32 muteins" that preferably retain either (i) an amino acid sequence unique to pp32, (ii) an epitope unique to pp32 or (iii) pp32 activity.

3) "pp32 fusion proteins" include heterologous polypeptides which are made up of one of the above polypeptides (pp32, pp32 muteins or truncated pp32 peptides) fused to any heterologous amino acid sequence.

"Unique" pp32 sequences, either amino acid sequences or nucleic acid sequences which encode them, are sequences which are identical to a portion of the sequence of a pp32 polypeptide, but which differ in at least one amino acid or nucleotide residue from the sequences of pp35, and pp42, and preferably, are not found elsewhere in the human genome. Similarly, an epitope is "unique" to pp32 polypeptides if it is found on pp32 polypeptides but not found on any members of the homologous gene family.

A composition comprising a selected component A is "substantially free" of another component B when component A makes up at least about 75% by weight of the combined weight of components A and B. Preferably, selected component A comprises at least about 90% by weight of the combined weight, most preferably at least about 99% by weight of the combined weight. In the case of a composition comprising a selected biologically active protein, which is substantially free of contaminating proteins, it is sometimes preferred that the composition having the activity of the protein of interest contain species with only a single molecular weight (i.e., a "homogeneous" composition).

As used herein, a "biological sample" refers to a sample of tissue or fluid isolated from a individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vivo cell culture constituents (including but not limited to conditioned medium resulting from the growth of cells in cell culture medium, putatively vitally infected cells, recombinant cells, and cell components).

"Human tissue" is an aggregate of human cells which may constitute a solid mass. This term also encompasses a suspension of human cells, such as blood cells, or a human cell line.

The term "coupled" as used herein refers to attachment by covalent bonds or by strong non-covalent interactions (e.g., hydrophobic interactions, hydrogen bonds, etc.). Covalent bonds may be, for example, ester, ether, phosphoester, amide, peptide, imide, carbon-sulfur bonds, carbon-phosphorus bonds, and the like.

An "epitope" is a structure, usually made up of a short peptide sequence or oligosaccharide, that is specifically recognized or specifically bound by a component of the immune system. T-cell epitopes have generally been shown to be linear oligopeptides. Two epitopes correspond to each other if they can be specifically bound by the same antibody. Two antibodies correspond to each other if both are capable of binding to the same epitope, and binding of one antibody to its epitope prevents binding by the other antibody.

The term "immunoglobulin molecule" encompasses whole antibodies made up of four immunoglobulin peptide chains, two heavy chains and two light chains, as well as immunoglobulin fragments. "Immunoglobulin fragments" are protein molecules related to antibodies, which are known to retain the epitopic binding speificity of the original antibody, such as Fab, F(ab)'$_2$, Fv, etc.

Two polypeptides are "immunologically cross-reactive" when both polypeptides react with the same polyclonal antiserum or the same monoclonal antibody.

General Methods

The practice of the present invention employs, unless otherwise indicated, conventional molecular biology, microbiology, and recombinant DNA techniques within the skill of the art. Such techniques are well known to the skilled worker and are explained fully in the literature. See, e.g., "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984), Sambrook, et al., "Molecular Cloning: a Laboratory Manual" (1989) and "Current Protocols In Molecular Biology," Ausubel, et al., eds., Current Protocols, 1994. Methods and discoveries related to this invention are also disclosed in U.S. application Ser. No. 07/561,989, filed Aug. 1, 1990 now abandoned, which is incorporated herein by reference.

DNA segments or oligonucleotides having specific sequences can be synthesized chemically or isolated by one of several approaches. The basic strategies for identifying, amplifying and isolating desired DNA sequences as well as assembling them into larger DNA molecules containing the desired sequence domains in the desired order, are well known to those of ordinary skill in the art. See, e.g., Sambrook, et ai., (1989); B. Perbal, (1984). Preferably, DNA segments corresponding to pp32 may be isolated individually using the polymerase chain reaction (M. A. Innis, et al., "PCR Protocols: A Guide To Methods and Applications," Academic Press, 1990). A complete sequence may be assembled from overlapping oligonucleotides prepared by standard methods and assembled into a complete coding sequence. See, e.g., Edge (1981) Nature 292:756; Nambair, et al. (1984) Science 223:1299; Jay, et al. (1984) J. Biol. Chem., 259:6311.

The assembled sequence can be cloned into any suitable vector or replicon and maintained there in a composition which is substantially free of vectors that do not contain the assembled sequence. This provides a reservoir of the assembled sequence, and segments or the entire sequence can be extracted from the reservoir by excising from DNA in the reservoir material with restriction enzymes or by PCR amplification. Numerous cloning vectors are known to those of skill in the art, and the selection of an appropriate cloning vector is a matter of choice (see, e.g., Sambrook, et al., incorporated herein by reference). The construction of vectors containing desired DNA segments linked by appropriate DNA sequences is accomplished by techniques similar to those used to construct the segments. These vectors may be constructed to contain additional DNA segments, such as bacterial origins of replication to make shuttle vectors (for shuttling between prokaryotic hosts and mammalian hosts), etc.

Procedures for construction and expression of mutant proteins of defined sequence are well known in the art. A DNA sequence encoding a mutant form of pp32 can be synthesized chemically or prepared from the wild-type sequence by one of several approaches, including primer extension, linker insertion and PCR (see, e.g., Sambrook, et al.). Mutants can be prepared by these techniques having additions, deletions and substitutions in the wild-type sequence. It is preferable to test the routants to confirm that they are the desired sequence by sequence analysis and/or the assays described below. Mutant protein for testing may be prepared by placing the coding sequence for the polypeptide in a vector under the control of a promoter, so that the DNA sequence is transcribed into RNA and translated into protein in a host cell transferred by this (expression) vector. The mutant protein may be produced by growing host cells transfected by an expression vector containing the coding sequence for the mutant under conditions whereby the polypeptide is expressed. The selection of the appropriate growth conditions is within the skill of the art.

According to the present invention, there are three related proteins which are expressed by mammalian lymphoblastoid cells as well as human lymphoid and epithelial tumor cells. These proteins may be found in tumor cells of epithelial tissues such as lung and bronchi and upper respiratory system, liver, biliary, exocrine pancreas, head and neck tissues including oropharynx, nasopharynx, and hypopharynx, gastrointestinal including esophageal, gastric, duodenal, jejunal, and colorectal; endocrine including thyroid adrenal, endocrine pancreatic, parathyroid, and hypophyseal, genitourinary including kidney, bladder, prostrate, seminal vesicles, uterus, cervix, fallopian tubes, breast, skin and adenexal structures; tumor cells of lymphoid and hematopoietic tissues including lymph nodes spleen, thymus, and bone marrow; tumor cells of mesenchymal tissues including skeletal muscle, cardiac muscle, smooth muscle, vascular tissues including endothelium, fibroconnective tissue, adipose tissue; and in tumor cells of the central nervous system tissues and peripheral nervous tissues. The proteins are related immunologically and have also been shown to generate overlapping sets of cleavage polypeptides. The proteins have been found to be phosphoproteins and are thus termed pp42, pp35, and pp32, based on their molecular weights. While the phosphoproteins were originally found in mouse cells, homologs have been found in human cells. The human homologs are immunologically cross-reactive with antibodies which are raised against the murine proteins. Thus, such antibodies can be used in the practice of the present invention's diagnostic method; alternatively antibodies raised against the human homologs can be used. Antibodies raised against synthetic or cleavage polypeptides can also be used.

As mentioned above the mammalian proteins of the present invention are believed to be phosphorylated. It has been found that two of the proteins, pp32 and pp35 are substrates for the enzyme casein kinase II in vitro. Casein kinase II, or NII kinase (Rose et al., 1981, J. Biol. Chem., vol. 256, pp. 7468-7477), was initially described as a cyclic nucleotide-independent, heparin-sensitive kinase utilizing both ATP and GTP as phosphate donors; recent work suggests that there may be a family of casein kinase II-like enzymes (Kishimoto et al., 1987, J. Biol. Chem., vol. 262, pp. 1344-1351). Several convergent lines of evidence imply that casein kinase II plays a key role in the processes of cell proliferation and differentiation. Firstly, casein kinase II levels are elevated both in transformed cells (Brunati, et al., 1986, J. Immunol. vol. 127, pp. 2496-2501; Prowald, et al., 1984, FEBS Letters, vol. 174, pp. 479-483) and during embryogenesis (Perez, et al., 1987, Eur. J. Biochem., vol. 170, pp. 493-498; Schneider, et al., 1986, Eur. J. Biochem., vol. 170, pp. 733-738; additionally, casein kinase II levels oscillate with the cell cycle (Carroll and Marshak, 1989, J. Biol. Chem., vol. 264, pp. 7345-7348) and undergo transient elevation during cell differentiation (Sommercorn and Krebs, 1987, J. Biol. Chem., vol. 262, pp. 3839-3843). Secondly, although casein kinase II substrates are not limited to the nucleus (Hathaway and Traugh, 1982, Curr. top. Cell. Reg., vol. 21, pp. 101-127; LeesMiller and Anderson, 1989, J. Biol. Chem., vol. 264, pp. 2431-2437; Wang, et al., 1986, Biochem. Biophys. Acta, vol. 888, pp. 225-236; Grande, et al., 1988, FEBS Letters vol. 232, pp. 130-134), an ever-lengthening list of proteins which coordinate nuclear function are major substrates for casein kinase II (Matthews and Huebner, 1984, Mol. Cell. Biochem., vol. 59, pp. 81-99; Pfaff and Anderer, 1988, Biochem. Biophys. Acta, vol 969, pp. 100-109) including RNA polymerases I and II (Duceman, et al., 1981, J. Biol Chem., vol. 256, pp. 10755-10758; Stetler and Rose, 1982, Biochemistry, vol. 21, pp. 3721-3728), DNA topoisomerases I and II (Durban, et al., 1985, EMBO J., vol. 4, pp. 2921-2926; Ackerman, et al., 1985, Proc. Natl. Acad. Sci., USA vol. 82, pp. 3164-3168), high mobility group protein 14 (Walton, et al., 1985, J. Biol Chem., vol. 260, pp. 4745-4750) and C-proteins of heterogenous nuclear ribonucleoprotein particles (Friedman, et al., 1985, Biochem. Biophys. Acta, vol. 847, pp. 165-176; Holcomb and Friedman, 1984, J. Biol. Chem., vol. 259, pp. 31-40). Thirdly, growth factors such as insulin, epidermal growth factor, and insulin-like growth factor 1 stimulate casein kinase II activity in quiescent cells (Sommercorn, et al., 1987, Proc. Natl. Acad. Sci., USA, vol. 84, pp. 8834-88389; Klarlund and Czech, 1988, J. Biol. Chem., vol. 263, pp. 15872-15875; Ackerman and Osheroff, 1989, J. Biol. Chem., vol. 2647, pp. 119580-11965). It appears that casein kinase II-mediated phosphorylation must in some way modulate those cellular functions forming the infrastructure of proliferation and differentiation. Whether pp42 is phosphorylated has not yet been determined, although pp42 is referred to herein as a phosphoprotein.

The 35 kD phosphoprotein of the present invention binds to myosin filaments. This property can be used as a means of purifying the phosphoprotein from other cellular proteins. The other proteins of the invention, of molecular weights 32 kD and 42 kD, do not bind to myosin, thus it appears that the myosin-binding domain is not present or accessible in these proteins. However, as discussed below, peptide mapping has indicated that other regions of the 35 kD structure are shared by the 32 and 42 kD proteins. This is confirmed by the fact that affinity purified antibodies which were raised against native pp35 are able to bind to both pp32 and murine pp42. No human homolog of murine pp42 has yet been observed.

According to the present invention, molecular weight is an important identifying property of the phosphoproteins. The molecular weights are determined by SDS-polyacrylamide gel electrophoresis (SDS-PAGE). Such techniques are well known in the art. See Laemmli, 1970, Nature, vol. 227, pp. 680-685.

The amino acid sequences of proteolytic peptides pp35 were experimentally determined. These exactly correspond to the predicted amino acid sequence of pp32. The predicted amino acid sequence of a portion of pp32 is shown in FIG. 9. This sequence or the sequences of FIG. 10 can be used to synthesize polypeptides which can be used to raise antibodies as is known in the art. Alternatively, synthetic polypeptides can be used (as can the whole protein) to compete with proteins present in a biological source for antibody binding. Such competition can be used to assure that antibody binding is specific and can also be used as a means of quantitating the amount of antigen present in a biological sample.

According to the present invention, the phosphoproteins can be isolated from any convenient mammalian source. One particularly convenient source is a mammalian lymphoblastoid cell line. A particularly preferred cell line is the murine cell line $A_{20}$. See Kim, et al., 1979, J. Immunol., vol. 129, pp. 549-554. This cell line is available from the American Type Culture Collection in Rockville, Md. Phosphoproteins pp35 and pp32 can be collected form the nucleus of lymphoblastoid cell lines. Mammalian cell lines can be cultured according to methods known in the art using culture media and conditions which are well known.

Antibodies according to the present invention may be monoclonal or polyclonal. If polyclonal antibodies are employed, it is preferred that they be affinity purified to render them monospecific. As mentioned above, polyclonal antibodies which are raised against pp35 are also immunoreactive with pp32 and pp42. Of course, since each of the proteins contains unique peptide sequences, it is likely that monoclonal antibodies could be raised with would not cross-react with the other members of the phosphoprotein family. That is to say that the peptide mapping data make it likely that there are unique as well as shared epitopes on each of the members of the phosphoprotein family.

Some antibodies according to the present invention are immunoreactive with the native forms of the phosphoproteins. Thus, the proteins need not be denatured in order to render them suitable binding partners for the antibodies. However, the antibodies may be used to detect proteins in the denatured form, such as in Western blots and immunohistochemistry.

Other antibodies according to the invention are produced by immunizing experimental, antibody-producing animals with an immunogen which comprises a polypeptide. The polypeptide contains amino acid sequences corresponding to the phosphoproteins of the present invention, such as those shown in FIG. 9. The immunogen may also contain other proteins such as keyhole limpet hemocyanin (KLH) which can be used to stimulate the animal to produce an immune response to a polypeptide which may be too small to do so on its own. Alternatively, the immunogen may comprise all or a portion of another protein which is attached to the polypeptide and produced from a fusion gene. Such fusions may be used to express the polypeptide in bacterial or animal cells as is known in the art.

Methods have been developed to achieve preparations of apparent homogeneity of the phosphoproteins of the present invention. The methods involve lysis of the cells in a detergent and low-ionic strength buffer. Suitable detergents include Triton X-100 and other non-ionic detergents. The salt concentration of the buffers should preferably be in the range of 5–50 mM. Purification of a crude cell lysate can be accomplished by sequential chromatography on DEAE-cellulose, HPLC anion-exchange, and HPLC hydroxylapatite columns. Fractions which are eluted from the chromatographs can be assessed by SDS-PAGE and by Western blotting using anti-pp35, for example. If desired an additional purification step can be employed in the purification of pp35 which involves the co-precipitation with cross-linked myosin filaments. Rabbit skeletal muscle is a suitable source of myosin. The phosphoproteins can be eluted from the myosin by extraction with 1M KCl.

A substantially purified preparation of mammalian protein according to the present invention contains greater than about 75% of the desired phosphoprotein. Preferably the preparation contains greater than about 90% of the desired phosphoprotein. Most desirably the preparation contains at least about 95% of the desired phosphoprotein.

Also contemplated by the present invention as a diagnostic and prognostic tool are nucleic acid probes. Like the antibodies of the present invention, they can be used to quantitate the expression of gene products from the genes encoding pp32, pp35, and pp42. Gene products according to the invention include messenger RNA as well as protein or phosphoprotein. The probes are complementary to the mRNA sequences from which the three phosphoproteins are translated. Probes may also be used which vary slightly from the sequence of a particular phosphoprotein gene. For example, a probe may be derived from the murine phosphoprotein sequence and be useful for hybridization to human and other mammalian species genes. Alternatively, a probe may represent an allelic or polymorphic variant of a sequence. However, all probes must be sufficiently homologous to the phosphoprotein gene being probed to hybridize under the conditions of the well known techniques of Northern, Southern, and in situ hybridization. Particularly preferred probes will hybridize under stringent conditions, e.g., washing in 0.2×SSC (0.03M NaCl+0.003M trisodium titrate) at 55° for Northern or 65° for Southern hybridization.

Nucleic acid probes are generally labeled with a radioactive moiety. Alternatively, they can be labeled with a fluorescent moiety or an enzyme which can cause a chromogenic substrate to change color. Nucleic acid probes are generally useful between about 15 and 1500 bases. Preferred probes usually contain 200–300 bases. Clones of the complete coding sequence may also be used. Such probes may be synthesized using the sequences disclosed in FIGS. 9 and 10. Alternatively, sequences shown in FIGS. 9 and 10 can be used as a probe to detect other pp32 sequences or pp35 or pp42 sequences. These latter sequences can be used to derive probes for diagnostic uses.

Particularly preferred nucleic acid probes will have a sequence that is unique to pp32. Such sequences include sequences of at least 18 consecutive nucleotides from FIG. 10, where the sequence preferably differs from the sequence of pp35 mRNA by at least 8 nucleotides within the contiguous sequence. As the expression of pp35, pp32 and pp42 has been discovered to be elevated in relation to the degree of malignancy of a lymphoid or epithelial tumor, the steady state levels of the corresponding mRNA are almost certainly elevated also in such tumors. Particular methods for quantitating mRNA in tissue samples are known in the art, and any such method can be employed. It is possible that the elevated levels of the nuclear phosphoproteins of the invention are due to gene amplification. The probes of the present invention can be used in Southern hybridizations to detect such amplified genes.

Quantitative polymerase chain reaction (PCR) can be used to determine the steady state amount of mRNA in a tissue. See Wang, et al., PNAS, vol. 86, pp. 9717–21, 1989. In order to practice this latter method to quantitate the amount of mRNA encoding the phosphoproteins of the invention, primers are used which are derived from the phosphoprotein gene sequences. As is known in the art, primers are complementary to opposite strands of a DNA duplex and flank a region of DNA to be amplified. To measure mRNA amounts cDNA is first made by reverse transcription and the cDNA is then amplified. PCR can also be used to quantitate genomic sequences which may be amplified in malignant tissues.

The diagnostic methods of the present invention are conveniently carried out using standard histological sections, such as paraffin-embedded sections. Either lymphoid or epithelial tissue can be used. Any of the preparations of antibodies which are reactive with pp32, pp35 and/or pp42 can be used to immunostain the histological sections. Immunostained sections can be analyzed to determine the percentage of cells which immunostain with the antibodies. As shown below in Table 1, the samples derived from increasingly more malignant tissues showed increasing percentages of immunostained cells. In the case of intermediate grade lesions, 60–70% of the cells are positive for the antibody stain. In the case of high grade lesions, greater than 90% of the cells are positive for the antibody stain.

Alternatively, in the case of staining with an anti-pp35 preparation, the localization of the immunostaining within the cells can be determined. Whereas in normal lymphoid tissue staining is restricted to germinal centers and small paracortical foci, in low grade lesions the staining is more intense and more widely distributed. In intermediate and some high grade lesions (diffuse large cell malignant lymphoma (diffuse histiocytic lymphoma)) the staining is in both the nucleus and the cytoplasm. In other high grade lesions (small non-cleaved cell malignant lymphoma (diffuse undifferentiated lymphoma)) the staining is solely in the nucleus. In the case of pp32 staining, normal tissues stain in the germinal centers and paracortex, whereas in the malignant tissues the staining is in the nucleus. Staining of pp32 does not appear in the cytoplasm in any of the lesions examined.

Cloning, analysis of pp32 sequence, and transfection studies have provided a major window into pp32 structure and function. pp32 cDNA encodes a 28.6 kDa protein (see, e.g., SEQ ID No: 2); the N-terminal approximately two-thirds predicts an amphipathic alpha helix containing two possible nuclear localization signals and a potential leucine zipper motif. Preferable nucleotide probes are directed to this region (see FIG. 10, bases 1–550) or to the 3' untranslated region (see FIG. 10, from base 842 to the end). The C-terminal third is exceptionally acidic, comprised of approximately 70% aspartic and glutamic acid residues; the predicted pI of human pp32 is 3.81. Human and murine pp32 cDNA's are 88% identical; the predicted proteins are 89% identical and 95% similar. While superficially, pp32 structure might suggest a transcription factor with leucine zipper and acidic domain, there is substantial circumstantial evidence to the contrary: when expressed in normal cells, pp32 levels approach $10^6$ copies per cell; the half-life of pp32 protein is approximately three days; pp32 does not bind DNA; and additional functions have been identified for pp32.

In yet another embodiment of the present invention, the immunostaining can be analyzed to determine the intensity of staining. Increasing intensity of staining correlates with increasing malignant potential.

Biological Activity and Therapy pp32 is found in normal cells with stem cell properties and is overexpressed in many neoplastic cells. For example, two related nuclear phosphoproteins, pp32 and pp35, have been identified in a murine neoplastic B-lymphoblastoid cell line $A_{20}$. The pattern of protein expression in vivo and in cell lines suggests a dual association: with self-renewing stem-like cell populations and also with neoplastic cells. Whereas the majority of the neoplastic tissue culture cells stain positively for pp35 and pp32, the distribution in normal tissues is highly restricted. Both intestinal crypt cells and basal cells of squamous epithelium stain positively with great specificity; these cell populations are well known to contain the cells which continually renew their respective tissues (i.e., stem cells). The initial antibodies to murine pp32 and pp35 react well with their human counterparts. Additional small-scale studies, undertaken in prostate cancer and non-Hodgkin's lymphoma, indicate that increased frequency and intensity of pp32 staining in human cancers correspond to increased malignant potential.

Consistent with previous observations in vivo that pp32 is found in self-renewing cells but not in their terminally differentiated progeny, pp32 RNA levels are down-regulated during TPA-induced differentiation of HL-60 cells. In co-transfection experiments, pp32 inhibited the ability of ras and myc to transform rat embryo fibroblasts. AT3.1 rat prostatic carcinoma cells stably transfected with human pp32 cDNA are resistant to programmed cell death induced by 5-fluorouracil, ionomycin, and thapsigargin. These results suggest that pp32 may play a key role in self-renewing cell populations where it may act to limit their sensitivity to transformation and apoptosis.

Drug Screening Assays

Drugs which inhibit the biological activity of pp32 are good candidates for anti-tumor drugs, because they affect one of the steps that leads to uncontrolled proliferation or a continuous increase in cell number. Therefore, the present invention provides a screening assay which will help identify anti-tumor drugs, when the results of this screening assay are considered in conjunction with the results from other model systems, such as in vivo tumor growth assays, clonagenic assays and in vitro cytotoxic tests. While any assay which tests inhibition of a biological activity of pp32 may be used as a screening tool, three preferred screens are described in greater detail below.

pp32 possesses three biologic activities which may be relevant both to stem cells and to cancer: (1) inhibition of co-transformation by two oncogenes, such as ras and myc; (2) partial protection against programmed cell death; and (3) modulation of nuclear shape and size. The molecular bases of these functions are completely unknown. Each of these functions has been defined wholly or in part through transient or stable transfection with pp32 expression constructs.

Stem cells, particularly those in renewing tissues must be resistant to neoplastic transformation. Indeed, special mechanisms have been proposed to preserve the integrity of stem cell populations (Cairns, J. (1975) "Mutation Selection and the Natural History of Cancer," Nature, 255: 197–200.). The relationship of cellular oncogenes to multi-step carcinogenesis was first demonstrated in 1983 by Land, Pararia, and Weinberg (Land, et al. (1983) "Cellular Oncogenes and Multistep Carcinogenesis," Science, 222:771–778; Land, et al. (1983) "Tumorigenic Conversion of Primary Embryo Fibroblasts Requires At Least Two Cooperating Oncogenes," Nature, 304:596–602) when they showed that primary cultures of rat embryo fibroblasts require both ras and myc for tumorigenic conversion. Six molecules have been subsequently shown to inhibit transformation by ras and myc in this system, although the mechanisms are not fully understood: wild type p53 (Eliyahu, et al., "Wild-type p53 can inhibit oncogene-mediated focus formation," Proc. Natl. Acad. Sci. USA, 86:8763–8767, 1989); c-jun (Ginsberg, et al., "Transfected mouse c-jun can inhibit transformation of primary rat embryo fibroblasts," Oncogene, 6: 669–672, 1991); B-myc (Resar, et al., "B-Myc inhibits neoplastic transformation and transcriptional activation by c-Myc," Mol. Cell. Biol., 13: 1130–1136, 1993.22); E1B type 5 (van den Heuvel, et al., "Large E1B proteins of adenovirus types 5 and 12 have different effects on p53 and distinct roles in cell transformation," J. Virol., 67: 5226–5234, 1993); hsc70, a rat heat-shock cognate (Yehiely, et al., "The gene for the rat heat-shock cognate, hsc70, can suppress oncogene-mediated transformation," Cell. Growth Diff., 3: 803–809, 1992); and max (Makela, et al., "Alternative forms of max as enhancers or suppressors of myc-ras cotransformation," Science, 256: 373–377, 1992). We have discovered that pp32 is also one of the handful of molecules capable of inhibiting ras-myc mediated transformation of rat embryo fibroblasts. In normal cells, pp32 performs a critical function of helping to maintain stem cell integrity by suppressing transforming stimuli analogous to the ras-myc model.

Inhibition of Co-Transformation

Cell lines transfected with pp32 are resistant to co-transformation by a combination of two oncogenes or mutated tumor suppressor genes, for example ras and myc, as described below in Example 17. Drug candidates are considered positive if, when added to a ras-myc transformation assay along with a pp32 expression vector, the drug stimulates an increase in the number of transformed cells over the number observed for the triply-transfected cells in the absence of the drug.

Figure 17:
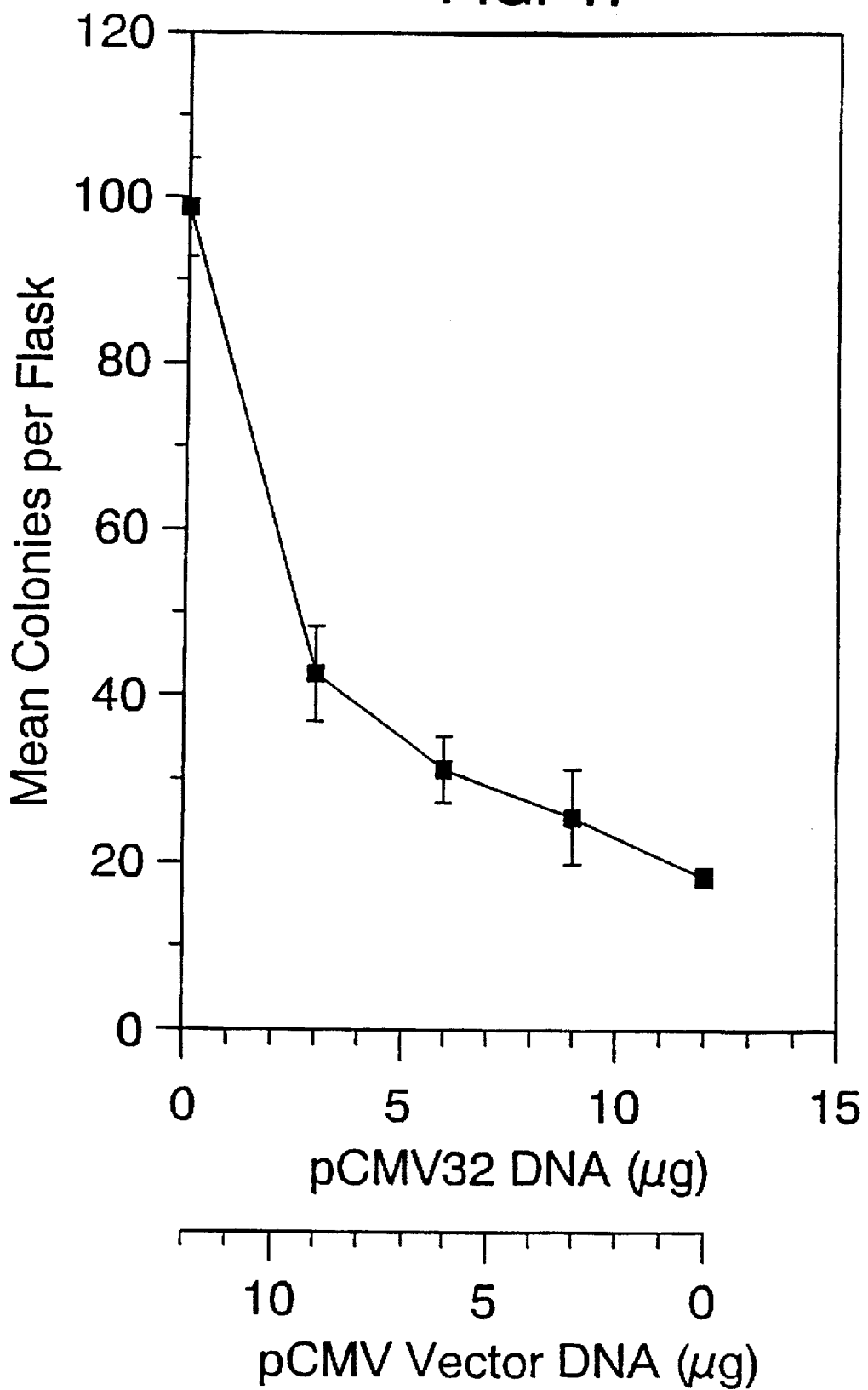
FIG. 17 shows the dose-dependent inhibitory effect of pp32 on transformation of rat embryo fibroblasts by ras and myc.

All measurements should preferably be performed at least in triplicate to permit standard deviations to be calculated; experiments will preferably produce 75–1130 colonies per flask in ras-myc controls in order to be considered valid. (In the co-transformation experiment, myc may be replaced by jun, adenovirus E1A or a mutant form of p53, or another mutant tumor suppressor gene that gives comparable levels of transformation in the controls. Similar substitution of ras with other oncogenes is permissible, so long as controls show levels of transformation comparable to those obtained with ras and myc.) As can be seen in FIG. 17, retention of full transformation inhibitory potency will be obvious. The more difficult situation to assess will be partial inhibition. Reductions will usually have to achieve statistical significance using a standard statistical measure such as a Student's t test. Any untransformed cell line that is susceptible to co-transformation may be used in this assay. We have found primary cultures of rat embryo fibroblasts to be particularly preferable as the cell for transformation due to reduction in variability of the assay.

pp32 and Programmed Cell Death.

The balance between proliferation and programmed cell death is thought to be a normal feature of tissue growth regulation (Gerschenson, et al. (1991) "Apoptosis and Cell Proliferation are Terms of the Growth Equation," in *Apoptosis: The Molecular Basis of Cell Death*, J. Inglis, et al. eds., Cold Spring Harbor, N.Y.: Cold Spring Harbor Laboratory Press, pp. 175–192; Kerr, et al. (1991) "Definition and Incidence of Apoptosis: An Historical Perspective," in *Apoptosis: The Molecular Basis of Cell Death*, J. Inglis, et al. eds., Cold Spring Harbor, N.Y.: Cold Spring Harbor Laboratory Press, pp. 5–29. However, when abnormally low, programmed cell death can contribute to tumorigenesis through inappropriate increases in cell number without increases in proliferative rate (Cope, et al. (1991) "Carcinogenesis and Apoptosis: Paradigms and Paradoxes in Cell Cycle and Differentiation," in *Apoptosis: The Molecular Basis of Cell Death*, J. Inglis, et al. eds., Cold Spring Harbor, N.Y.: Cold Spring Harbor Laboratory Press, pp. 61–86). Just as stem cell populations must preserve their integrity with respect to transformation, they must also resist cell programmed cell death.

Programmed cell death (Martin, et al. (1994) "Dicing With Death: Dissecting the Components of the Apoptosis Machinery," *Trends Biochem. Sci.*, 19:26–30) occurs in a number of developmental and other settings. For example, when tissues involute due to withdrawal of hormonal stimulation, they do so through a process of programmed cell death (Buttyan, R. (1991) "Genetic Response of Prostate Cells to Androgen Deprivation: Insights Into the Cellular Mechanism of Apoptosis," in *Apoptosis: The Molecular Basis of Cell Death*, J. Inglis, et al. eds., Cold Spring Harbor, N.Y.: Cold Spring Harbor Laboratory Press, pp. 157–173); only the stem cells persist to repopulate the tissue with the return of hormonal stimulation. Despite much study, the mechanism whereby certain stimuli lead to characteristic morphologic changes and DNA fragmentation remain a subject of debate. Certain key observations, however, have been made. In appropriate growth-related stimuli can lead to programmed cell death; when myc is expressed in quiescent cells, such as cells undergoing serum starvation, programmed cell death can result (Martin, et al., 1994; Wagner, et al. (1993) "Myc-Mediated Apeptosis is Blocked By Ectopic Expression of Bcl-2," *Mol. Cell. Biol.*, 13:2432–2440).

BCL2 is a mitochondrial membrane (Hockenbery, et al. (1991) "BCL2 Protein is Topographically Restricted in Tissues Characterized by Apoptotic Cell Death," *Proc. Natl. Acad. Sci., U.S.A.*, 88:6961–6965) and perhaps nuclear membrane (de long, et al. (1994) "Subcellular Localization of the bcl-2 Protein in Malignant and Normal Lymphoid Cells," *Cancer Res.*, 54:256–260) protein which protects against programmed cell death, although the mechanism is unclear. BCL2 is localized to stem cell areas in tissues where apoptotic death occurs, such as basal cells in squamous epithelium and intestinal crypt cells (Hockenbery, et al., 1991). BCL2 extends the lives of SF9 insect cells when overexpressed in baculovirus (Alnemri, et al. (1992) "Overexpressed Full-Length Human BCL2 Extends the Survival of Baculovirus Infected Sf9 Insect Cells," *Proc. Natl. Acad. Sci., U.S.A.*, 89:7295–7299), and protects against myc-mediated apoptosis (Wagner, et al., 1993).

pp32 also preserves stem cell integrity by contributing to resistance to programmed cell death, as shown in Example 18, below. Like BCL2, pp32 both localizes to compartments where stem cells reside in vivo and protects against at least one form of programmed cell death. pp32 transfectants incubated in drag beyond 48 h will being to die off through an apoptotic mechanism, as confirmed by pulsed field gel electrophoresis analysis of double-stranded DNA breaks. While continued expression of pp32 during extended drug treatment has yet to be verified, the data strongly suggest that pp32 and BCL-2 act through distinct mechanisms.

Protection from Programmed Cell Death.

Assays of candidate drugs for interference with pp32-mediated inhibition of programmed cell death will determine the relative protection for pp32-transfected cells achieved by the candidate drug at a fixed dose of inducers of programmed cell death, such as 5-fluorouracil, ionomycin, or thapsigargin, as compared to BCL-2, and vector controls. (See Example 18 for a typical procedure.) Data may be expressed as the ratio of the clonogenic potential of, for example, AT3.1 cells expressing pp32 in the presence of the candidate to AT3.1 cells expressing pp32 in the absence of the candidate drug. When differences are identified, they may be confirmed by dose-response analysis, analysis of dependence on length of drag exposure, and analysis of DNA for double-stranded breaks. These confirmatory studies should permit clear distinction among those drugs which affect pp32-mediated protection from programmed cell death and those which do not, since intact pp32 yields distinct dose-response curves, protects against double-stranded DNA breaks, and loses its protective effect after 48 h of drug exposure.

pp32 and Nuclear Grade.

Nuclear morphology often undergoes profound change following malignant transformation. Malignant nuclei are often misshapen, and the chromatin shows coarse areas of condensation and clearing, rather than the more usual finely stippled pattern. Pathologists often make use of nuclear grading in an attempt to assess the degree of malignancy of a given patient's tumor. While nuclear grading is potentially useful, it can be subjective and prone to interobserver variation. In the early 1980's, nuclear roundness measurements were applied to human prostatic carcinoma in an attempt to quantify nuclear grade through image analysis (Diamond, et al (1982) "A New Method To Assess Metastic Potential of Human Prostate Cancer: Relative Nuclear Roundness," *J. Urol.*, 128:729–734; Diamond, et al. (1982) "Computerized Image Analysis of Nuclear Shape As a Prognostic Factor for Prostatic Cancer," *The Prostate*, 3:321–332); the results were that nuclear roundness measurements appears superior to the Gleason grading system in at least one study assessing prostate cancer (Epstein, et al.

(1984) "Nuclear Roundness Factor. A Predictor of Progression in Untreated Stage A2 Prostate Cancer," *Cancer*, 54:1666–1671). Subsequent studies extended the approach by applying additional nuclear measurements (texture, ellipicity, etc.) to renal cell cancer (Murphy, et al. (1990) "Nuclear Shape Analysis for Assessment of Prognosis in Renal Cell Carcinoma," *J. Urol*, 143:1103–1107), medullary carcinoma of the thyroid (Galera, et al. (1990) "Cytophotometric DNA Measurements in Medullary Thyroid Carcinoma," *Cancer*, 65:2255–2260), dysplastic nevi (Fleming, et al. (1990) "Image Analysis Cytometry of Dysplastic Nevi," *J. Invest. Dermatol.*, 95:287–291), Wilm's tumor (Partin, et al. (1990) "Nuclear Morphometry as a Predictor of Response to Therapy in Wilms Tumor: A Preliminary Report," *J. Urol.*, 144:952–954), breast cancer (Dawson, et al. (1991) "Nuclear Grading of Breast Carcinoma by Image Analysis. Classification by Multivariate and Neural Network Analysis,: *Am. J. Clin. Pathol*, 95:S29–S37; Pienta, et al. (1991) "Correlation of Nuclear Morphometry with Progression of Breast Cancer," *Cancer*, 68:2012–2016), head and neck squamous cancers (Briggs, et al. (1992) "Nuclear Morphometry for Prediction of Metastatic Potential in Early Squamous Cell Carcinoma of the Floor of the Mouth," *Arch. Otolaryngol Head. Neck. Surg.*, 118:531–533), colorectal cancer (Hill, et al. (1989) "The Proportion of Stem Cells in Murine Tumors," *Int. J. Radiat. Oncol. Biol. Phys.*, 16:513–518), pancreatic cancer (Bickaert, et al. (1992) "Computerized Morphonuclear Characteristics and DNA Content of Adenocarcinoma of the Pancreas, Chronic Pancreatitis, and Normal Tissues: Relationship with Histopathologic Grading," *Hum. Pathol.*, 23: 1210–1215; Weger, et al. (1992) "Morphometry and Prognosis in Cancer of the Pancreatic Head," *Pathol. Res. Pract.*, 188:763–769), and ovarian cancer (Drescher, et al. (1992) "Prognostic Significance of DNA Content and Nuclear Morphology in Borderline Ovarian Tumors," *Gynecol. Oncol.*, 48:242–246). Although the results were mixed, the overwhelming majority of studies showed correlations of deteriorating nuclear morphology with increasing malignancy.

Initial observations suggested that increases in pp32 content paralleled increases in malignancy and, by extension, nuclear alternations but did not suggest a causal relationship. Recombinant pp32 overexpression leads to nuclear changes characteristic of high-grade malignancy including increased nuclear size with course areas of chromatin condensation and clearing.

Candidate drugs are screened by culturing cells transfected with pp32 in the presence and absence of the drug, then comparing the nuclei of cells in the two cultures. The effect of pp32 on nuclear morphology is usually determined visually by direct observation of Papanicolaou-stained cell preparations. Cultures wherein >60% of cells display nuclei with diameters (measured with a reticle) >1.5 times the mean diameter of control cultures infected with wild-type baculovirus are typically considered positive for malignant nuclear morphology; such cells will also display finely dispersed chromatin. The potential for subjectivity may be addressed through quantitative image analysis and size measurements (e.g. Coulter counter analysis of cells or isolated nuclei).

Therapy Based on pp32

Because of the profound clinical importance of prostate cancer, pp32 expression has been studied in this disease. Prostate cancer cells are slow-growing and are thus relatively insensitive to agents which depend upon cell proliferation to exert their effects. In contrast, pp32 is not directly associated with proliferation, but rather with the failure of prostate cancer cells to die; pp32 may thus address a major problem with androgen ablation therapy, the frequent outgrowth of androgen-independent prostatic cancer cells.

The relationship between pp32 expression and self-renewing cell populations has been explored using androgen to manipulate hormonally-dependent rat tissues in a highly physiologic model in vivo. In the intact prostate, pp32 protein and mRNA were found primarily in the peripheral regions thought to be roughly equivalent to intestinal crypts in that they contain the self-renewing cell populations; overall, approximately 15% of epithelial cells stained positively for pp32. In contrast, virtually all epithelial cells in the involuted prostate of castrated rats were positive for pp32 mRNA by in situ hybridization, and approximately 55% were antibody-positive. Calculations of epithelial cell mass suggested that the residual pp32-positive population in castrates was roughly equivalent, numerically, to the pp32-positive population in the intact gland. Simply stated, pp32 appeared to mark the stem-like cells capable of renewing the gland upon subsequent androgen stimulation. When androgen was administered to castrated rats, the pp32-positive cells appeared to dilute out to their original proportion and re-achieve their original anatomic distribution. Consistent with the dual finding of pp32 in stem-like self-renewing cell populations and cancer, pp32 levels and the number of pp32-positive cells increased with increasing Gleason grade in human prostate cancer.

Androgen ablation is effective during an initial response period, where androgen dependent prostatic cancer cells die via programmed cell death. Several investigators have proposed potentiation of programmed cell death as a therapeutic target. According to this scheme, programmed cell death of otherwise resistant prostate cancer cells could be potentiated either by increasing entry into the pathway, or by interfering with endogenous mechanisms of resistance to apoptosis (programmed cell death).

Ablation of pp32 in prostate cancer cell lines through knockout mutations or through antisense approaches will either directly result in cell death or will potentiate the effects of other agents. Many conventional chemotherapeutic agents ultimately kill cells through programmed cell death. Ablation of pp32, a molecule which confers resistance to programmed cell death, can therefore be reasonably expected to sensitize cells to conventional chemotherapeutic agents by permitting increased entry into programmed cell death pathways. Therapy which includes ablation of pp32 may be expected to be similarly effective in treatment of other tumors containing cells showing increased pp32 expression.

Antisense Therapy

One approach to therapy of human cancer cells is to introduce vectors expressing antisense sequences to block expression of pp32. In one embodiment of this invention, a method is provided for inhibiting proliferation of cells characterized by potential for continuous increase in cell number, e.g., neoplastic cells, which comprises obtaining a DNA expression vector containing a cDNA sequence having the sequence of human pp32 mRNA which is operably linked to a promoter such that it will be expressed in antisense orientation, and transforming the neoplastic cells with the DNA vector. The expression vector material is generally produced by culture of recombinant or transfected cells and formulated in a pharmacologically acceptable solution or suspension, which is usually a physiologically compatible aqueous solution, or in coated tablets, tablets, capsules, suppositories, inhalation aerosols, or ampules, as described in the art, for example in U.S. Pat. No. 4,446,128, incorporated herein by reference.

The vector-containing composition is administered to a mammal in an amount sufficient to transfect a substantial portion of the target cells of the mammal. Administration may be any suitable route, including oral, rectal, intranasal or by intravesicular (e.g. bladder) instillation or injection where injection may be, for example, transdermal, subcutaneous, intramuscular or intravenous. Preferably, the expression vector is administered to the mammal so that the tumor cells of the mammal are preferentially transfected. Determination of the amount to be administered will involve consideration of infectivity of the vector, transfection efficiency in vitro, immune response of the patient, etc. A typical initial dose for administration would be 10–1000 micrograms when administered intravenously, intramuscularly, subcutaneously, intravesicularly, or in inhalation aerosol, 100 to 1000 micrograms by mouth, or $10^5$ to $10^{10}$ plaque forming units of a recombinant vector, although this amount may be adjusted by a clinician doing the administration as commonly occurs in the administration of other pharmacological agents. A single administration may usually be sufficient to produce a therapeutic effect, but multiple administrations may be necessary to assure continued response over a substantial period of time.

Further description of suitable methods of formulation and administration according to this invention may be found in U.S. Pat. Nos. 4,592,002 and 4,920,209, incorporated herein by reference.

The following examples are merely illustrative of the invention and do not limit the invention.

EXAMPLE 1 pp35 Co-Sediments with Cross-Linked Myosin pp35 co-sedimented with rabbit skeletal muscle myosin filaments. While this suggested a means of affinity purification, it required a convenient means to separate pp35 from myosin. Since amine cross-linkers uniformly inactivated the ability of myosin to bind pp35, myosin filaments were disulfide-cross-linked using o-phenanthroline and copper. Unlike native filaments, which disassemble in increasing salt concentrations, the cross-linked filaments permitted recovery of pp35 by elution in 1M KCl. FIG. 1 Lanes B and C show the respective pellet and supernatant resulting from incubation of cross-linked myosin in $A_{20}$ lysate, while lanes D and E respectively show the residual pellet and the material eluting from the myosin in 1M KCl. The eluate contained a Coomassie-stainable 35 kDa band. pp35 was further purified by HPLC anion exchange chromatography, excised from a Laemmli gel (Laemmli, 1970, Nature, vol. 227, pp. 680–685, and used to raise polyclonal antibodies, designated anti-pp35d (d designates that the immunogen was denatured).

Myosin Affinity Purification of pp35. Rabbit skeletal muscle myosin, was purified as described (Margossian, et al., 1982, Methods Enzymol., vol. 895, pp. 55–71) using DEAE cellulose chromatography in pyrophosphate buffers to remove the contaminating C-protein. For cross-linking, purified rabbit skeletal muscle myosin in 0.6M KCl, 50 mM potassium phosphate, pH 6.5 at 15–20 mg/ml was diluted to 1 mg/ml in 10 mM sodium phosphate, pH 7.5 and incubated at 4° for 15 min. After incubation, the mixture was adjusted to 0.1 mg/ml myosin and brought to final concentrations of 1.7 mM (Cu(O-phenanthroline)$_2$, and 1% TRITON X-100, pH 7.5. Generally, a lysate prepared from $A_{20}$ cells (8 mg total protein, see below) was incubated with 1 mg of cross-linked myosin for 30 min. at 4°. The myosin was pelleted at 16,000×g for 1 min., the supernatant removed, and the pellet washed three times in lysis buffer. The pellet was then resuspended in lysis buffer containing 1M KCl and incubated at 4° for 15 min. After incubation, the myosin was again pelleted. The material eluted from cross-linked myosin was further purified by DEAE cellulose chromatography. The 1M KCl extract was dialyzed into 20 mM KCl, 5 mM sodium phosphate, pH 7.6, with 0.1 mM henylmethylsulfonyl fluoride, 1 mM 2-mercaptoethanol, and 0.1% Triton X-100. The extract was loaded onto a 0.9×8 cm DEAE cellulose column equilibrated in the same buffer, which was then undercut with 0.3M KCl and eluted with 0.5M KCl in the same buffer. Following purification, the eluted material was re-dialyzed into the starting buffer and stored at 4°. A typical preparation yielded approximately 100 µg of total product, including impurities, from approximately $2.5 \times 10^9$ cells grown in 1l of medium.

Antibody to denatured pp35 was raised in rabbits and affinity-purified. Initially, antigen was purified by electroelution from SDS-polyacrylamide gels essentially as described (Knowles and Bologna, 1983). To localize the band, 85 µg of pp35 kDa protein in 5 mM sodium phosphate, 20 mM KCl, 0.1% Triton X-100, pH 8.5, was reacted with a 100-fold molar excess of dansyl chloride. Derivatized protein was mixed with unreacted 35 kDa protein at a 1:9 ration (w/w) and the electrophoretic bands visualized under ultraviolet light. Protein was eluted from the gel slices using a commercial apparatus (Isco Corp., Lincoln, Neb.). Initially, each of the three female New Zealand white rabbits was injected at six subcutaneous sites with 50 µg of 35 kDa protein emulsified in phosphate-buffered saline containing 2% squalene, 50 µg trehalose dimycolate and 100 µg monophosphoryl lipid A (Ribi Immunochem Research, Inc., Hamilton, Mont.). Each rabbit received a total volume of 1.8 ml. On day 19, the animals were boosted in similar fashion. On day 42, two of the rabbits were again boosted with 125 µg of protein directly excised from stained, neutralized gels and emulsified in the same adjuvant system. One rabbit responded, as determined by strong reactivity against the homologous antigen in a Western blot. This animal was bled on day 100. The resulting antiserum was purified on a column of pp35 kDa coupled to Reacti-Gel 6X (Pierce Chemical Co., Rockford, Ill.) with the same elution protocol as described above.

EXAMPLE 2

Identification of pp42 and pp32

Figure 2:
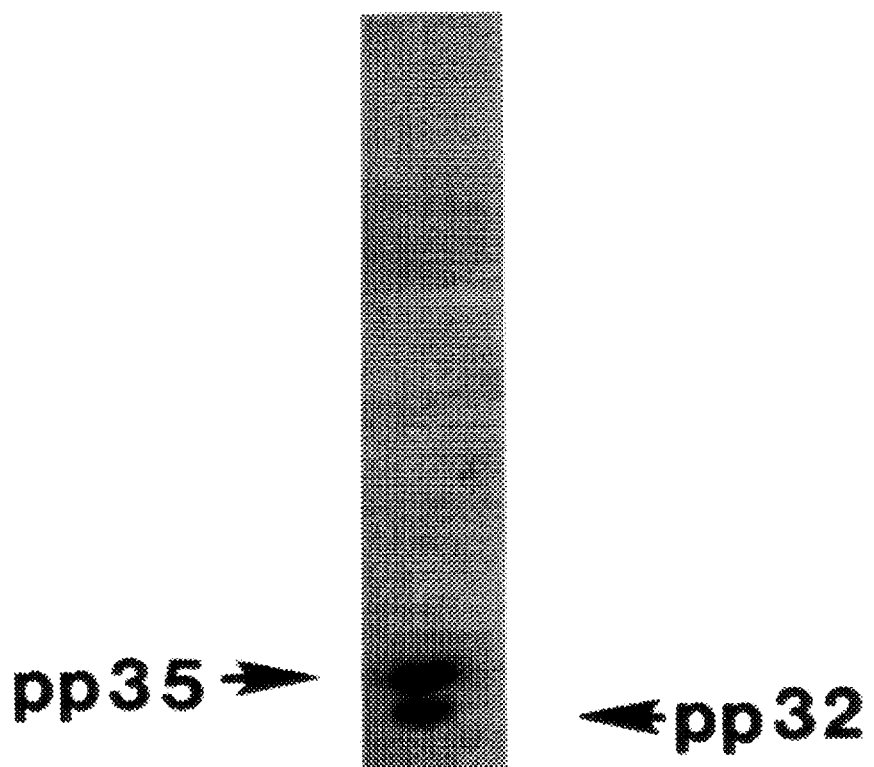
FIG. 2 shows detection of pp35 and pp32 by antibody to denatured pp35 (pp35d). The figure represents a Western blot of $A_{20}$ cell lysate developed using anti-pp35d and $^{125}$I-protein A.

Anti-pp35d was affinity purified as described above and used to examine $A_{20}$ lysates. In immunoblots, affinity-purified anti-35d reacted well with pp35, and interestingly, with an additional 32 kDa protein designated pp32, as seen in FIG. 2. During fractionation, this antibody also detected an additional low-abundance 42 kDa species, designated pp42 (FIG. 4, v.i.).

Gel electrophoresis and Western blotting were performed as described. See Laemmli, 1970, Nature vol. 227, pp. 680–685; Towbin, et al., 1979, Proc. Natl. Acad. Sci., USA, vol. 76, pp. 4350–4354; Gershoni and Palade, 1983, Analyt. Biochem., vol. 131, pp. 1–15; Kuhajda, et al., 1989, Proc. Nat. Acad. Sci., USA, vol. 86, pp. 1188–1192. In some instances blots were visualized with a dye-based detection system. Immunoblots were transferred and processed through primary antibody incubation. Biotinylated goat anti-rabbit IgG (Vector Laboratories) was used as a secondary antibody, followed with intervening washes by an avidin-horse radish peroxidase conjugate (Vector Laboratories) and developed with a Biomeda Universal Substrate kit containing 3-amino, 9-ethyl carbazole (Biomeda Laboratories) used according to the manufacturer's directions.

Cell line $A_{20}$ was obtained from the American Type Culture Collection (ATCC), Rockville, Md. All media were supplemented with 2 mM L-glutamine, 100 µ/ml penicillin, and 100 µg/ml streptomycin, and iron-supplemented newborn calf serum (Hyclone) at the indicated concentrations. All cells were grown in a humidified 5% $CO_2$ atmosphere at 37°. $A_{20}$ cells (Kim, et al., 1979, J. Immunol., vol. 129, pp. 549–554) were grown in RPMI 1640 medium supplemented with 10% serum.

EXAMPLE 3

Peptide Mapping of pp42, pp35 and pp32

Figure 3:
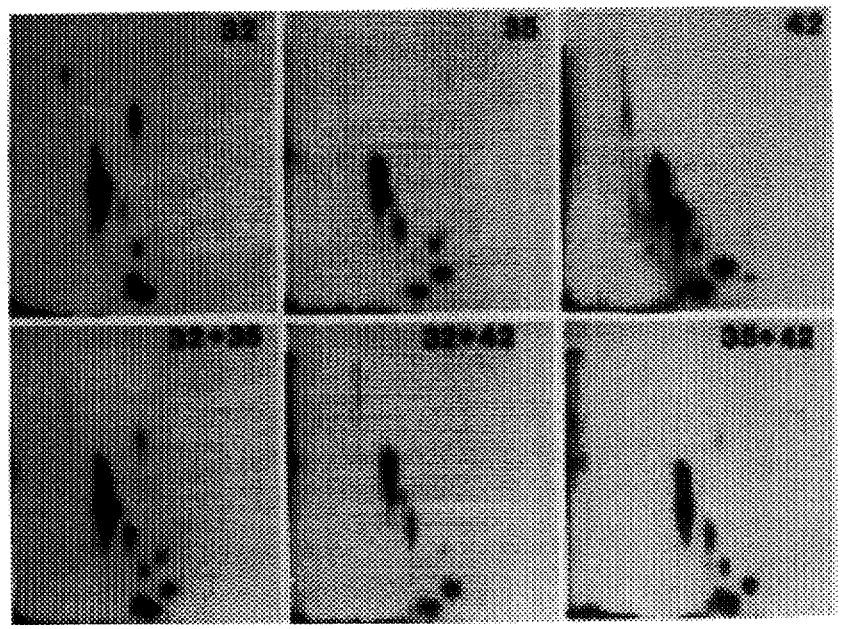
FIG. 3 shows analysis of pp42, pp35, and pp32 by peptide mapping. pp42, pp35, and pp32 were each excised from Coomassie-stained gels, iodinated, digested with α-chymotrypsin, applied to cellulose sheets, and subjected to high-voltage electrophoresis along the horizontal dimension, and to thin-layer chromatography in the vertical dimension. The figure represents the resulting autoradiographs. The top row shows the map of each protein individually, while the bottom row illustrates a mixing experiment in which equal mounts of radioactivity of the indicated protein digests were mixed and mapped together. In the mixing experiment, comigrating peptides appear at full intensity, while peptides contributed by only one of the proteins appear diminished in intensity.

The structural relationship between pp42, pp35 and pp32 was examined using high-resolution two dimensional peptide mapping. Peptide mapping was performed using the Elder technique (Elder, et al., 1977, J. Biol. Chem., vol. 252, pp. 6510–6515; Speicher, et al., 1980, Proc. Natl. Acad. Sci., USA, vol. 77, pp. 5673–5677). FIG. 3 shows the peptide maps of each species alone, and in combination with each of the other species. Note in the top row that the general pattern of the maps is similar, but that each map is unique. The combined maps show that while some peptides overlap, many are unique; in this system, the intensity of non-overlapping peptides is reduced relative to the individual maps, while overlapping peptides remain essentially unaltered. Importantly, one cannot simply derive the map of pp35 or pp32 from the map of pp42; likewise, the map of pp35 does not wholly contain the map of pp32. This suggests that the relationship between the proteins is more complex than one whereby the two smaller polypeptides would be derived from pp42 by proteolytic cleavage.

EXAMPLE 4

Purification of pp35 and pp32

Figure 4A:
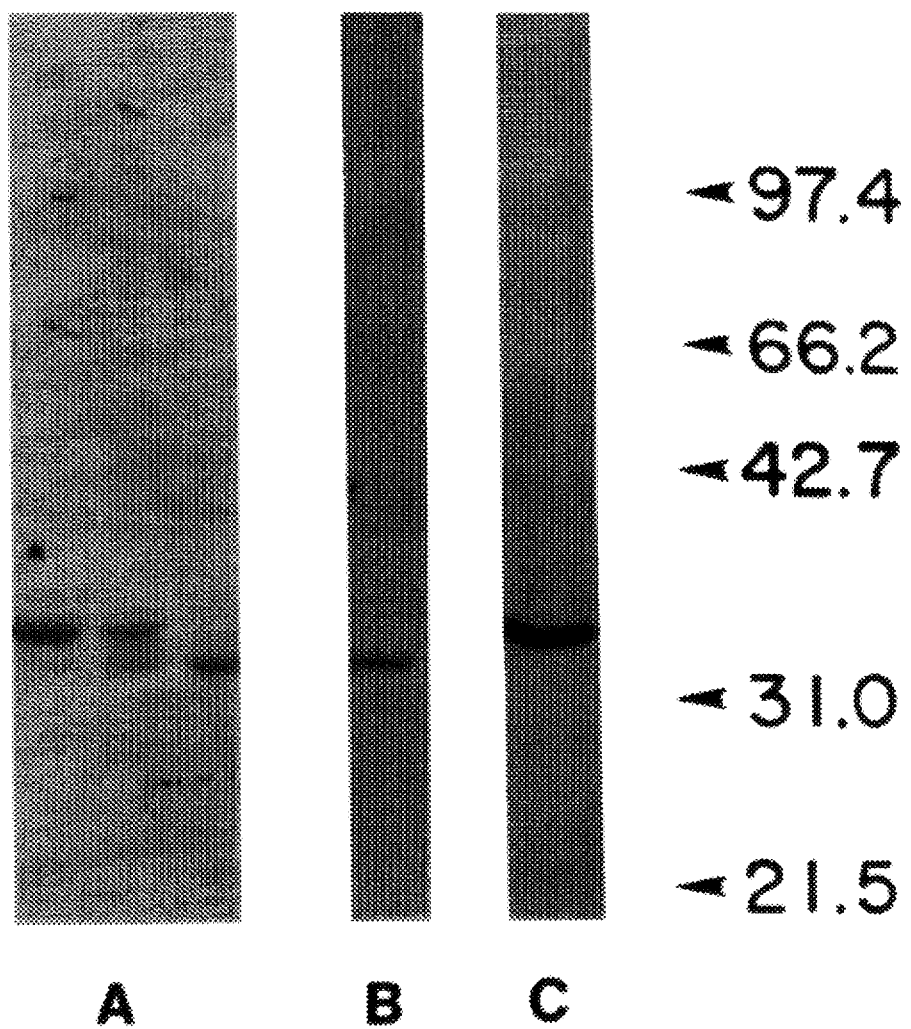
FIG. 4A shows purification of pp35 and pp32. Panel A represents a Coomassie-stained gel of successive alternate fractions from the HPLC-anion exchange column. The figure shows the partial separation of pp35, pp32, and pp42 from one another. Panels B and C represent Coomassie-stained gels showing the homogeneous pp32 and pp35 obtained after HPLC hydroxylapatite chromatography. The numbered arrows indicate the positions of molecular weight standards in kDa.

The initial purification scheme using cross-linked myosin failed to precipitate pp32 and resulted in low yields of pp35. For these reasons, anti-pp35d was used to assay fractions during development of an alternative purification strategy, consisting of sequential detergent lysis in low-ionic strength buffer, DEAE-cellulose chromatography, HPLC anion-exchange chromatography, and HPLC hydroxylapatite chromatography. The Coomassie-stained gel shown in FIG. 4a illustrates typical sequential fractions from the stage of HPLC anion exchange; this step fails to completely resolve pp35 and pp32 (panel A), and includes a faint 42 kilodalton band present in the middle and right-hand lanes. The coomassie-stained lanes shown in panels B and C indicate that subsequent hydroxylapatite chromatography achieves essentially complete purity of greater than about 98%. FIG. 4b, lane B shows that the faint 42 kDa band seen in FIG. 4a is also immunoreactive with anti-pp35d. Generally, 100–200 µg of each protein could be purified from approximately $5 \times 10^9$ cells, representing an estimated yield of around 20%.

In a typical preparation, 6 liters of $A_{20}$ cells were harvested by centrifugation at 600×g, 4°, for 15 min, then washed three times with unsupplemented RPMI 1640. For lysis, the cell pellet was resuspended with a pipette in 20 mM Tris-HCl, pH 7.5, 1 mM EDTA, 1% TRITON X-100 (Pierce Chemical Co.), 10 mM sodium pyrophosphate, 2 mM sodium vanadate, 3 mM ATP, 50 mM NaF, 0.5 mM diisopropyl fluorophosphate (DFP), 0.1 mM phenylmethylsulfonyl fluoride (PMSF) to a density of $2 \times 10^8$ cells/ml. The lysate was then centrifuged at 17,500×g for 20 min. at 4°, and the supernatant passed through a 0.2 µ filter before application to a 2.5 ×10 cm DEAE cellulose column (DE53, Whatman) pre-equilibrated in 150 mM NAG1, 20 mM Tris-HCl, pH 7.5 containing 2 mM sodium vanadate, 0.5 mM DFP, 0.1 mM PMSF. The column was then eluted with a 400 ml linear gradient to 600 mM NaCl in the same buffer with the eluate collected in 70 equal fractions. Fractions were electrophoresed on 10% Laemmli gels (Laemmli, 1970, Nature vol. 227, pp. 680–685) which were further analyzed by Western blotting using anti-pp35d. Positive fractions containing pp42, pp35 and pp32 eluting around 400 mM naCl were pooled and applied directly to an HR-5/5 MonoQ FPLC column (pharmacia Fine Chemicals) pre-equilibrated in 150 mM NaCl, 20 mM Tris-HCL, pH 8.5, room temperature, 1 mM β-mercaptoethanol, 0.1 mM PMSF at a flow rate of 2 ml/min. The column was then developed with a 60 ml gradient of 150 mM naCl in the same buffer to 1.0M NaCl in the same buffer at pH 7.0. Each 600 µl fraction was analyzed on Coomassie-stained Laemmli gels and by Western blotting as previously described. Under these conditions, pp42, pp35 and pp32 eluted at approximately 0.78M NAG1. Following HPLC, fractions containing pp35 or pp32 were individually pooled and applied separately to a 30×4.6 mm MAPS HPHT analytical HPLC hydroxylapatite column (Bio-Rad) after 1:1 dilution in 10 mM sodium phosphate, pH 6.8 10 µM $CaCl_2$, 0.1 mM PMSF. The column was developed with an 18 ml linear gradient to 600 mM sodium phosphate, 10 µM $CaCl_2$, 0.1 mM PMSF at a flow rate of 0.3 ml/min. This purification protocol resulted in homogeneous preparations of pp35 and pp32 on Coomassie-stained Laemmli gels.

Purified pp35 and pp32 were used to raise another set of polyclonal antibodies. Using material purified as described above, 100 µg of either pp35 or pp32 in 2 ml of complete Freunds adjuvant were injected into four subcutaneous sites in each of two Pasteurella-free New Zealand White rabbits on Day 0. On Day 14, the rabbits were boosted with the same amount of antigen in incomplete Freund's adjuvant, with bimonthly bleedings commencing on Day 28. Antibody production was monitored by Western blotting. Initially, in IgG fraction was prepared by loading serum aliquots onto a 5 ml protein A-Sepharose CL4B (Pharmacia) column eluted with 0.1M glycine pH 2.7 and collected into 0.5M sodium phosphate buffer pH 7.5. Fractions were concentrated up to 25 mg/ml IgG by vacuum dialysis against phosphate buffered saline containing 0.1 mM PMSF, 1 mM β-mercaptoethanol. These antibodies, designated anti-pp35n and anti-pp32n, were affinity-purified as described below and characterized for use in quantitative immunoblotting, immunoprecipitation, and immunohistochemical localization studies.

For affinity-purification of anti-pp35n, an affinity column was prepared by concentrating the protein on an 0.4 ml hydroylapatite column (Fast-Flow, Calbiochem) to 600 µg/ml in the eluting 0.4M sodium phosphate buffer, then reacting 600 µg of pp35 with 1 ml of EAH Sepharose CL4B (Pharmacia) and 2 mg each of 1-ethyl-3-(3-dimethylaminopropyl) carbodiimide HCl and N-hydroxysulfosuccinimide (Pierce Chemical Co.) for 6 h at room temperature under constant stirring. Any remaining reactive groups were capped by incubation with 0.5M Tris HCl, pH 7.5, for 2 h. After washing, the derivatized resin was stored in phosphate-buffered saline containing 12 mM sodium azide. A similar column was prepared using 200 µg of pp32 coupled to 1.4 ml of resin. To affinity-purify the antibodies, 0.8 ml of IgG solution were run into a column and incubated for 1 h at room temperature. The column was washed with 15 ml of 2× phosphate-buffered saline containing 0.05% Tween 20, and the antibody eluted with 3 ml of 0.1M glycine pH 2.7. The antibody was collected into 1 ml of 0.5M sodium phosphate, pH 7.5 and concentrated by vacuum dialysis. FIG. 5 illustrates the specificity of these antibodies in Western blots of $A_{20}$ cell lysates; lane A shows that anti-pp35n reacts primarily with pp35, while lane B shows that anti-pp32n reacts primarily with pp32. The cross-reactivities are informative as well. Anti-pp35n shows minor cross-reaction with pp32, pp42, and an unidentified band, while anti-pp32 cross-reacts with pp35. This pattern demonstrates that pp35 and pp32 are unique proteins sharing some epitopes in common with each other, and, in the case of pp35, with pp42. Moreover, these immunochemical data independently support the conclusions drawn from the analysis of peptide maps.

EXAMPLE 5

Induction of pp35 and pp32 in Resting B Cells

Figure 6A:
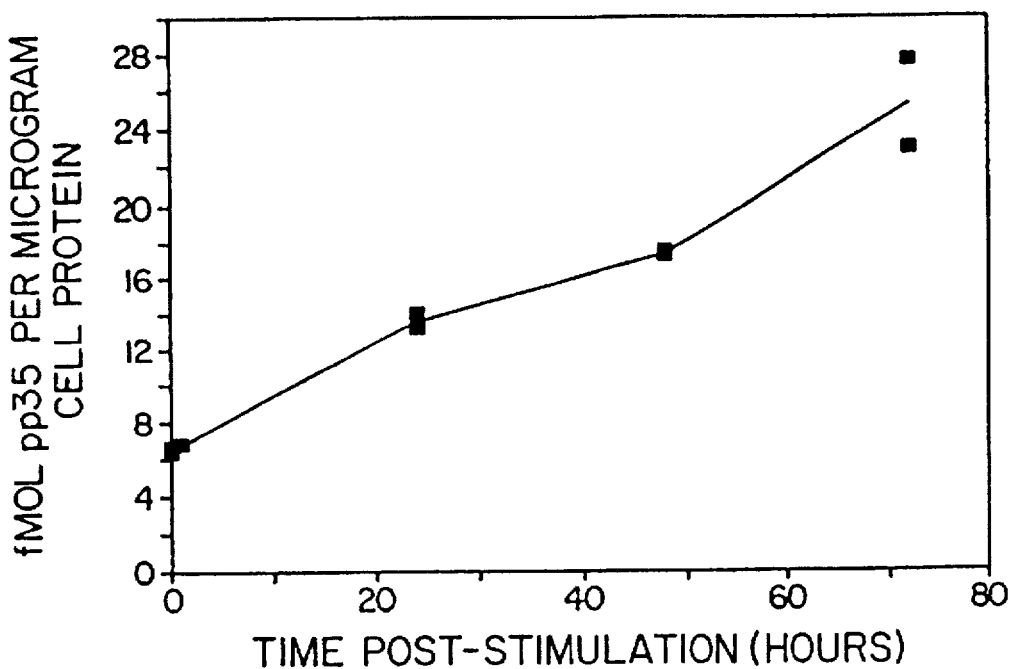
FIGS. 6A–6E show lipopolysaccharide stimulation of resting B cells. Purified small dense B cells were incubated with 40 µg/ml lipopolysaccharide from E. coli 0127:B-8 under conditions which consistently yield a 100-fold stimulation of thymidine incorporation measured by 72 h. Aliquots were removed at times 0, 1 h, 24 h, 48 h, and 72 h. The cell number and protein content of each aliquot was determined, and a portion of each was analyzed by immunoblotting with a cocktail of affinity-purified anti-pp35n and anti-pp32n and developing with $^{125}$I-protein A. For quantitation, the experiment included a standard curve prepared with purified pp35 and pp32. The resultant autoradiographs were quantitated by computerized densitometric image analysis.
Figure 6B:
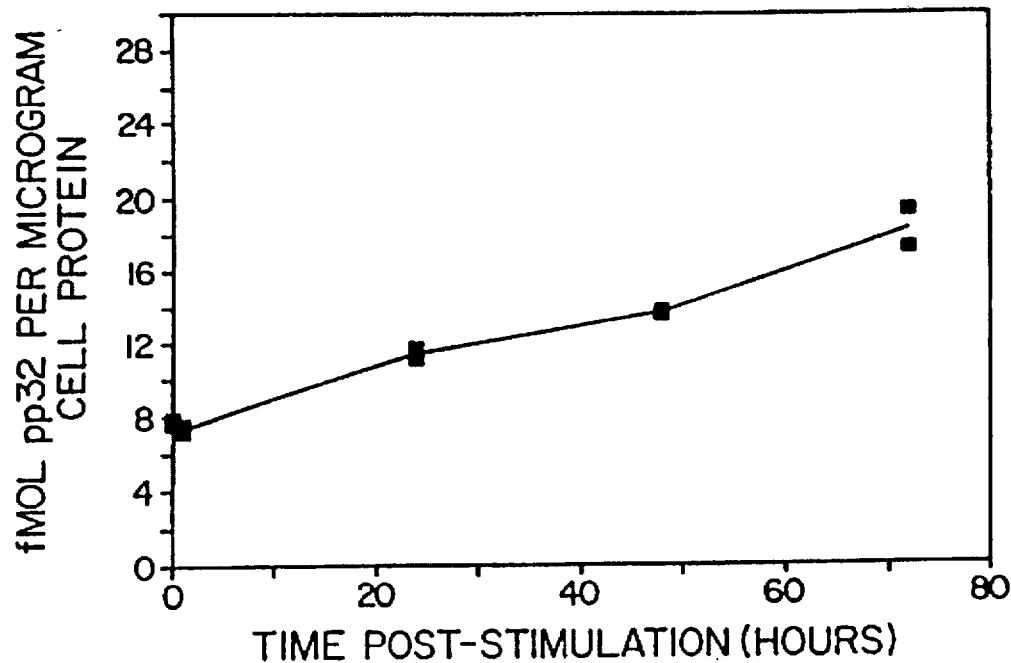
Figure 6C:
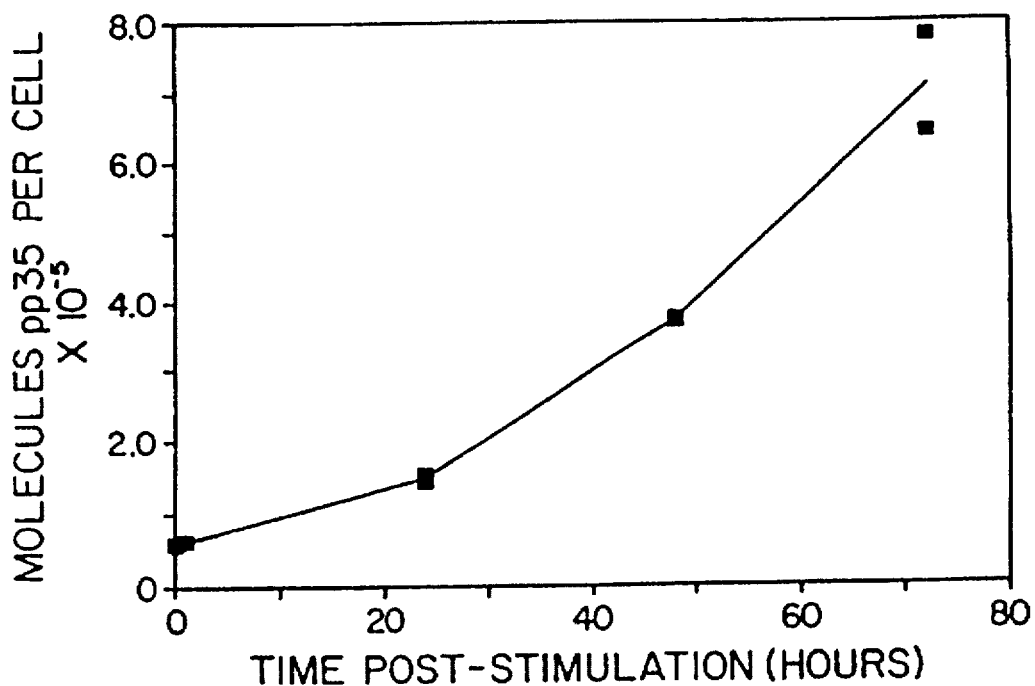
Figure 6D:
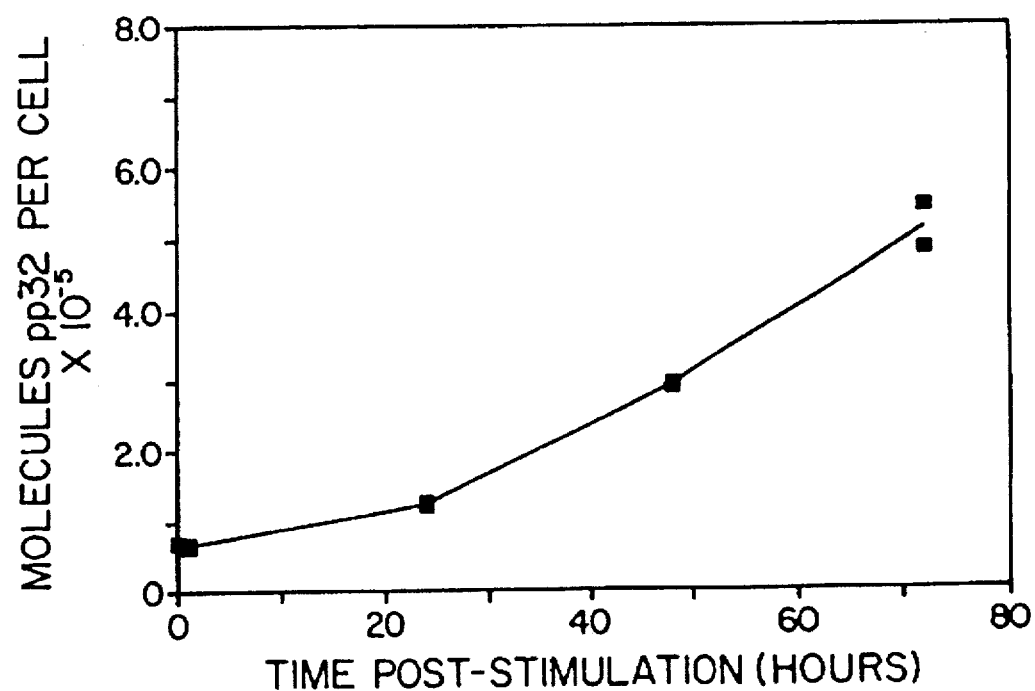
Figure 6E:
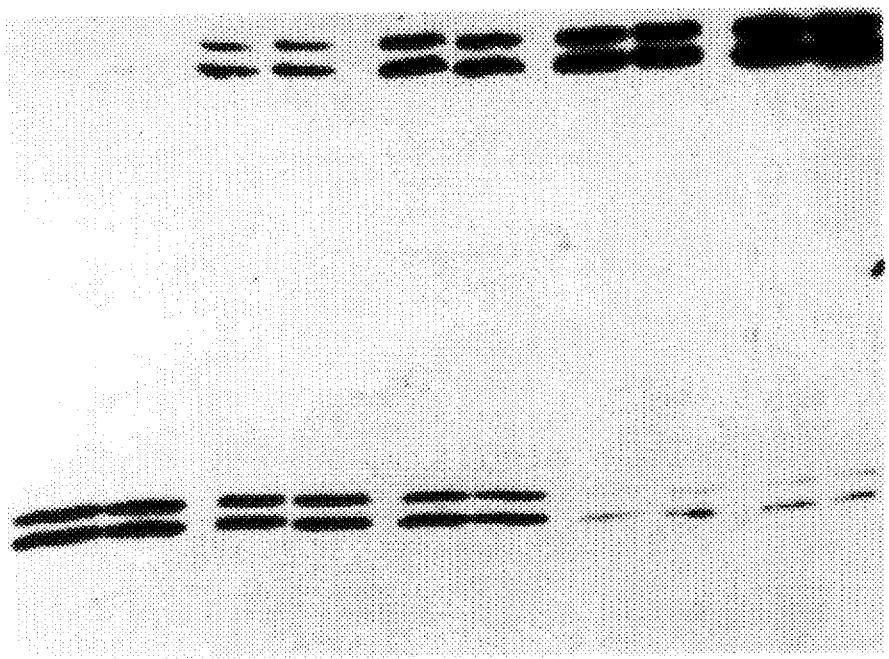

The difference between the staining observed in normal tissues and in $A_{20}$ cells reflects differences in proliferative and functional state of the cell samples. Purified small, dense, resting B cells express relatively low levels of pp35 and pp32 until they are activated and driven into proliferation by a well-characterized polyclonal B cell stimulator, bacterial lipopolysaccharide (See Rabin, et al., 1986, J. Exp. Med., vol. 164, pp. 517–531; Coffman, et al., 1986, J. Immunol., vol. 136, pp. 4538–4541). The data, shown in FIG. 6a, demonstrate that over the course of 72 hours, the expression of pp35 rose 12-fold from $5.9 \times 10^4$ to $7.1 \times 10^5$ copies per cell (panel C), while pp32 increased 7.4-fold from $7.0 \times 10^4$ to $5.2 \times 10^5$ per cell (panel D). Because cell stimulation involves a global increase in cell size, these data were also normalized to total cellular protein so as to reflect specific induction over and above the general increase. Shown in Panels A and B, these data demonstrate a 3.8-fold specific induction of pp35, and a 2.3-fold induction of pp32. Preliminary studies measuring tritiated thymidine incorporation by resting B cell cultures as a function of time and LPS concentration (data not shown) yielded stimulation patterns over 72 h consistent with those reported in the literature. Expression of pp35 and pp32 was quantified by $^{125}$I-protein A immunoblotting in conjunction with computerized image analysis, which yielded an integrated optical density for each band on an autoradiograph; integrated optical density values were convened to protein measurements through a parallel calibration curved of purified pp35 and pp32. FIG. 6b illustrates the immunoblots from which FIG. 6a was derived.

Six to eight week old BALB/C mice were obtained from Charles river. Small dense B cells were isolated from spleen on Percoil gradients essentially as described (Rabin, et al., 1986, J. Exp. Med., vol. 164, pp. 517–531; Coffman, et al., 1986, J. Immunol., vol. 136, pp. 4538–4541). T cells were removed using a cocktail of hybridoma culture supernatants including C3PO (Vidovic, et al., 1984, J. Immunol. vol. 132, pp. 1113–1117), an anti-Ly-1, JIJ (Bruce, et al., 1981, I. Immunol., vol. 127, pp. 2496–2501), an antiThy 1.2, RL172 (Ahmed, et al., 1988, J. Virol., vol. 62, pp. 2102–2106), an anti-CD4, and 3155 (Sarmiento, et al., 1980, J. Immunol., vol. 125, pp. 2665–2672), an anti-CD8, together with 10% Low-Tox-M rabbit complement (Cedarlane Laboratories). The T cell reagents were the gracious gift of Dr. Drew Pardoil. To measure activation by lipopolysaccharide, cells at $1.5 \times 10^5$ cells per well were plated into 96 well tissue culture plates in a total volume of 220 µl per well. Cells were activated by incubation at 37° for 48 h with increasing doses of lipopolysaccharide (LPS W E.coli 0127:B-8, Difco Laboratories). The cells were then pulsed with 1 µCi/well of $^3$H thymidine (ICN) for 16 h, then harvested with a cell-harvester onto Whatman glass-fiber filters presoaked in 10 mM thymidine. This resulted in a dose-dependent stimulation of thymidine incorporation of up to 140-fold over a range of 0.08–50 µg/ml LPS. Cell viability was determined by amido schwarz dye exclusion, and was 95% for stimulated B cells at 72 h, and 50% for unstimulated cells.

To determine pp35 and pp32 content by quantitative Western blotting, resting B cells were incubated at the above concentration in T-150 culture flash for 0 h, 1 h, 24 h, 48 h and 72 h in the presence of 40 µg/ml LPS. At each time point, cells were counted harvested, lysed by resuspension in 150 µl of 20 mM Tris-HCl, pH 7.5, 1 mM EDTA, 1% Triton X-100, 0.1 mM PMSF, 0.5 mM DFP. The supernatants were then collected by centrifugation at 16,000×g for 10 min. at 4° and stored at −80°; separate aliquots wee reserved for determination of total protein by BCA protein assay (Fierce Chemical Co.). Similar duplicate amounts of total cellular protein for each time point were separated on 10% Laemmli gels along with a standard curve prepared from a mixture of purified pp35 and pp32 calibrated by BCA protein assay. The standard curve consisted of 31 ng, 62.5 ng, 125, ng, 250 ng, and 500 ng each of pp35 and pp32. The gels were transferred to nitrocellulose and the blots probed in the same solution of a mixture of affinity purified anti-pp35n and anti-pp32n at 5 µg/ml in Tris-saline containing 3% bovine serum albumin for 2 h followed, after intervening washes, by $^{125}$I protein A at $3 \times 10^6$ cpm/ml in albumin-Tris saline for 2 h. The blots were washed together extensively in Tris-saline, and exposed on the same piece of Kodak XAR-5 film in a cassette containing a Cronex Lightning Plus intensifying screen (DuPont). The bands seen on the autoradiogram were quantitated by computed densitometry using a Loats image analysis system. The integrated optical density values obtained for the standard values of pp35 and pp32 were plotted against he amount of protein.

EXAMPLE 6 pp35 and pp32 Expression in Lymphoid Cell Lines

Figure 7B:
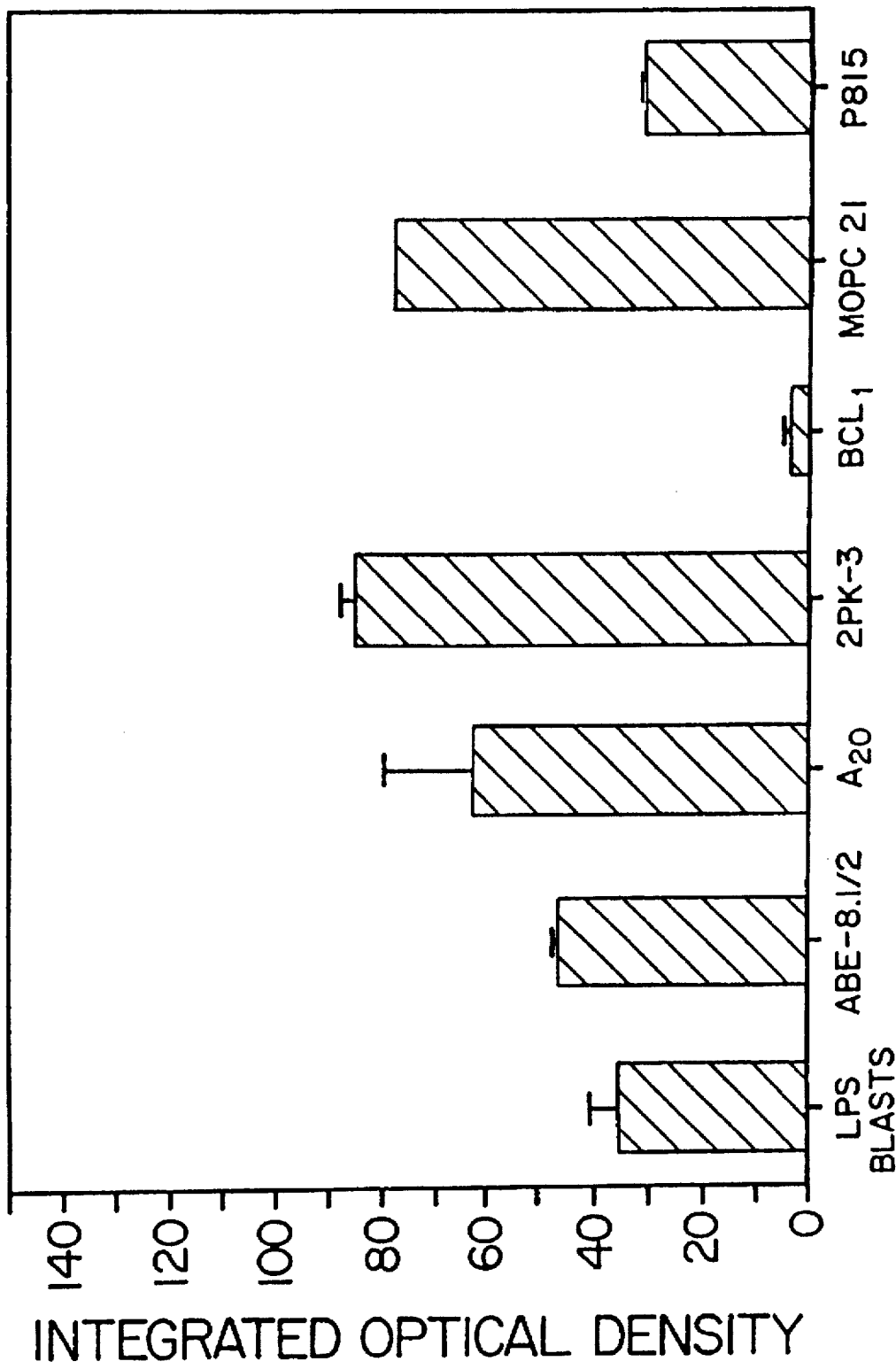

In populations of neoplastic cell lines, pp35 and pp32 are expressed at high levels (FIG. 7). In the majority of cell lines, these levels exceed those seen in normal B cells stimulated with LPS for 72 h. To a first approximation, there is a reciprocal relationship between expression of pp35 and pp32 in that less differentiated lines tend to express higher levels of pp35 than pp32, while for more differentiated lines the reverse is true. There are at least two possible explanations for the discordant case of the cell line $BCL_1$: pp32 expression may be low; or pp32 itself may be immunologically altered. While these data are open to a number of interpretations, one explanation is that pp35 and pp32 assume different functions in the cell nucleus which are linked to different states of proliferation or differentiation.

2PK-3, a BALB/C B cell lymphoma (Lanier, et al., 1981, J. Immunol., vol. 127, pp. 1691–1697), and ABE-8.½, a BALB/C pre-B cell lymphoma (Burchiel and Warner, 1980, J. Immunol., vol. 124, pp. 1016–1021), were grown in Dulbecco's modified Eagle's medium (DMEM) supplemented with 4.5 g/l glucose, 50 µM 2-mercaptoethanol, and 10% serum. P815, a DBA/2 mastocytoma (Ralph, et al., 1976, J. Exp. Med., vol. 143, pp. 1528–1533), and P3.6.2.8.1, a subline of the BALB/C plasmacytoma MOPC 21 (Knopf, et al., 1973, Eur. J. Immunol., vol. 3, pp. 251–259), were grown in DMEM with 10% serum. BCL$_1$ Clone CW13.30-383, a BALB/C B cell leukemia (Brooks, et al., 1984, J. Immunol., vol. 133, pp. 3133–3137), was grown in RPMI 1640 with 10% serum.

EXAMPLE 7 pp35 and pp32 are Phosphoproteins.

Figure 8:
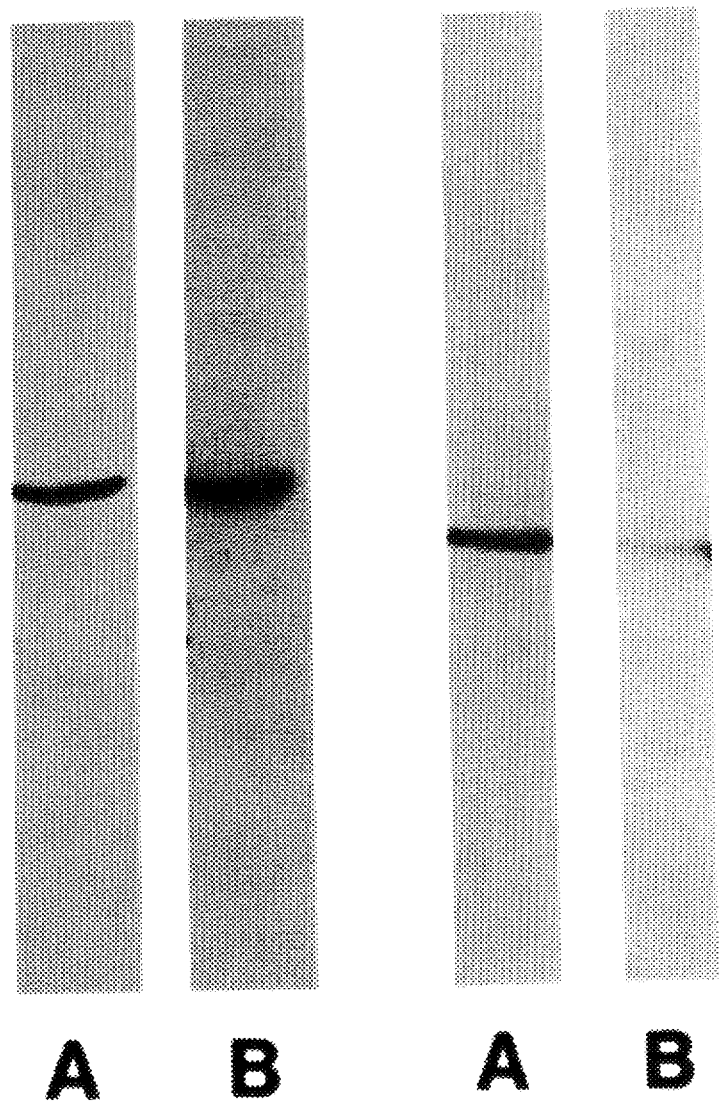
FIG. 8 shows that pp35 and pp32 are phosphoproteins. $A_{20}$ cells were labeled for 4 h by incubation with $^{32}P$ orthophosphate in otherwise phosphate-free medium. pp35 and pp32 were isolated as described, electrophoresed on a 10% Laemmli gel, transferred to nitrocellulose, and analyzed by reactivity with antibodies to pp35 and pp32 (Lanes A) and by autoradiography (Lanes B). Antibody reactivity was detected colorimetrically.

The initial evidence that pp35 and pp32 are phosphoproteins came from simultaneous autoradiography and immunoblotting of these proteins after purification from cells labeled with $^{32}$P as orthophosphate. In one experiment, A$_{20}$ cells were labeled for 4 h in otherwise phosphate-free medium prior to purification. For each of the pp35 and pp32 panels of FIG. 8, lane A illustrates a colorimetric immunoblot developed with either anti-pp35n or anti-pp32n, and lane B represents an autoradiograph of the blot. Both pp35 and pp32 are phosphoproteins in vivo. In this experiment, complete coincidence of the immunoreactivity of each protein with the radioactive band was observed. Moreover, $^{32}$P-labeled pp35 and pp32 are radiochemically pure, so that measurements of radiochemical activity truly reflect incorporation into each protein.

EXAMPLE 8

Casein Kinase II Phosphorylates pp35 and pp32.

The potential role of various kinases in pp35 and pp32 phosphorylation was studied in vitro by their ability to phosphorylate native and dephosphorylated pp35 or pp32. Labeled pp35 contains phosphoserine and phosphothreonine, while labeled pp32 contains only phosphoserine; alkaline phosphatase quantitatively dephosphorylates $^{32}$P-phosphoserine in both pp35 and pp32.

A$_{20}$ cells were labeled in vivo. Approximately 5×10$^9$ A$_{20}$ cells were washed once and resuspended at 2×10$^7$ cells/ml in phosphate-free minimal essential medium (Gibco) supplemented with 10% iron-supplemented calf serum previously dialyzed against medium, 2 mM L-glutamine, 100 U/ml penicillin, 100 µg/ml streptomycin, and 1x nonessential amino acids solution. The cells were incubated in humidified 5% CO$_2$ atmosphere at 37° with 15 mCi of carrier-free $^{32}$P as orthophosphate (Amersham) for 3 h. Following incubation, pp35 and pp32 were purified as described above.

Studies of several kinare in vitro showed that both pp35 and pp32 are substrates for casein kinase II. The results strongly suggest a physiologic role for casein kinase II in pp35 phosphorylation, and for a related kinase in pp32 phosphorylation. Casein kinase II consistently yielded the highest degree of $^{32}$P incorporation onto dephosphorylated pp35 and pp32, rephosphorylating pp35 to a level of 0.76 mol/mol (Table I).

Table I

| Casein Kinase II | pp35, dephosphorylated | 0.76 mol/mol ± 0.03 |
| | pp35, native | 0.05 mol/mol ± 0.01 |
| | pp32, dephosphorylated | 0.08 mol/mol ± 0.01 |

Table I-continued

| Protein Kinase A | pp32, native | <0.01 mol/mol |
| | pp35, dephosphorylated | <0.02 mol/mol |
| | pp35, native | <0.02 mol/mol |
| | pp32, dephosphorylated | <0.02 mol/mol |
| | pp32, native | <0.02 mol/mol |
| Protein Kinase A | pp35, dephosphorylated | <0.01 mol/mol |
| | pp35, native | <0.01 mol/mol |
| | pp32, dephosphorylated | <0.01 mol/mol |
| | pp32, native | <0.01 mol/mol |
| EGF Receptor Kinase | pp35, dephosphylated | no incorporation |
| | pp32, dephosphorylated | <0.01 mol/mol |

In contrast, the catalytic subunit of protein kinase A, protein kinase C, and EGF receptor kinase all failed to promote significant levels of incorporation, and showed little sensitivity to whether the substrate proteins were dephosphorylated or not. As would be predicted for casein kinase II activity, phosphorylation of both pp35 and pp32 by casein kinase II utilized GTP as a substrate and was completely inhibited by heparin.

Rephosphorylation of the dephosphorylated phosphate turnover sites was investigated with protein kinase C from rat-brain, the catalytic subunit of cAMP-dependent protein kinase (Sigma), casein kinase II from bovine thymus, and A 431 cell epidermal growth factor receptor kinase, generously provided as a solution of 30 µg/ml of EGF receptor in buffer containing 50 µM EGF by Dr. Wolfgang Weber (Instit fur physiologische Chemie, Universitat Hamburg).

Casein kinase II was purified as described (Zandomeni et al., 1988, FEBS Letters, vol. 235, pp. 247–251). Aliquots of fractions were screened for casein kinase II activity in 30 µl final volumes of 20 mM Tds HCl at pH 7.5 160 mM NaCl, 8 mM MgCl$_2$, 0.1 mM DTr, 0.1 mM GTP with gamma-labeled $^{32}$P GTP (Amersham) at a final specific activity of 1 µCi per nanomole, 1.0 mg/ml partially hydrolyzed and dephosphorylated casein (Sigma), in the presence and absence of the casein kinase II inhibitor 5,6-dichloro-1-beta-D-ribofuranosyl-benzimidazole (DRB, Sigma) at a concentration of 100 µM, added from a stock solution in 50% dimethyl sulfoxide. After incubation at 30° for 10 min, reactions were terminated by the addition of 500 µl of ice-cold 25% TCA. Fractions showing kinase activity 50% inhibitable by DRB were selected for pooling. The final enzyme preparation showed the expected subunit structure on Coomassie-stained Laemmli gels, utilized GTP, showed partial inhibition by DRB, and showed complete inhibition by 1 µg/ml heparin.

Dephosphorylation of pp35 and pp32 was carried out by incubation with 1 unit of alkaline phosphatase from bovine intestinal mucosa (Sigma, Type VII) per/µg of protein in 20 mM Tris HCl at pH 8.0, 1 mM MgCl$_2$, 0.1 mM ZnCl$_2$ for 1 h at room temperature. The reaction mixture was loaded onto a 0.2 ml hydroxylapatite column (high resolution, Calbiochem), previously equilibrated in 20 mM sodium phosphate pH 7.5. The column was eluted sequentially with 0.4 ml each of 100 mM, 200 mM and 450 mM sodium phosphate, pH 7.5. Alkaline phosphatase eluted at 100 mM sodium phosphate, while pp35 or pp32 eluted at 450 mM. Proteins labeled in vivo with 32P as orthophosphate were used to estimate the extent of dephosphorylation. While the $^{32}$P label was quantitatively removed from pp32, pp35 retained approximately one-third of the original label in the form of phosphothreonine.

Protein kinase C was purified using elements of two protocols (Walton et al., 1987, Analyt. Biochem., vol. 161, pp. 425–437; Woodgett and Hunter, 1987, J. Biol. Chem., vol. 262, pp. 4836–4843). Briefly, eleven rat brains were harvested, immediately frozen in liquid nitrogen, and homogenized with a Brinkmann Polytron in 150 ml of 10 mM Tris HCl at pH 7.5, 10 mM EGTA, 5mM EDTA, 0.1% (v/v) β-mercaptoethanol, 4 µg/ml leupeptin, 0.5 mM diisopropylfluorophosphate, 0.1 mM phenylmethyl sulfonyl fluoride, and 6 µg/ml soybean trypsin inhibitor. The homogenate was centrifuged for 30 min at 10,000×g. The supernatant was filtered through three layers of cheesecloth into DE53 (Whatman) pre-equilibrated in 20 mM Tris HCl at pH 7.5, 1 mM EDTA, 0.1% (v/v) β-mercaptoethanol and batch adsorbed for 30 min while stirring at 4°. The resin was poured into a 2×20 cm column which was then eluted with a 1 l gradient of 20 mM NaCl to 300 mM NaCl in the same buffer. The column fractions were screened for phorbol ester stimulated activity by incubating 5 µl of 1 mg/ml histone H-1 (Boehringer-Mannheim) in a final volume of 20 µl containing 20 mM HEPES, pH 7.5, 10 mM $MgCl_2$, 0.5 mM $CaCl_2$, 50 µg/ml freshly sonicated phosphatidylserine, 0.1 mM ATP with gamma-labeled $^{32}$P-ATP (Amersham) at a final specific activity of 1 µCi per nanomole, and, in some samples, phorbol myristic acetate at 5 µg/ml. After initiation by the addition of substrate stock, the reactions were stopped after 5 min at 30° by the addition of 500 µl of 20% ice cold 20% trichloroacetic acid (TCA). Precipitates were incubated at 4° for 20 min, then centrifuged for 5 min at 16,000×g. The pellets were washed twice with 20% TCA and then counted by Cerenkov counting. Positive fractions were selected on the basis of PMA-stimulated phosphorylation of histone H-1, pooled, and then brought to 1.5M NaCl by the addition of solid NaCl. This pool was then loaded onto a 10 ml phenyl Sepharose column (Pharmacia) preequilibrated in 20 mM Tris HCl at pH 7.5, 2 mM EDTA, 2 mM EGTA, 1 mM dithiothreitol, 1.5M NaCl. The column was eluted with a 200ml linear gradient of 1.5M NaCl to OM NaCl in the same buffer. Positive fractions were pooled and applied to a 10 ml protamine-agarose column (Pharmacia) equilibrated in 20 mM Tris HCl at pH 7.5, 2 mM EGTA, 2 mM EDTA 1 mM DTT 0.1 mM PMSF, 0.5 mM DEP 0.1M NaCL pH 7.5. The column was eluted with a 160 ml linear gradient of increasing salt from 0.5M to 1.5M NaCl. Purified protein kinase C activity comigrated with an 80 kDa band on Coomassie-stained Laemmli gels; PMA increased histone H-1 phosphorylation by 15 to 18 fold over baseline samples without PMA in typical preparations. The final yield was approximately 40 µg. The enzyme was stored stably for several months at −80° in buffer containing 16% glycerol and 0.02% Triton X-100.

Protein kinase C assays were carried out for 30 min at 37° with 0.5 µg of the 80 kDa protein kinase C isoenzyme in 20 mM HEPES at pH 7.5, 10 mM $MgCl_2$, 0.5 mM $CaCl_2$, 50 µg/ml freshly sonicated phosphatidylserine, and 0.1 mM containing gamma-labeled $^{32}$P ATP (Amersham) at a final specific activity of 5 µCi per nanomole, in the presence and absence of 5 µg/ml PMA. Generally, 1 to 5 82 g of pp35 or pp32 were tested. Reaction products were analyzed on Laemmli gels and on two dimensional gels (O'Farrell, 1979, J. Biol. Chem., vol. 250, pp. 4007–4021) gels using histone H1 (Boehringer) as a positive control substrate.

Protein kinase A assays utilized the catalytic subunit of cAMP-dependent protein kinase from bovine heart (Sigma). Reactions were carried out by incubating 50 units of enzyme with 5 µg of either pp35 or pp32 for varying times at 30° in 120 µl volumes of 50 mM HEPES at pH 7.4, 25 mM NaCl, 10 mM $MgCl_2$, 1 mM EDTA, 0.1 mM β-mercaptoethanol, and 0.1 mM ATP containing gamma-labeled $^{32}$P ATP at a final specific activity of 1 µCi per nanomole. 1 µg histone H1 served as a positive control substrate. Reaction products were analyzed as above.

Casein-Kinase II assays were carried out by incubating 1 µg enzyme with 1 to 5 µg pp35 or pp32 for varying times at 30° in 20 mM Tris HCl at pH 7.9, 8 mM $MgCl_2$, 0.1 mM DTT and 0.1 mM GTP containing gamma-labeled $^{32}$P GTP at a final specific activity of 1 µCi per nanomole. Partially dephosphorylated and hydrolyzed casein from bovine milk (Sigma) served as positive control substrate. 1 µg/ml of heparin in the reaction mixture completely inhibited phosphate incorporation into casein, pp35, and pp32. Reaction products were analyzed as above.

The epidermal growth factor receptor assays were carried out by incubating 0.15 kinase with 1 to 5 µg pp35 or pp32 for varying times at 30° in 100 µl of 20 mM HEPES at pH 7.5, 1 mM $MnCl_2$, 5 mM $MgCl_2$, 50 mM EGF, and 0.1 mM ATP containing gamma-labeled ATP at a final specific activity of 1 µCi per nanomole. The autophosphorylation of the receptor served as a positive control for the kinase activity. Reaction products were analyzed as above.

The amount of phosphate transferred from ATP or GTP to pp35 or pp32 was calculated from Cerenkov counts of the corresponding excised bands from Coomassie-stained gels. Raw Cerenkov counts were convened to moles of phosphate using an experimental specific activity value of Cerenkov counts per minute per nMol phosphate obtained from triplicate counts of 5 µl aliquots of reaction mixtures as known nucleotide concentration; care was taken to closely approximate the sample geometry used to measure the activity of the gel slices. These measurements were combined with previous triplicate measurements of protein substrate concentration by the BCA assay (Pierce Chemical Co.) to calculate the stoichiometry of phosphorylation at the susceptible sites. The background counts subtracted from each measurement were obtained by counting gel slices of comparable area from each lane from areas with no protein. Kinase reactions were carried out in triplicate for varying time points up to 2 h to assure completion. Casein kinase II reactions were complete by 15 min., while protein kinase A, protein kinase C, and the EGF receptor kinase all showed small, gradual increases over the two hour period with no obvious plateau. Two hours were therefore arbitrarily chosen as a cutoff for the determination of phosphorylation stoichiometry for these latter kinases.

EXAMPLE 9

HeLa Cells Contain pp35 and pp32.

HeLa cells, a human cervical epithelioid carcinoma cell line, (available from the ATCC) appear to contain pp35 and pp32. An immunoblot of a total HeLa cell hypotonic detergent lysate was prepared essentially as described for $A_{20}$ cells above. Antibodies to denatured, gel-purified pp35 which recognize both pp35 and pp32 react with a diffuse band at approximately 33 kDa; in lighter exposures the heavy band resolves into two closely-spaced components. The experiment clearly indicates the presence of cross-reactive species of the expected molecular weights in a human cell line, but does not clearly establish the number of species or degree of relationship with murine lymphoid pp35 or pp32.

EXAMPLE 10 pp35 and pp32 Immunostaining Correlates with Increased Malignant Potential

Human tissues react with antibodies to native murine pp35 and pp32, showing increased staining frequency, increased staining intensity, and altered subcellular distribution with increasing malignancy.

Paraffin-embedded sections of human lymphoid tissue were stained with affinity-purified antibodies to native pp35 and pp32. Staining was evaluated semi-quantitatively by two independent observers. In a diffuse large cell lymphoma, the neoplastic cells show prominent nuclear staining while the normal lymphocytes are negative. Adenomatous colonic epithelium shows prominent nuclear anti-pp35 staining in virtually every cell, in contrast to the limited staining of crypts seen in normal colon. In contrast, invasive adenocarcinoma of the colon shows predominantly cytoplasmic pp35 staining, while pp32 staining remains nuclear. This change from nuclear to cytoplasmic distribution is highly reminiscent of the association of c-abl transforming activity with a relocation from nucleus to cytoplasm (Van Etten, et al., Cell, vol. 58, pp. 669–678, 1989).

Table 2 illustrates the results of a screen of human lymphomas with anti-pp35 and anti-pp32, which demonstrates that increased staining frequency and intensity and altered distribution are associated with increased malignancy. Lymphomas were examined for pp35 and pp32 staining independent of diagnosis, then ranked in increasing order of frequency of staining. The result was a ranking which predicted the level of virulence suggested by the diagnosis.

TABLE 2 pp35 and pp32 Staining in Normal and Neoplastic Lymphoid Tissue

| LESIONS | pp35 | | | pp32 | | |
|---|---|---|---|---|---|---|
| | % Positive | Intensity | Location | % Positive | Intensity | Location |
| LOW GRADE LESIONS | | | | | | |
| Small Lymphocytic Malignant Lymphoma (Well-Differentiated Lymphocytic) | 40–50% | +1 | Nucleus | NOT DONE | | |
| | Staining in tumor only. Weak, infrequent staining of normal small lymphocytes | | | | | |
| Follicular Lymphoma Small Cleaved Predominant (Poorly Differentiated Lymphocytic Lymphoma) | 40–50% | +/− | Nucleus | 40–50% | +1 | Nucleus |
| INTERMEDIATE GRADE LESION | | | | | | |
| Follicular Lymphoma Large Cell Predominant (Nodular Histiocytic Lymphoma) | 60–70% | 2+ 1+ | Cytoplasm Nucleus | 60–70% | +3 | Nucleus |
| | Staining described is for large cell component. Small cells showed +/− nuclear staining in 40–50% of cells. | | | Small cells showed 40–50% +1 nuclear staining. | | |
| HIGH GRADE LESIONS | | | | | | |
| Diffuse-Large Cell Malignant Lymphoma (Diffuse Histiocytic Lymphoma) | >90% Focal | 3+ 2+ | Nucleus Cytoplasm | >90% | +3 | Nucleus |
| | Small, normal lymphocytes negative | | | Small, normal lymphocytes negative | | |
| Small Noncleaved Cell Malignant Lymphoma (Diffuse Undifferentiated Lymphoma) | >90% | 3+ | Nucleus | >90 | 3+ | Nucleus |
| | Small, normal lymphocytes negative | | | Small, normal lymphocytes negative | | |
| NORMAL TISSUES | | | | | | |
| Tonsil & Reactive Lymph Node (Identical Findings) | 50–60% | 1+ | Nucleus Germinal Centers | 50–60% | 1+ | Nucleus Germinal Centers |
| | 30–60% | 1+ | Nucleus Paracortex | 30–40% | 1+ | Nucleus Paracortex |
| | Occasional small faci of 3+ with 70% positive nuclear staining in paracortex. | | | Occasional small foci of 3+ with 70% positive nuclear staining in paracortex. | | |

EXAMPLE 11 pp32 cDNA is Cloned and Partially Sequenced.

Screening an oligo dT-primed $A_{20}$ λ gt11 cDNA library with a 42 base oligonucleotide guessmer (Sambrook, et al., Molecular Cloning: A Laboratory Manual, Cold Spring Harbor Laboratory Press, 1989, pp. 11.11–11.16) derived from pp35 peptide sequence recovered a pp35-related cDNA predicting additional independent pp35 peptide sequence. The major pp35 phosphopeptide sequence L-L-P-Q-L-S-Y-L-D-G-Y-D-D-E (SEQ ID NO:6) containing a casein kinase II phosphorylation site was backtranslated to the best guess 42 base oligonucleotide sequence using previously described codon preference rules (Lathe, J. Mol. Biol., vol. 183, pp. 1–12, 1985). The resultant oligonucleotide, 5'-CTGCTGCCCCAGCTGTCCTACCTGGATGGCTAT-GATGATGAG, hybridizes with a 1.3 (SEQ ID No:8) kb RNA species in Northern blots of $A_{20}$ cell RNA.

Approximately 600,000 λ gt11 plaques were screened with end-labeled oligonucleotide and the filters washed at moderate stringency, yielding 23 cDNA clones which remained positive through tertiary plaque purification. The first cDNA to be subcloned into Bluescript™ and partially sequenced by double-stranded dideoxynucleotide sequencing is approximately 1 kb and contains predicted protein sequences identical to an independently sequenced pp35 peptide. A portion of the sequence of the cDNA is shown in FIG. 9.

The cDNA (SEQ ID No:4) and predicted peptide sequences (SEQ ID No: 5) were compared to all nucleotide and protein sequences in the Genbank and EMBL libraries using the FASTA program of the University of Wisconsin in GCG sequence analysis package, and using the TFASTA program to compare predicted amino acid sequences to translations of the nucleotide sequences. No close matches were found, confirming that pp32 is distinct from previously described nuclear proteins. pp32 cDNA does contain interesting homologics of 30 to 50% over 60 to 100 nucleotide stretches with such molecules as human calcyclin, human c-myc germ line protooncogene, human ealmodulin, and human U2 snRNP, however the true extent and significance of these homologics is at present unknown. No homology has been found in the determined sequence to erythrocyte protein 4.1, even though some preparations of anti-4.1 antibodies cross-react with denatured pp35. Curiously, there is no such cross-reactivity with native pp35. This case is reminiscent of synapsin I, which also cross-reacts with anti-protein 4.1 antibodies but is unrelated at the sequence level (Baines and Bennett, (1985), Nature, vol. 315, pp. 410–413; McCaffery and DeGennaro (1986), EMBO J., vol. 5, pp. 3167–3173; and Conboy, et al., (1986), Proc. Natl. Acad. Sci. USA, vol. 83, pp. 9512–9516.)

EXAMPLE 12

Cloning of Murine and Human pp32

The cloning strategy employed a 42 base pair nondegenerate oligonucleotide probe back-translated from an independently sequenced murine pp35 peptide to screen a murine cDNA library from $A_{20}$ cells. The initial murine clones were used to obtain human cDNA and to complete the murine sequence.

Materials.

A poly-T primed cDNA library was constructed by Clonetech from $A_{20}$ cell mRNA purified by the guanidinium isothiocyanate method (8) in lambda gt11. A randomly primed cDNA library from HL-60 cells in Lambda-Zap and a poly-T primed $A_{20}$ cell cDNA library in Uni-Zap were purchased from Stratagene. All cDNA's were subcloned into Stratagene pBluescript II KS+except for clones in vivo excised from the HL-60 Lambda-Zap library which were in pBluescript I SK-. A GAPDH probe was purchased from Clonetech. Oligonucleotides were synthesized by Genosys. Enzymes and kits for molecular biology were from Amersham, Collaborative Research, Boehinger Mannheim, Clonetech, Gibco BRL, Stratagene, Promega, Schleicher and Schuell, and United States Biochemicals. Other chemicals purchased from Sigma, and J. T. Baker. Radiochemicals were from Amersham and ICN.

Cell Culture.

Cell culture media and reagents were from Gibco BRL, and serum supplements were from Hyclone. $A_{20}$ cells (2, American Type Culture Collection) were maintained in RPMI 1640 supplemented 10% fetal bovine serum, 50 units/ml penicillin and 50 µg/ml streptomycin and passed twice weekly by diluting 1:10 in fresh medium.

HL-60 cells (11) were maintained in RPM 11640 supplemented 10% fetal bovine serum, 50 units/ml penicillin and 50 82 g/ml streptomycin and passed twice weekly by diluting 1:10 in fresh medium. Primary rat embryo fibroblasts were either purchased through BioWhittaker or were generously donated by Dr. Chi Dang. Cells were grown in low glucose DMEM containing 10% FBS, 50 units/ml penicillin and 50 µg/ml streptomycin. All cells were grown in humidified incubators at 37°, 5% CO2.

Purification of Total and Messenger RNA.

For the $A_{20}$ library, total RNA was isolated from cultured $A_{20}$ cells using the guanidinium/cesium chloride method (8). Poly-A+mRNA was purified using an oligo (dT)-cellulose column (8). Total RNA and mRNA from HL-60 cells were isolated using a modified protocol of the single-step acid-phenol extraction (12) and the MiniRiboSep kit from Collaborative Biomedical, respectively.

Library Screening.

Initial clones were obtained by screening the $A_{20}$ library with a long, nondegenerate oligonucleotide probe designed by back-translating, using Lathe's codon usage frequencies (13), the phosphopeptide from murine pp35 sequenced in Example 11. The oligonucleotide was synthesized by Genosys and purified by HPLC. 600,000 pfu of the previously described $A_{20}$ lambda gt11 library was initially plated on E.coli strain Y1090, transferred onto Nytran filters (Schleicher and Schuell) and fixed by baking for 2 hours in an 80° vacuum oven. The screening oligonucleotide guessmer was end-labelled using T4 polynucleotide kinase (New England Biolabs) and used to probe the library at moderate stringency. Filters were hybridized overnight in 6X SSC, 1X Denhardt's, 0.05% sodium pyrophosphate, and 100 µg/ml salmon sperm DNA at 42°, then washed 2 times at room temperature in 6X SSC and 2 times at 50° in 6X SSC.

13 clones positive on duplicate filters were plaque purified and the DNA isolated from liquid lysates on cesium chloride gradients (8). cDNA Inserts were cut out using EcoRI and ligated into pBluescript II KS + (Stratagene). Cesium-banded plasmid was sequenced using T7 and T3 primers (Stratagene) and Sequenase II (United States Biochemicals) and nested-deletion constructs were made using the Exo/Mung deletion kit (Stratagene).

The initial partial murine pp32 clone isolated by this strategy was used as a probe to identify the complete human homolog from Stratagene's HL-60 randomly-primed library. 500,000 pfu's were plated using XL1-Blue cells, transferred onto Nytran filters, and UV-crosslinked with Stratagene's Stratalinker. The partial murine insert was used as a probe and labelled by random-priming using Prime-It (Stratagene) and hybridized with the filters in 50% formamide, 5X SSPE, 0.1% SDS, and 100 µg/ml salmon sperm DNA at 42°. Filters were washed 2 times at room temperature in 2X SSC, and 2 times at 55° in 0.2X SSC. Plaque purified clones were in vivo excised using XL1-Blue cells and R408 helper phage (Stratagene). Sequencing was performed as described above. Finally, the complete murine clone A202 was isolated by using a 5' HindIII fragment from the human clone as a probe to screen the Stratagene $A_{20}$ cDNA library.

FIG. 10A shows the sequence of human pp32 cDNA cloned from HL-60 cells. Amino acids differing in the murine sequence are shown immediately underneath the human sequence. Amino acids missing from the murine sequence are shown as asterisks. Underlined peptides correspond to peptides independently sequenced from murine pp35 which are also apparently found in pp32. Doubly underlined residues shown in bold constitute a possible leucine zipper; note that the candidate zipper is bounded by additional leucines in the sixth positions immediately upstream and downstream. Also note candidate nuclear localization sequences spanning amino acids 60–68 and 108–116.

FIG. 10B diagrams the cDNA clones used to generate the data shown in FIG. 1B. Clones with an "HE," prefix are derived from the human HL-60 cDNA library in lambda-ZAP. Clone m35.7 is from the murine $A_{20}$ lambda gt11 cDNA library and clone mA202.1 is from the murine $A_{20}$ cDNA library in Uni-Zap. The HL2 clone contains the most 5' sequence obtained, therefore all other clones are numbered with respect to its first base. The numbers on the right signify the total length of each clone. 'AAA' designates clones containing poly-A tails. The EcoRI site in HL13 was used to generate a DNA fragment from its extended 3' region. Similarly, the HindH/site in HL2 was used to generate a DNA fragment from 5' end. Both fragments were used as probes in Northern blotting.

EXAMPLE 13 cDNA Encodes pp32

The evidence that the cDNA's thus obtained encode pp32 is several-fold: [1] the polypeptide expressed from a partial murine cDNA clone reacts preferentially with antibodies to native murine pp32; [2] antibodies to the expressed murine pp32 fragment react specifically with pp32 in Western blot analysis of total cellular lysates of $A_{20}$ cells (5); [3] recombinant human pp32 expressed in baculovirus reacts with antibodies to murine pp32 and pp35; and [4] the in vitro translation product of human pp32 cDNA co-migrates with pp32 and not pp35 in Laemmli gels. As additional supporting evidence, the murine pp32 sequence encodes three peptides independently sequenced from purified murine pp35 which are apparently common to both proteins.

The immunologic identification of the murine and human cDNA clones bears further discussion.
Western Blots.

All protein samples were run on 10% SDS-PAGE system (14). They were transferred to vitrocellulose filters (Schleicher and Schuell) in standard Tris/glycine/20% methanol transfer buffer and blocked overnight in 3% BSA/PBS. Primary antibodies were hybridized onto blots at room temperature in 1X tris-buffered saline containing 0.1% Tween 20 (TBS-T) for 1 hour with continuous shaking. After washing the blot at room temperature in TBS-T, a donkey anti-rabbit HRP secondary antibody was applied. Amersham's ECL chemiluminescent Western detection kit was used to visualize binding of the antibodies.

FIG. 11 used an affinity-purified antibody to native pp32 designated anti-pp32n (see Example 4), to analyze the expressed product of a partial murine clone corresponding to amino acids 67 through 247. FIG. 11 shows a 30 second exposure of a Western blot probed with anti-pp32n. Lane A: 5 µg purified recombinant partial murine pp32 from clone 35.7; lane B: $A_{20}$ lysate.

Anti-pp32n specifically identifies pp32 in total cellular lysates of $A_{20}$ cells (lane B) and reacts with the purified recombinant murine fragment (lane A). Anti-pp32n also reacted with the recombinant murine fragment in lysates of transfected bacteria, but failed to react with proteins in untransfected bacterial hosts.
Protein Purification and Analysis.

Murine pp32 and pp35 were purified from $A_{20}$ cells as described previously (see Example 4). A recombinant partial-murine pp32, fragment was expressed and purified from CAG456 *E. coli* cells using the pRX expression vector (10) containing cDNA encoding amino acids 67 through 247 of murine pp32 (pRX32). A single colony of CAG456 containing the pRX32 was grown in 1 ml LB media with 50 µg/ml ampicillin at 30° with vigorous shaking. The saturated culture was then transferred into 50 ml LB with ampicillin and allowed to reach saturation overnight. The saturated culture was then added to 500 ml M9CA media (8) with ampicillin and allowed to grow with vigorous shaking at 30° for 3.5 h. Indol acrylic acid was added to the cells to achieve 10 µg/ml final concentration, and growth was continued for another 4.5 h.

The cells were then pelleted at 4000×g at 4°, washed with 100 ml of 10 mM Tris-HCl, pH 8.0 at 4°, pelleted again and lysed in ice-cold 140 ml STET lysis buffer consisting of 8% sucrose, 10 mM Tris-HCl pH 8.0 at 4°, 50 mM EDTA, 0.5% TRITON X-100, 0.5 mM diisopropylfluorophosphate, and 10 µg/ml each of chymostatin, leupeptin, antipain, and pepstatin. The cell lysate was kept on ice and sonicated 10–11 times with 30 s bursts at intensity level 6 at 15 s intervals using a Brinkmann Sonificator. Cell debris was removed by centrifugation at 13,000×g for 10 min at 4°, the supernatant was brought to 25% ammonium sulfate, and the lysate was allowed to precipitate overnight on ice. The precipitate was pelleted at 13,000×g for 10 min at 4°; the supernatant was then brought to 65% ammonium sulfate and allowed to further precipitate. The protein precipitate was pelleted as before, resuspended in 20 ml of 200 mM NaCl, 20 mM Tris-HCl pH 7.5 at 4°, 1 mM EDTA, 1 mM 2-mercaptoethanol, 0.1 mM phenylmethylsulfonyl fluoride and dialyzed overnight in the same buffer to remove ammonium sulfate.

The dialyzed lysate was applied to a HR-5/5 MonoQ FPLC column (Pharmacia) at a flow rate of 1 ml/min. The column was washed and developed with a 50 ml linear gradient of 200 mM to 1.0 mM NaCl in the same buffer and 1 ml fractions were collected. Samples were analyzed by SDS-PAGE (14) and Western blots probed with anti-pp32 polyclonal antibodies. Pure partial recombinant murine pp32 was usually obtained after only one column run. Material was rechromatographed under the same conditions as needed to obtain >95% purity by SDS-PAGE. Protein concentration was assayed using BCA assay (Pierce).
Polyclonal Antibody Production and Purification.

Purified partial murine recombinant pp32 protein as above was used to prime and boost two Pasteurella-free New Zealand rabbits using bi-weekly 300 µg injections in Freund's adjuvant to produce polyclonal antibodies. For affinity purification of anti-recombinant pp32 from the rabbit serum, an affinity column was prepared and run as previously described for native pp32 (see Example 4).

Production of Human pp32 in Baculovirus.

FIG. 12 shows a parallel experiment performed with the full-length protein product of the human cDNA expressed in baculovirus and purified from infected SF9 cells. pp32 BAC is a recombinant baculovirus into which we subcloned full-length pp32 under the polyhedrin promoter using the pVL1393 transfer plasmid (PharMingen). SF9 cells were maintained in Grace's insect medium supplemented with 10% heat-inactivated fetal bovine serum and 0.05 mg/ml gentamicin at 27°. Initially, SF9 cells were co-transfected with the transfer plasmid and Baculogold virus by calcium phosphate precipitation. The resultant pp32BAC stocks were amplified from a single pfu obtained by end-point dilution. For production of recombinant pp32, SF9 cells infected with pp32BAC were grown in two 1l spinner cultures stirred at 80–90 rpm at 27°; cells were infected at the beginning of log phase growth and collected on day 4 post-infection, after having reached a density of $1.5 \times 10^6$ cells/ml. Cells were harvested and pelleted at 1000×g at 4°, washed with 100 ml medium without serum, pelleted and lysed in ice-cold lysis buffer consisting of 20 mM Tris-HCl, pH 7.5 at 4°, containing 1% TRITON X-100, 1 mM EDTA, 10 mM sodium pyrophosphate, 2 mM sodium vanadate, 3 mM ATP, 50 mM NaF, 0.5 mM diisopropylfluorophosphate, and 0.1 mM phenylmethylsulfonyl fluoride at $2 \times 10^8$ cells/ml with vortexing every 3 min over the course of a 15 min incubation. Cell debris was removed by centrifugation at 17,800×g for 20 min at 4° and recombinant pp32 was filtered at 0.45 μ and 0.22 μ and purified by anion exchange HPLC (1).

FIG. 12 shows a Western blot of a 10% SDS-PAGE gel which was split and developed alternatively with (A) affinity-purified polyclonal antibody to a recombinant murine pp32 fragment or (B) the affinity-purified polyclonal antibodies to denatured pp35 which originally detected pp32 (see Example 4). The figure shows: 4.5 μg recombinant human pp32, lanes 1; 0.45 μg purified native pp32 from HL-60 cells, lanes 2; and 120 μg from murine $A_{20}$ total cell lysate protein, lanes 3. Panel A was exposed for 35 sec., and panel B for 5 min. Lane 3B shows the detection of both pp35 and pp32 in $A_{20}$ lysate.

The purified recombinant human polypeptide (lanes 1) co-migrates with native human pp32 purified from HL-60 cells (lanes 2) and with murine pp32 detected in total lysates of $A_{20}$ cells (lanes 3). Since the human pp32 sequence predicts a polypeptide of 28,585 Da, migration at 32,000 Da on SDS-PAGE gels likely reflects a retardative influence of the acidic domain of pp32, which would be unlikely to bind SDS well. All three polypeptide species react with antibodies specific for pp32 (panel A) and with the original antibodies designated anti-pp35d (1) which first detected the existence of pp32. The in vitro translation product of the full-length murine clone also co-migrates with pp32 (FIG. 13).

In Vitro Transcription and Translation.

Plasmids containing cDNA were linearized and RNA transcripts were synthesized using Promega's RiboMAX T7 polymerase. 3 μg of pp32 RNA was in vitro translated using Promega's rabbit reticulocyte lysate using $^{35}$S-cysteine (ICN) at 30° for 1 hour. 25 μl of lysate was loaded onto a 10% SDS-PAGE gel which was run, transferred to nitrocellulose, and exposed overnight at −80°. A 20 lysate was run alongside to compare the size of the in vitro translated products with proteins recognized by anti-pp35 antibody.

35S-labeled in vitro translation products and $A_{20}$ lysate were electrophoresed on a 10% Laemmli gel and transferred to nitrocellulose. FIG. 13 compares a $^{35}$S autoradiograph of the filter with the corresponding chemiluminescent Western blot image. The figure shows: in vitro translation products of sense RNA from the HL2 human pp32 clone, lane A; $A_{20}$ lysate probed with the same antibody recognizing both pp35 and pp32 illustrated in FIG. 12, lane B; and in vitro translation product of anti-sense RNA from the HL2 human pp35 clone, lane C.

Finally, previously published studies show that polyclonal antibodies raised to and affinity-purified with the expressed murine recombinant fragment (v.s.) preferentially react with pp32 in Western blots of $A_{20}$ cell lysates (5). The confluence of size and immunologic data thus support the identification of the murine and human cDNA clones as pp32.

EXAMPLE 14

Sequence Analysis of pp32 cDNA

Sequence data also indirectly supports the identification of the cDNA clones as pp32. Sequences were analyzed using GCG version 7 software. The underlined sequences in FIG. 10A are identical to peptides independently sequenced from purified native pp35 (see Examples 3 and 11) and thus are likely to represent peptides common to both pp32 and pp35. This supposition is reasonable, given the close correspondence between the peptide maps of the two proteins and the strong cross-reactivity between antibodies raised against either pp32 or pp35. Furthermore, the peptide sequence between residues 138 and 151 closely corresponds to the previously reported sequence from the major pp35 phosphopeptide (see Example 11); this same pp35 phosphopeptide sequence gave rise to the non-degenerate 42-base pair oligonucleotide probe used to obtain the initial pp32 clones. The murine peptide and nucleotide sequences, shown in Table 3 below, are close but non-identical (differences are shown in bold) in pertinent ways. There is sufficient correspondence between the two nucleotide sequences to explain how the pp32 sequence was obtained with a pp35 probe. The pp35 sequence contains a serine at the position equivalent to the $M^{143}$ in the pp32 sequence; it is this serine which appears to be phosphorylated in murine pp35 by casein kinase II (see Example 8). The absence of a casein kinase II phosphorylation site in the pp32 peptide is consistent with the observation that pp32 and pp35 phosphopeptides run distinctly from one another on reversed phase chromatography and precludes the possibility that the cDNA could encode pp35.

TABLE 3

| pp35 Sequence | L L P Q L S Y L D G Y D D E, SEQ ID NO: 6 |
|---|---|
| pp32 Sequence | L L P Q V M Y L D G Y D R D, SEQ ID NO: 7 |
| Screening Probe | ctgctgccccagctgtcctacctggatggctatgatgatgag, SEQ ID NO: 8 |
| pp32 Sequence | ctcctgccccaggtcatgtacctcgatggctatgacagggac, SEQ ID NO: 9 |

The sequence of pp32 predicts several interesting features, illustrated in FIG. 14, a cartoon of pp32 which illustrates the following features: P, potential casein kinase II phosphorylation sites; N, potential nuclear localization signals; LVLL (human) and LILL (murine), potential leucine zippers. Murine is apparently phosphorylated on a single phosphoserine (Malek, et al., 1990); the phosphorylation state of human pp32 has not yet been characterized.

Overall, pp32 is divided into two domains. The N-terminal two-thirds (residues 1 to 167) is generally amphipathic and has a high probability of alpha helical conformation according to Chou-Fasman predictions; approximately at its midpoint, the alpha helical domain has a potential leucine zipper composed of leu-69, val-76, leu-83, and leu-90 (15). The putative leucine zipper sequence is conserved in murine pp32 with one difference: isoleucine is conservatively substituted for the second valine. These features suggest that pp32 might act through selfassociation or through association with other molecules. Preliminary evidence obtained using size exclusion chromatography indicates that both purified native human pp32 and purified full-length human pp32 produced in baculovirus exist in trimeric form in solution (Romantsev and Pastemack, unpublished observations). The N-terminal region also contains two potential nuclear localization sequences commencing at amino acids 61 and 108, respectively; each sequence is comprised of a proline followed by a cluster of basic residues (16). The C-terminal third of pp32 is highly acidic, composed of approximately 70% aspartic acid and glutamic acid residues; the predicted pI of human pp32 is 3.81. While the function of this domain is presently unknown, similar acidic regions have been found on proteins as diverse as neurofilament triple helical L protein (17) and the major centromere binding protein, CENP-b (18).

Human and murine pp32 are quite homologous to one another, but no additional close homologies can be found between pp32 and other molecular species listed in the GenBank, EMBL, and SwissProt databases. Human and murine cDNA are 88% identical; the predicted proteins are 89% identical with conservative substitutions accounting for most of the differences and yielding 95% similarity. Molecules with acidic domains are regularly detected due to the compositional monotony of the acidic regions. Similarly, neurofilament triple helical L protein is identified since it shares the general organizational feature of an N-terminal amphipathic α-helix coupled with a C-terminal acidic tail. The one exception concerns sequence X75090 (HSPHAPI), HLA-DR associated protein I, submitted on Sep. 28, 1993 by M. Vaesen, S. Barnikol-Watanabe, H. Goetz, and N. Hilschmann of the Max Planck/Gottingen to GenBank. This sequence is essentially identical to pp32. We have been unable to identify a related published paper or abstract. We cannot comment on the significance of the findings or association with HLA-DR.

EXAMPLE 15

Expression of pp32 Message

Human pp32 hybridizes with three RNA species in Northern blots of poly-A$^+$RNA from HL-60 cells, and hybridizes reciprocally with two murine species from A$_{20}$ cells under highly stringent conditions. FIG. 15 shows that similar RNA species are reciprocally identified in human and murine RNA in blots probed with human and murine pp32 probes and washed at moderately high stringency.

Northern Blots.

10 µg total RNA and 0.5 µg of poly-A +mRNA from A$_{20}$ or HL-60's were run in formaldehyde/agarose gels using MOPS running buffer (8). RNA was transferred to Amersham's Hybond nylon filters by capillary transfer in 20X SSC. After overnight transfer, the blot was UV-crosslinked and hybridized using the same conditions for probing the HL-60 library with randomly-primed probes. Filters were washed 2 times at room temperature in 2X SSC and 2 times at 55° in 0.2X SSC. Autoradiography was performed at −80°.

Lanes A and C represent 10 µg of total human HL-60 RNA; lanes B and D represent 10 µg of total murine A$_{20}$ RNA. Lanes A and B were probed with human cDNA (clone HL2), and lanes C and D were probed with murine cDNA (clone 35.7). Lanes E and F represent 1 µg poly A$^+$human HL-60 RNA probed either with the 5' HindHi fragment from clone HL2 (lane E) or with an EcoRI fragment from HL13 representing the extended 3' untranslated sequences. All filters were washed at 55° in 0.2 X SSC.

FIG. 15 shows that when the entire coding sequence is used as a probe, a 1.3 kb species apparently corresponding to the cloned species is identified, as well as additional species at 2.2 and 2.3 kb (lane A). The explanation for this phenomenon likely lies in alternative 3' polyadenylation signals, since one additional human pp32 mRNA species has been identified which is 881 nucleotides longer at its 3' end than the HL.2 clone shown in FIG. 10. Clone HL.13 is a 1766 bp cDNA fragment from HL-60 cells which begins on nucleotide 176 of the HL.2 clone of pp32 (FIG. 10) and extends for an additional 881 nucleotides beyond its termination; no poly-A tail is present in HL.13 cDNA, although the 3' extension hybridizes with poly-A$^+$RNA. Except for the 3' extension, it is completely identical to the pp32 sequence. The 1.3, 2.2, and 2.3 kb messages all hybridize in blots of human poly-A$^+$RNA probed with a 5' HindlII fragment of HL.2 (lane E), whereas only the 2.2 and 2.3 kb messages hybridize with an EcoRI fragment representing the 3' terminal 273 bp of HL.13 (lane F). Based upon its hybridization pattern, it is probable that the 2.3 kb species also represents a polyadenylation variant. In human tissues and cell lines, the three pp32 mRNA species appear by Northern analysis to be roughly coequal in their expression. In contrast, only 1.3 and 2.2 kb species are seen in murine cell lines such as A$_{20}$, with the 1.3 kb species predominating (lane D). The predominance of the 1.3 kb form may account for why no murine cDNA clones with extended 3' untranslated regions have been encountered so far.

EXAMPLE 16 pp32 mRNA During Differentiation p32 mRNA is subject to regulation in some cell lines. HL-60 cells are a human leukemic cell line which grow well in culture in an undifferentiated state. When exposed to certain agents such as phorbol ester, HL-60 cells become adherent, express macrophage phenotypic markers, cease proliferation, and accumulate in G$_o$ (19). FIG. 16 shows that steady-state levels of pp32 mRNA greatly diminish when HL-60 cells are exposed to TPA. In this experiment, HL-60 cells were incubated with 100 ng/ml TPA in DMSO or with DMSO vehicle for three hours, then washed and plated for incubation and further observation. 4×10$^5$ HL-60 cells/ml in 100 ml medium were incubated for 3 h at 37° with either 100 ng tetradecanoyl phorbol acetate/ml CYPA, Gibco/BRL) from a 1 mg/ml stock in dimethylsulfoxide or an equal volume of dimethylsulfoxide. In each case, the final concentration of DMSO was 0.01%. The cells were then harvested by centrifugation and either processed for total RNA extraction or washed twice in serum free medium and replanted at 2.5×10$^6$ cells/ml in TPA-free medium. On successive days, cells were harvested by trypsinization and processed for RNA (12).

HL-60 cells were induced to differentiate with TPA and total RNA was extracted 3 hours, 1 day, 2 days, and 3 days after induction. Lanes marked C on FIG. 16 represent control total RNA from HL-60 cells incubated with DMSO vehicle alone. Each lane represents 10 µg total RNA. The blot was probed with human cDNA (HL2), then stripped and reprobed with GAPDH cDNA as a loading control.

FIG. 16 shows a progressive decline of pp32 mRNA species relative to the GAPDH control observable by the first day following plating. By the third day, virtually no pp32 message is present. Essentially identical results have been obtained in a system utilizing the induced differentiation of ML-1 cells (20, and data not shown). In the HL-60 system, pp32 mRNA virtually disappears during the course of differentiation; in a variety of systems, similar behavior has been noted for p53 (21), myc (22,23), myb (20), and heat shock cognate 70 (hsc70) (24). As an additional interesting feature, there is also a moderate diminution of pp32 mRNA in control cells incubated for the full three days; this may reflect a slight, suboptimal induction of differentiation by the 0.01% DMSO used as a vehicle control (11).

The modulation of pp32 mRNA levels as a function of differentiation in HL-60 cells are entirely consistent with observations made in vivo that pp32 mRNA levels high in self-renewing cell populations, but absent in terminally differentiated cells. The experiments do not, however, establish the mechanism whereby pp32 mRNA levels are regulated. On one hand, it is possible that the results reflect modulation of pp32 transcriptional activity; on the other hand, it is possible that pp32 mRNA levels are regulated through message stability.

EXAMPLE 17 pp32 Inhibits Ras-Myc Transformation

In normal tissues in vivo, pp32 is selectively expressed in those cells capable of self-renewal, which, from a teleological standpoint, should resist transformation. By this reasoning, pp32 might potentially act to suppress one or more events leading to transformation. A countervailing observation leads to precisely the opposite suggestion. pp32 is highly expressed in at least several forms of human neoplasia including prostate cancer (5) and non-Hodgkin's lymphoma Kuhajda and Pastemack, unpublished observations) at cellular levels and in proportions of cells which seem to increase with increasing severity of clinical disease. These data suggest that increased pp32 expression favors tumorigenesis. To begin to resolve these questions, we tested the effects of increased pp32 expression on the well-characterized system of transformation of rat embryo fibroblasts by ras and myc (25).

Transfection of Rat Embryo Fibroblasts.

Primary rat embryo fibroblasts were either purchased from BioWhittaker or obtained courtesy of Dr. Chi Dang. For each experiment, approximately 1×10⁶ cells were plated in T75 flasks and incubated for 2 d prior to transfection. For each flask of primary rat embryo fibroblasts, 5 μg pEJ-ras, and/or, 10 μg pMLV-c-myc, and/or 10 μg of pCMV32 or pSV32 and two volumes Lipofectin (twice the total μg DNA=μl Lipofectin) were gently mixed by inversion in 1.5 ml OPTIMEM in sterile 15 ml polystyrene tubes and allowed to incubate at room temperature for >15 min. The amounts were increased proportionately when more than 1 flask was used for each transfection experiment. Cells were washed twice with sterile phosphate-buffered saline, once with OPTIMEM (Gibco-BRL), and then fed with 6 ml of OPTIMEM and 1.5 ml of the DNA/Lipofectin mix. After overnight incubation, the cells were grown in standard media and refed with fresh media twice weekly. Colonies were counted 2 weeks post-transfection. To determine the dose-dependence on pCMV32, pCMV vector and pCMV32 DNA were transfected such that the sum of the two was a constant 12 μg. Ratios of 0:12, 3:9, 6:6, 9:3, and 12:0 μg pCMV: μg pCMV32 were cotransfected into triplicate flasks and foci were counted 2 weeks later.

To determine whether any of the plasmids used were toxic, rat embryo fibroblasts were co-transfected with pCMV, pCMV32, pSV40, or pSV32 along with pHyg. If any of the pp32-containing constructs were lethal, the number of hygromycin-resistant colonies from cells transfected with it would be significantly less than control blank-plasmid transfected cells. 10 μg of test vector and 1 μg of pHyg were transfected per flask of cells using the protocol described above. Each transfection was done in duplicate. 48 h after transfection, 12.5 μg/ml of hygromycin was added to the medium and the cells were allowed to grow for one month, with a weekly medium change. Resistant colonies were stained with crystal violet and counted.

Rat embryo fibroblasts were co-transfected with pEJ-ras, pMLV-c-myc, and the indicated mixtures of pCMV32 and pCMV DNA such that the total amount of transfected DNA was constant in all samples. Colonies counted at 2 weeks post transfection. The figure shows the mean of triplicate measurements +/-standard error.

FIG. 17 shows that pp32 inhibits ras-myc transformation of rat embryo fibroblasts in a dose-dependent fashion. In this experiment, constant amounts of pEJras, pMLVmyc, and pCMV32+pCMV vector DNA were transiently co-transfected into rat embryo fibroblasts. By three weeks post-transfection, cells treated with ras, myc, and 100% pCMV vector DNA produced an average of nearly 100 colonies per flask; cells transfected with ras, myc and 100% pCMV32 DNA averaged around 20 colonies per flask. Intermediate fractions of pCMV32 DNA yielded intermediate dose-dependent reductions. Controls in which either ras or myc but not both were transfected gave <1 average colony per flask.

The inhibition of ras-myc transformation by pp32 is highly reproducible, and is independent of both vector and promoter since similar results were obtained in constructs using an SV40 promoter (Table 4). The effect of pp32 car, not be explained by toxicity of the construct. Co-transfection of pCMV32 or pSV32 plasmids with the hygromycin-selectable plasmid pHlyg (26) did not reduce the number of dually hygromycin-resistant stable transfectants over those obtained with pCMV or pSV40 vectors alone (data not shown).

TABLE 4 pp32-Mediated Inhibition of ras- and myc-Medicated Transformation is Independent of the Promoter

| Experiment | Plasmid | FLASK | | | | % INHIBITION |
|---|---|---|---|---|---|---|
| | | I | II | III | IV | |
| I | pCMV | 49 | 44 | 48 | ND | |
| | pC32 | 8 | 15 | 18 | ND | 70.9 |
| II | pCMV | 42 | 52 | 47 | ND | |
| | pC32 | 14 | 20 | 18 | ND | 63.1 |
| III | pSV40 | 25 | 24 | 20 | 28 | |
| | pSV32 | 6 | 6 | 5 | 9 | 73.2 |
| CONTROL | NONE | 43 | 47 | ND | ND | |
| | pCMV | 48 | 37 | ND | ND | 5.6 |
| | pSV40 | 43 | 40 | ND | ND | 7.8 |

Rat embryo fibroblasts were transfected with pEJras and pMLV-c-myc with either blank plasmids (pCMV or pSV40) or human pp32 cDNA (HL2) carrying plasmids (pCMV32 or pSV32). Transformed foci were counted 2 weeks post-transfection. Control experiments were performed to show that blank plasmids had no effect on transformation (see text).

Figure 18:
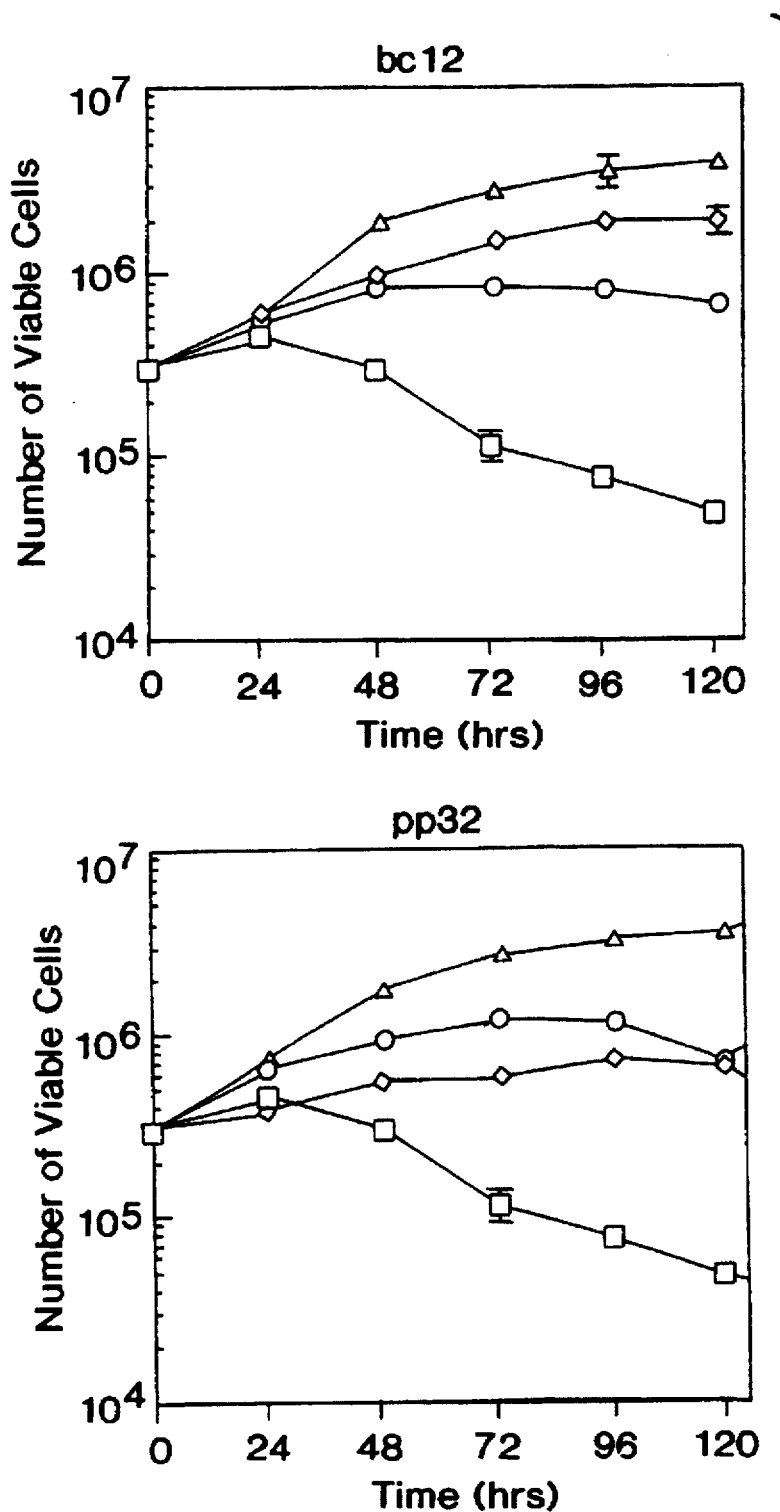
FIG. 18 shows the time course of BC12 and pp32-mediated resistance to drug-induced programmed cell death.
Figure 19A:
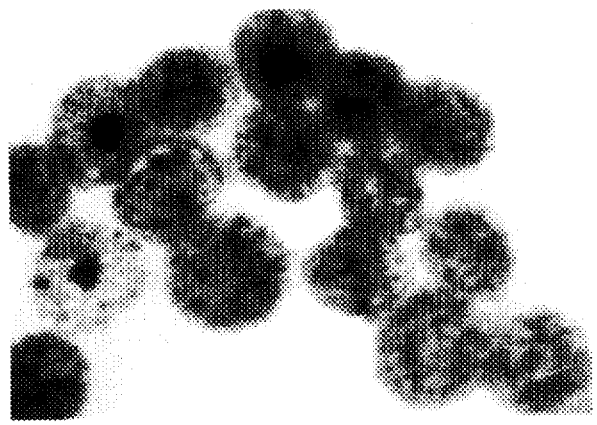
FIG. 19 is a photomicrograph showing the effect of pp32 on nuclear morphology.
Figure 19B:
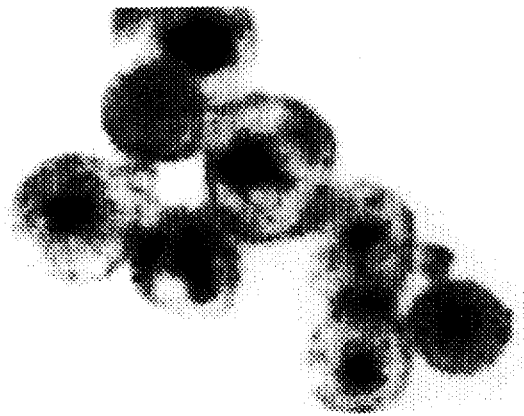
Figure 19C:
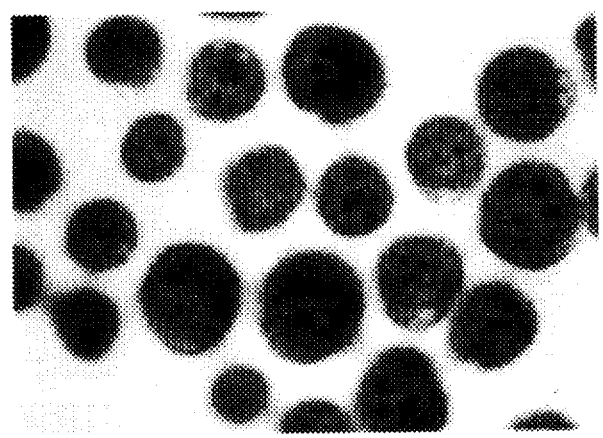
Figure 19D:
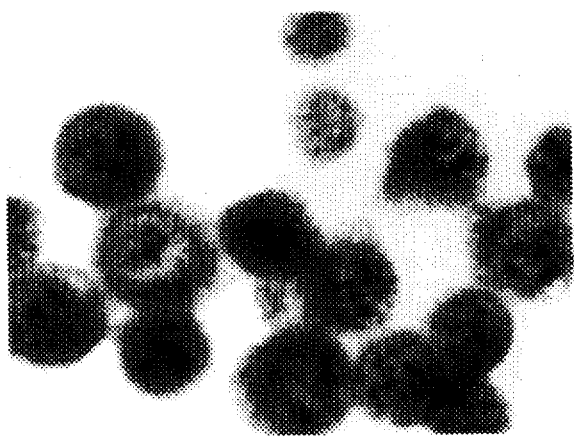

EXAMPLE 18 pp32 and bcl2 Both Cause Persistent Resistance to Drag-Induced Programmed Cell Death AT3 rat prostatic carcinoma cells stably transfected with pp32 are resistant to drug-induced programmed cell death (FIG. 18). In these experiments, AT3-pp32 cells were treated with ionomycin, thapsigargin, or 5-fluorouracil in dose- and time-dependent fashions, and the proportion of surviving cells determined. Death via apoptosis was confirmed by pulsed-field gel electrophoretic analysis of double-stranded DNA breaks and by enumeration of apoptotic bodies. The figure shows the time course of 5-fluorouracil treatment in comparison to AT3 cells stably transfected with bcl2, a cytoplasmic protein conferring resistance, or to control cells.

For each assay, $3 \times 10^6$ cells were plated in the presence or absence of 0.1 µM 5-fluorodeoxyuridine. At the indicated times, cells were harvested and counted. Programmed cell death was verified by pulsed field gel electrophoretic analysis of double-strand DNA breaks. Δ, AT3 cells with no drug treatment: ◊, AT3-bcl2 clone 3or AT3-pp32 clone 3; ○, AT3-bel2 clone 4 or AT3-pp32 clone 5; □, AT3-neo. The figure shows that stably transformed bcl2 and pp32 clones are both persistently resistant to drug-induced programmed cell death.

Programmed cell death requires induction, which can occur through various signaling pathways, and execution, which likely occurs through a final common pathway. 5-fluorouracil induces programmed cell death via a proliferation-dependent pathway, whereas ionomycin and thapsigargin do not, suggesting that induction occurs through different signaling pathways. The fact that pp32 inhibits both strongly suggests that it acts at the heart of the programmed cell death mechanism, the finally common pathway.

EXAMPLE 19 pp32 Modulates Nuclear Morphology pp32 induces changes in nuclear morphology suggestive of high-grade malignancy. FIG. 19 shows Papanicolaou-stained SF9 cells four days following infection with Baculovirus encoding pp32 (A), baculovirus encoding single-strand DNA binding protein (B), wild-type baculovirus (D), or nothing (C). Cells in C show diffuse, finely stippled nuclear chromatin with regular nuclei; the cells in D are similar, save for viral particles. The cells in B show changes common to overexpression of many nuclear proteins; there are non-specific nuclear inclusions, and some of the nuclei are glassy. Similar changes occur with myc, whereas androgen receptor has little effect. In contrast, pp32 in A produces enlarged, irregular nuclei with areas of coarsely dumped chromatin as well as areas of clearing. Non-specific inclusions are also seen. The pp32-specific changes are a cytologic hallmark of malignancy and do not appear to be a general feature of overexpression of a nuclear protein.

Although the foregoing invention has been described in some detail by way of illustration and example for purposes of clarity of understanding, it will be obvious that certain changes and modifications may be practiced within the scope of the appended claims. Modifications of the above-described modes for carrying out the invention that are obvious to persons of skill in medicine, immunology, hybridoma technology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

---

I claim:

1. A diagnostic method for predicting malignant potential of lymphoid and epithelial tumors, comprising:

providing a sample of human lymphoid or epithelial tissue; and determining, in the sample, levels or intracellular sites of expression of a gene product expressed from a gene sequence which hybridizes with the nucleotide sequence of SEQ ID NO:4 or its complement.

2. The method of claim 1 wherein the gene product is mRNA.

3. The method of claim 2 wherein the mRNA is extracted from the sample and quantitated.

4. The method of claim 2 wherein the level of mRNA is determined by in situ hybridization to a section of the tissue sample.

5. The method of claim 2 wherein the mRNA is quantitated by polymerase chain reaction.

6. A diagnostic method for determining, in a sample of human tissue, levels or expression of mRNA which hybridizes under stringent conditions with the nucleotide sequence of SEQ ID NO:1 or its complement, comprising incubating a nucleic acid having a sequence of at least 18 contiguous nucleotides in common with the sequence of SEQ ID NO:1 with nucleic acid of said sample and determining binding between said nucleic acid having a sequence of at least 18 contiguous nucleotides in common with the sequence of SEQ ID NO:1 and said nucleic acid of said sample.

7. The method of claim 6, wherein the mRNA is extracted from the sample and quantitated.

8. The method of claim 6, wherein the level of mRNA is determined by in situ hybridization to a section of the tissue sample.

9. The method according to claim 6, wherein the tissue is a carcinoma.

10. The method according to claim 6, wherein the tissue is a carcinoma or sarcoma of a tissue selected from the group consisting of epithelial, lymphoid, hematopoietic, mesenchymal, central nervous system and peripheral nervous system tissues.

11. The method according to claim 6, wherein the tissue is selected from the group consisting of colon carcinoma, prostate carcinoma and non-Hodgkin's lymphoma.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1052 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Homo sapiens ( i x ) FEATURE:
        ( A ) NAME/KEY: CDS
        ( B ) LOCATION: 97..843

( x i ) SEQUENCE DESCRIPTION: SEQ ID NO:1:

```
GAATTCCCAA  AGTCCTAAAA  CGCGCGGCCG  TGGGTTCGGG  GTTTATTGAT  TGAATTCCGC        60

CGGCGCGGGA  GCCTCTGCAG  AGAGAGAGCG  CGAGAG  ATG  GAG  ATG  GGC  AGA  CGG      114
                                            Met Glu Met Gly Arg Arg
                                             1               5

ATT  CAT  TTA  GAG  CTG  CGG  AAC  AGG  ACG  CCC  TCT  GAT  GTG  AAA  GAA  CTT    162
```

|  |  |  |  |  |  |  |  |  |  |  |  |  |  |  |  |
|---|---|---|---|---|---|---|---|---|---|---|---|---|---|---|---|
| Ile | His | Leu | Glu<br>10 | Leu | Arg | Asn | Arg | Thr<br>15 | Pro | Ser | Asp | Val | Lys<br>20 | Glu | Leu |

| GTC | CTG | GAC | AAC | AGT | CGG | TCG | AAT | GAA | GGC | AAA | CTC | GAA | GGC | CTC | ACA | 210 |
|---|---|---|---|---|---|---|---|---|---|---|---|---|---|---|---|---|
| Val | Leu | Asp<br>25 | Asn | Ser | Arg | Ser | Asn<br>30 | Glu | Gly | Lys | Leu | Glu<br>35 | Gly | Leu | Thr | |

| GAT | GAA | TTT | GAA | GAA | CTG | GAA | TTC | TTA | AGT | ACA | ATC | AAC | GTA | GGC | CTC | 258 |
|---|---|---|---|---|---|---|---|---|---|---|---|---|---|---|---|---|
| Asp | Glu<br>40 | Phe | Glu | Glu | Leu | Glu | Phe<br>45 | Leu | Ser | Thr | Ile | Asn<br>50 | Val | Gly | Leu | |

| ACC | TCA | ATC | GCA | AAC | TTA | CCA | AAG | TTA | AAC | AAA | CTT | AAG | AAG | CTT | GAA | 306 |
|---|---|---|---|---|---|---|---|---|---|---|---|---|---|---|---|---|
| Thr<br>55 | Ser | Ile | Ala | Asn | Leu<br>60 | Pro | Lys | Leu | Asn | Lys<br>65 | Leu | Lys | Lys | Leu | Glu<br>70 | |

| CTA | AGC | GAT | AAC | AGA | GTC | TCA | GGG | GGC | CTA | GAA | GTA | TTG | GCA | GAA | AAG | 354 |
|---|---|---|---|---|---|---|---|---|---|---|---|---|---|---|---|---|
| Leu | Ser | Asp | Asn | Arg<br>75 | Val | Ser | Gly | Gly | Leu<br>80 | Glu | Val | Leu | Ala | Glu<br>85 | Lys | |

| TGT | CCG | AAC | CTC | ACG | CAT | CTA | AAT | TTA | AGT | GGC | AAC | AAA | ATT | AAA | GAC | 402 |
|---|---|---|---|---|---|---|---|---|---|---|---|---|---|---|---|---|
| Cys | Pro | Asn | Leu<br>90 | Thr | His | Leu | Asn | Leu<br>95 | Ser | Gly | Asn | Lys | Ile<br>100 | Lys | Asp | |

| CTC | AGC | ACA | ATA | GAG | CCA | CTG | AAA | AAG | TTA | GAA | AAC | CTC | AAG | AGC | TTA | 450 |
|---|---|---|---|---|---|---|---|---|---|---|---|---|---|---|---|---|
| Leu | Ser | Thr<br>105 | Ile | Glu | Pro | Leu | Lys<br>110 | Lys | Leu | Glu | Asn | Leu<br>115 | Lys | Ser | Leu | |

| GAC | CTT | TTC | AAT | TGC | GAG | GTA | ACC | AAC | CTG | AAC | GAC | TAC | CGA | GAA | AAT | 498 |
|---|---|---|---|---|---|---|---|---|---|---|---|---|---|---|---|---|
| Asp | Leu<br>120 | Phe | Asn | Cys | Glu | Val<br>125 | Thr | Asn | Leu | Asn | Asp<br>130 | Tyr | Arg | Glu | Asn | |

| GTG | TTC | AAG | CTC | CTC | CCG | CAA | CTC | ACA | TAT | CTC | GAC | GGC | TAT | GAC | CGG | 546 |
|---|---|---|---|---|---|---|---|---|---|---|---|---|---|---|---|---|
| Val<br>135 | Phe | Lys | Leu | Leu | Pro<br>140 | Gln | Leu | Thr | Tyr | Leu<br>145 | Asp | Gly | Tyr | Asp | Arg<br>150 | |

| GAC | GAC | AAG | GAG | GCC | CCT | GAC | TCG | GAT | GCT | GAG | GGC | TAC | GTG | GAG | GGC | 594 |
|---|---|---|---|---|---|---|---|---|---|---|---|---|---|---|---|---|
| Asp | Asp | Lys | Glu | Ala<br>155 | Pro | Asp | Ser | Asp | Ala<br>160 | Glu | Gly | Tyr | Val | Glu<br>165 | Gly | |

| CTG | GAT | GAT | GAG | GAG | GAG | GAT | GAG | GAT | GAG | GAG | GAG | TAT | GAT | GAA | GAT | 642 |
|---|---|---|---|---|---|---|---|---|---|---|---|---|---|---|---|---|
| Leu | Asp | Asp | Glu<br>170 | Glu | Glu | Asp | Glu<br>175 | Asp | Glu | Glu | Glu | Tyr<br>180 | Asp | Glu | Asp | |

| GCT | CAG | GTA | GTG | GAA | GAC | GAG | GAG | GAC | GAG | GAT | GAG | GAG | GAG | GAA | GGT | 690 |
|---|---|---|---|---|---|---|---|---|---|---|---|---|---|---|---|---|
| Ala | Gln | Val<br>185 | Val | Glu | Asp | Glu | Glu<br>190 | Asp | Glu | Asp | Glu | Glu<br>195 | Glu | Glu | Gly | |

| GAA | GAG | GAG | GAC | GTG | AGT | GGA | GAG | GAG | GAG | GAG | GAT | GAA | GAA | GGT | TAT | 738 |
|---|---|---|---|---|---|---|---|---|---|---|---|---|---|---|---|---|
| Glu | Glu<br>200 | Glu | Asp | Val | Ser<br>205 | Gly | Glu | Glu | Glu | Glu<br>210 | Asp | Glu | Glu | Gly | Tyr | |

| AAC | GAT | GGA | GAG | GTA | GAT | GAC | GAG | GAA | GAT | GAA | GAA | GAG | CTT | GGT | GAA | 786 |
|---|---|---|---|---|---|---|---|---|---|---|---|---|---|---|---|---|
| Asn<br>215 | Asp | Gly | Glu | Val | Asp<br>220 | Asp | Glu | Glu | Asp<br>225 | Glu | Glu | Glu | Leu | Gly<br>230 | Glu | |

| GAA | GAA | AGG | GGT | CAG | AAG | CGA | AAA | CGA | GAA | CCT | GAA | GAT | GAG | GGA | GAA | 834 |
|---|---|---|---|---|---|---|---|---|---|---|---|---|---|---|---|---|
| Glu | Glu | Arg | Gly | Gln<br>235 | Lys | Arg | Lys | Arg<br>240 | Glu | Pro | Glu | Asp | Glu<br>245 | Gly | Glu | |

| GAT | GAT | GAC | TAAGTGGAAT | AACCTATTTT | GAAAAATTCC | TATTGTATT | 883 |
|---|---|---|---|---|---|---|---|
| Asp | Asp | Asp | | | | | |

| TGACTGTTTT | TACCCATATC | CCCTCTCCCC | CCCCCCTCTA | ATCCTGCCCC | CTGAAACTTA | 943 |
|---|---|---|---|---|---|---|
| TTTTTTTCTG | ATTGTAACGT | TGCTGTGGGA | ACGAGAGGGG | AAGAGTGTAC | TGGGGGTTGC | 1003 |
| GGGGGGAGGA | TGGCGGGTGG | GGGTGGAATA | AAATACTATT | TTTACTGCC | | 1052 |

( 2 ) INFORMATION FOR SEQ ID NO:2:

( i ) SEQUENCE CHARACTERISTICS:
        ( A ) LENGTH: 249 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

-continued

| | | | | | | | | | | | | | | |
|---|---|---|---|---|---|---|---|---|---|---|---|---|---|---|
| Met 1 | Glu | Met | Gly | Arg 5 | Arg | Ile | His | Leu | Glu 10 | Leu | Arg | Asn | Arg | Thr 15 | Pro |
| Ser | Asp | Val | Lys 20 | Glu | Leu | Val | Leu | Asp 25 | Asn | Ser | Arg | Ser | Asn 30 | Glu | Gly |
| Lys | Leu | Glu 35 | Gly | Leu | Thr | Asp | Glu 40 | Phe | Glu | Glu | Leu | Glu 45 | Phe | Leu | Ser |
| Thr | Ile 50 | Asn | Val | Gly | Leu | Thr 55 | Ser | Ile | Ala | Asn | Leu 60 | Pro | Lys | Leu | Asn |
| Lys 65 | Leu | Lys | Lys | Leu | Glu 70 | Leu | Ser | Asp | Asn | Arg 75 | Val | Ser | Gly | Gly | Leu 80 |
| Glu | Val | Leu | Ala | Glu 85 | Lys | Cys | Pro | Asn | Leu 90 | Thr | His | Leu | Asn | Leu 95 | Ser |
| Gly | Asn | Lys | Ile 100 | Lys | Asp | Leu | Ser | Thr 105 | Ile | Glu | Pro | Leu | Lys 110 | Lys | Leu |
| Glu | Asn | Leu 115 | Lys | Ser | Leu | Asp | Leu 120 | Phe | Asn | Cys | Glu | Val 125 | Thr | Asn | Leu |
| Asn | Asp 130 | Tyr | Arg | Glu | Asn | Val 135 | Phe | Lys | Leu | Leu | Pro 140 | Gln | Leu | Thr | Tyr |
| Leu 145 | Asp | Gly | Tyr | Asp | Arg 150 | Asp | Asp | Lys | Glu | Ala 155 | Pro | Asp | Ser | Asp | Ala 160 |
| Glu | Gly | Tyr | Val | Glu 165 | Gly | Leu | Asp | Asp | Glu 170 | Glu | Glu | Asp | Glu | Asp 175 | Glu |
| Glu | Glu | Tyr | Asp 180 | Glu | Asp | Ala | Gln | Val 185 | Val | Glu | Asp | Glu | Glu 190 | Asp | Glu |
| Asp | Glu | Glu 195 | Glu | Glu | Gly | Glu | Glu 200 | Glu | Asp | Val | Ser | Gly 205 | Glu | Glu | Glu |
| Glu | Asp 210 | Glu | Glu | Gly | Tyr | Asn 215 | Asp | Gly | Glu | Val | Asp 220 | Asp | Glu | Glu | Asp |
| Glu 225 | Glu | Glu | Leu | Gly | Glu 230 | Glu | Glu | Arg | Gly | Gln 235 | Lys | Arg | Lys | Arg | Glu 240 |
| Pro | Glu | Asp | Glu | Gly 245 | Glu | Asp | Asp | Asp | | | | | | | |

( 2 ) INFORMATION FOR SEQ ID NO:3:

( i ) SEQUENCE CHARACTERISTICS:
        ( A ) LENGTH: 980 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: mus sp ( x i ) SEQUENCE DESCRIPTION: SEQ ID NO:3:

| | | | | | |
|---|---|---|---|---|---|
| GGCACGAGAA | GAGAGAGCGC | GAGAGATGGA | GATGGACAAA | CGGATTTATT | TAGAGCTGCG | 60 |
| GAACAGGACG | CCCTCTGATG | TGAAAGAGCT | GGTCCTGGAT | AACTGTAAGT | CAATTGAAGG | 120 |
| CAAAATCGAA | GGCCTCACGG | ATGAGTTTGA | AGAACTGGAA | TTCCTAAGTA | CAATCAACGT | 180 |
| AGGCCTCACC | TCCATTTCCA | ACTTACCAAA | GTTAAACAAA | CTCAAGAAGC | TTGAATTAAG | 240 |
| CGAAAACAGA | ATCTCAGGGG | ACCTGGAAGT | ATTGGCAGAG | AAATGTCCGA | ACCTTAAGCA | 300 |
| TCTAAATTTA | AGTGGCAACA | AAATAAAAGA | TCTCAGCACA | ATAGAGCCGC | TGAAGAAGTT | 360 |
| AGAGAATCTC | AAGAGCCTAG | ACCTGTTTAA | CTGTGAGGTG | ACCAACCTGA | ATGCCTACCG | 420 |
| AGAAAACGTG | TTCAAGCTCC | TGCCCCAGGT | CATGTACCTC | GATGGCTATG | ACAGGGACAA | 480 |

| | | | | | | | | |
|---|---|---|---|---|---|---|---|---|
| CAAGGAGGCC | CCCGACTCCG | ATGTTGAGGG | CTACGTGGAG | GATGACGACG | AGGAAGATGA | | | 540 |
| GGATGAGGAG | GAGTATGATG | AATATGCCCA | GCTAGTGGAA | GATGAAGAGG | AAGAGGTTGA | | | 600 |
| GGAGGAAGAA | GGGGAGGAAG | AGGATGTGAG | TGGAGAGGAG | GAGGAGGATG | AGGAAGGTTA | | | 660 |
| CAATGACGGG | GAAGTGGATG | ACGAGGAAGA | CGAAGAAGAA | GCTGGTGAAG | AAGAAGGGAG | | | 720 |
| TCAGAAGCGA | AAACGAGAAC | CGGACGATGA | GGGCGAAGAG | GATGACTAAG | GAATGAACCT | | | 780 |
| GTTTGGGGAA | ATTCCTATTG | TGATTTGACT | GTTTTTACCC | ATATCCCCTC | CCCCTCCTAT | | | 840 |
| TCCTGCCCCC | CGAAACTTAT | TTTTTTCTGA | TTGTAGCATT | GCTGTGGGAA | GGAGAGGGGA | | | 900 |
| AAAGTGTACT | GGGGGTTGAT | GGGGGGTGGG | GGTGGGGGGG | AGGGGTGGAA | TAAAATACTA | | | 960 |
| TTTTTACTGC | CACACTTTAC | | | | | | | 980 |

(2) INFORMATION FOR SEQ ID NO:4:

(i) SEQUENCE CHARACTERISTICS:
    (A) LENGTH: 759 base pairs
    (B) TYPE: nucleic acid
    (C) STRANDEDNESS: double
    (D) TOPOLOGY: linear (ii) MOLECULE TYPE: cDNA (vi) ORIGINAL SOURCE:
    (A) ORGANISM: Mus sp (ix) FEATURE:
    (A) NAME/KEY: CDS
    (B) LOCATION: 3..548

(xi) SEQUENCE DESCRIPTION: SEQ ID NO:4:

```
CG GTC AAG AAG CTT GAA TTA AGC GAA AAC AGA ATC TCA GGG GAC CTG      47
   Val Lys Lys Leu Glu Leu Ser Glu Asn Arg Ile Ser Gly Asp Leu
    1               5                  10                 15

GAA GTA TTG GCA GAG AAA TGT CCG AAC CTT AAG CAT CTA AAT TTA AGT    95
Glu Val Leu Ala Glu Lys Cys Pro Asn Leu Lys His Leu Asn Leu Ser
        20                  25                  30

GGC AAC AAA ATA AAA GAT CTC AGC ACA ATA GAG CCG CTG AAG AAG TTA   143
Gly Asn Lys Ile Lys Asp Leu Ser Thr Ile Glu Pro Leu Lys Lys Leu
            35                  40                  45

GAG AAT CTC AAG AGC CTA GAC CTG TTT AAC TGT GAG GTG ACC AAC CTG   191
Glu Asn Leu Lys Ser Leu Asp Leu Phe Asn Cys Glu Val Thr Asn Leu
 50                  55                  60

AAT GCC TAC CGA GAA AAC GTG TTC AAG CTC CTG CCC CAG GTC ATG TAC   239
Asn Ala Tyr Arg Glu Asn Val Phe Lys Leu Leu Pro Gln Val Met Tyr
 65                  70                  75

CTC GAT GGC TAT GAC AGG GAC AAC AAG GAG GCC CCC GAC TCC GAT GTT   287
Leu Asp Gly Tyr Asp Arg Asp Asn Lys Glu Ala Pro Asp Ser Asp Val
 80                  85                  90                  95

GAG GGC TAC GTG GAG GAT GAC GAC GAG GAA GAT GAG GAT GAG GAG GAG   335
Glu Gly Tyr Val Glu Asp Asp Asp Glu Glu Asp Glu Asp Glu Glu Glu
                100                 105                 110

TAT GAT GAA TAT GCC CAG CTA GTG GAA GAT GAA GAG GAA GAG GTT GAG   383
Tyr Asp Glu Tyr Ala Gln Leu Val Glu Asp Glu Glu Glu Glu Val Glu
                115                 120                 125

GAG GAA GAA GGG GAG GAA GAG GAT GTG AGT GGA GAG GAG GAG GAG GAT   431
Glu Glu Glu Gly Glu Glu Glu Asp Val Ser Gly Glu Glu Glu Glu Asp
        130                 135                 140

GAG GAA GGT TAC AAT GAC GGG GAA GTG GAT GAC GAG GAA GAC GAA GAA   479
Glu Glu Gly Tyr Asn Asp Gly Glu Val Asp Asp Glu Glu Asp Glu Glu
145                 150                 155

GAA GCT GGT GAA GAA GAA GGG AGT CAG AAG CGA AAA CGA GAA CCG GAC   527
Glu Ala Gly Glu Glu Glu Gly Ser Gln Lys Arg Lys Arg Glu Pro Asp
```

|     |     |     |     |     |     |     |     |     |     |     |
| --- | --- | --- | --- | --- | --- | --- | --- | --- | --- | --- |
| 160 |     |     |     | 165 |     |     | 170 |     |     | 175 |
| GAT | GAG | GGC | GAA | GAG | GAT | GAC | TAAGGAATGA | ACCTGTTTGG | GGAAATTCCT | 578 |
| Asp | Glu | Gly | Glu | Glu | Asp | Asp | | | | |
|     |     |     |     | 180 |     |     | | | | |

```
ATTGTGATTT GACTGTTTTT ACCCATATCC CCTCCCCCTC CTATTCCTGC CCCCCGAAAC   638
TTATTTTTTT CTGATTGTAG CATTGCTGTG GGAAGGAGAG GGGAAAAGTG TACTGGGGGT   698
TGATGGGGGG TGGGGTGGG GGGGAGGGGA ATAAAATACT ATTTTACTG CCACACTTTA    758
C                                                                  759
```

( 2 ) INFORMATION FOR SEQ ID NO:5:

( i ) SEQUENCE CHARACTERISTICS:
        ( A ) LENGTH: 182 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Val Lys Lys Leu Glu Leu Ser Glu Asn Arg Ile Ser Gly Asp Leu Glu
 1               5                  10                  15

Val Leu Ala Glu Lys Cys Pro Asn Leu Lys His Leu Asn Leu Ser Gly
            20                  25                  30

Asn Lys Ile Lys Asp Leu Ser Thr Ile Glu Pro Leu Lys Lys Leu Glu
        35                  40                  45

Asn Leu Lys Ser Leu Asp Leu Phe Asn Cys Glu Val Thr Asn Leu Asn
    50                  55                  60

Ala Tyr Arg Glu Asn Val Phe Lys Leu Leu Pro Gln Val Met Tyr Leu
65                  70                  75                  80

Asp Gly Tyr Asp Arg Asp Asn Lys Glu Ala Pro Ser Asp Val Glu
            85                  90                  95

Gly Tyr Val Glu Asp Asp Glu Glu Asp Glu Asp Glu Glu Glu Tyr
            100                 105                 110

Asp Glu Tyr Ala Gln Leu Val Glu Asp Glu Glu Glu Val Glu Glu
            115                 120                 125

Glu Glu Gly Glu Glu Glu Asp Val Ser Gly Glu Glu Glu Glu Asp Glu
130                 135                 140

Glu Gly Tyr Asn Asp Gly Glu Val Asp Asp Glu Glu Asp Glu Glu Glu
145                 150                 155                 160

Ala Gly Glu Glu Glu Gly Ser Gln Lys Arg Lys Arg Glu Pro Asp Asp
                165                 170                 175

Glu Gly Glu Glu Asp Asp
                180
```

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Mus sp ( x i ) SEQUENCE DESCRIPTION: SEQ ID NO:6:

```
Leu Leu Pro Gln Leu Ser Tyr Leu Asp Gly Tyr Asp Asp Glu
 1               5                  10
```

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Mus sp ( x i ) SEQUENCE DESCRIPTION: SEQ ID NO:7:

```
Leu  Leu  Pro  Gln  Val  Met  Tyr  Leu  Asp  Gly  Tyr  Asp  Arg  Asp
 1                  5                        10
```

( 2 ) INFORMATION FOR SEQ ID NO:8:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: YES ( v i ) ORIGINAL SOURCE:
        ( A ) ORGANISM: unknown ( x i ) SEQUENCE DESCRIPTION: SEQ ID NO:8:

```
CTGCTGCCCC AGCTGTCCTA CCTGGATGGC TATGATGATG AG                 42
```

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( A ) ORGANISM: Mus sp ( x i ) SEQUENCE DESCRIPTION: SEQ ID NO:9:

```
CTCCTGCCCC AGGTCATGTA CCTCGATGGC TATGACAGGG AC                 42
```